(12) United States Patent
Picker et al.

(10) Patent No.: US 10,101,329 B2
(45) Date of Patent: *Oct. 16, 2018

(54) CMV GLYCOPROTEINS AND RECOMBINANT VECTORS

(71) Applicant: OREGON HEALTH & SCIENCE UNIVERSITY, Portland, OR (US)

(72) Inventors: Louis Picker, Portland, OR (US); Klaus Frueh, Portland, OR (US); Scott G. Hansen, Portland, OR (US); Colin Powers, San Diego, CA (US)

(73) Assignee: Oregon Health & Science University, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/374,938

(22) Filed: Dec. 9, 2016

(65) Prior Publication Data

US 2017/0350887 A1 Dec. 7, 2017

Related U.S. Application Data

(63) Continuation of application No. 14/179,152, filed on Feb. 12, 2014, now Pat. No. 9,541,553, which is a continuation of application No. 13/626,398, filed on Sep. 25, 2012, which is a continuation-in-part of application No. PCT/US2011/029930, filed on Mar. 25, 2011.

(60) Provisional application No. 61/317,647, filed on Mar. 25, 2010.

(51) Int. Cl.
| | |
|---|---|
| *G01N 33/569* | (2006.01) |
| *A61K 39/00* | (2006.01) |
| *A61K 39/12* | (2006.01) |
| *A61K 39/21* | (2006.01) |
| *C12N 7/00* | (2006.01) |
| *A61K 39/245* | (2006.01) |
| *A61K 39/02* | (2006.01) |

(52) U.S. Cl.
CPC ....... *G01N 33/56972* (2013.01); *A61K 39/00* (2013.01); *A61K 39/0011* (2013.01); *A61K 39/02* (2013.01); *A61K 39/12* (2013.01); *A61K 39/21* (2013.01); *A61K 39/245* (2013.01); *C12N 7/00* (2013.01); *A61K 2039/5254* (2013.01); *C12N 2710/10343* (2013.01); *C12N 2710/16134* (2013.01); *C12N 2710/16143* (2013.01); *C12N 2710/24143* (2013.01); *C12N 2740/10034* (2013.01); *C12N 2740/15043* (2013.01)

(58) Field of Classification Search
CPC .......... A61K 2300/00; A61K 39/12; A61K 39/0011; A61K 2039/53; A61K 35/17; A61K 39/245; A61K 39/39; A61K 2039/545; A61K 48/00; A61K 2039/5254; A61K 2039/5256; A61K 2039/58; A61K 39/42; A61K 2039/525; A61K 2039/5252; C12N 7/00; C12N 15/86; C12N 2710/16122; C12N 2710/16121; C12N 2710/16151; C12N 2710/16162; C12N 15/869; C12N 2710/16111; C12N 2710/16132; C12N 2710/16141; C12N 2710/16142; C12N 2710/16161

See application file for complete search history.

(56) References Cited

U.S. PATENT DOCUMENTS

| | | |
|---|---|---|
| 5,273,876 A | 12/1993 | Hock et al. |
| 5,720,957 A | 2/1998 | Jones et al. |
| 5,830,745 A | 11/1998 | Hock et al. |
| 6,033,671 A | 3/2000 | Frueh et al. |
| 7,892,822 B1 | 2/2011 | Koszinowski et al. |
| 2002/0176870 A1 | 11/2002 | Schall et al. |
| 2003/0118568 A1 | 6/2003 | Crew |
| 2004/0086489 A1 | 5/2004 | Schall et al. |
| 2004/0248300 A1 | 12/2004 | Preston |
| 2005/0064394 A1 | 3/2005 | Liu et al. |
| 2005/0118192 A1 | 6/2005 | Boursnell et al. |
| 2006/0019369 A1 | 1/2006 | Hahn |
| 2008/0199493 A1 | 8/2008 | Picker et al. |
| 2009/0148477 A1 | 6/2009 | Bruder et al. |

(Continued)

FOREIGN PATENT DOCUMENTS

| | | |
|---|---|---|
| EP | 0521427 A1 | 1/1993 |
| WO | WO 1988/10311 A2 | 12/1988 |

(Continued)

OTHER PUBLICATIONS

Basta, Sameh, et al., "Inhibitory Effects of Cytomegalovirus Proteins US2 and US11 Point to Contributions from Direct Priming and Cross-Priming in Induction of Vaccinia Virus-Specific COB+ T Cells," The Journal of Immunology, 2002, vol. 168, pp. 5403-5408.

(Continued)

*Primary Examiner* — Rachel B Gill
(74) *Attorney, Agent, or Firm* — Sterne, Kessler, Goldstein & Fox P.L.L.C.

(57) ABSTRACT

This invention also relates to recombinant vectors expressing one or more of the human CMV (HCMV) glycoproteins US2, US3, US6 and US11 or corresponding functional rhesus CMV (RhCMV) homologues Rh182, Rh184, Rh185 or Rh189, methods of making them, uses for them, expression products from them, and uses for the expression products. This invention also relates to recombinant cytomegalovirus vectors vectors lacking one or more of the glycoproteins, methods of making them, uses for them, expression products from them, and uses for the expression products.

46 Claims, 33 Drawing Sheets
(4 of 33 Drawing Sheet(s) Filed in Color)
Specification includes a Sequence Listing.

(56) References Cited

U.S. PATENT DOCUMENTS

| | | |
|---|---|---|
| 2009/0203144 A1 | 8/2009 | Beaton et al. |
| 2009/0297555 A1 | 12/2009 | Kemble et al. |
| 2013/0136768 A1 | 5/2013 | Picker et al. |
| 2013/0142823 A1 | 6/2013 | Picker et al. |
| 2013/0156808 A1 | 6/2013 | Jonjic |
| 2013/0202638 A1 | 8/2013 | Thirion et al. |

FOREIGN PATENT DOCUMENTS

| | | |
|---|---|---|
| WO | WO 1996/04383 A1 | 2/1996 |
| WO | WO 1999/006582 A1 | 2/1999 |
| WO | WO 2002/062296 A2 | 8/2002 |
| WO | WO 2006/031264 A2 | 3/2006 |
| WO | WO 2011/093858 A1 | 8/2011 |
| WO | WO 2011/138040 A2 | 11/2011 |
| WO | WO 2011/143653 A2 | 11/2011 |
| WO | WO 2012/170765 A2 | 12/2012 |

OTHER PUBLICATIONS

Besold, K. et al., "Immune Evasion Proteins gpUS2 and gpUS11 of Human Cytomegalovirus Incompletely Protect Infected Cells from COB T Cell Recognition," Virology, Jun. 30, 2009, vol. 391, pp. 5-19.

Borst, E et al., "Development of a Cytomegalovirus Vector for Somatic Gene Therapy," Bone Marrow Transplantation, 2000, vol. 25, Supp. 2, pp. S80-S82.

Borst, Eva Maria et al., "Construction of a Cytomegalovirus-Based Amplicon: A Vector with a Unique Transfer Capacity," Human Gene Therapy, Jul. 1, 2003, vol. 14, pp. 959-970.

Bresnahan, Wade et al., "Replication of Wild-Type and Mutant Human Cyomegalovirus in Life-Extended Human Diploid Fibroblasts," Journal of Virology, Nov. 2000, vol. 74, No. 22, pp. 10816-10818.

Bresnahan, Wade et al., "UL82 Virion Protein Activates Expression of Immediate Early Viral Genes in Human Cytomegalovirus-Infected Cells," Proc Nat Acad Sci, Dec. 19, 2000, vol. 97, No. 26, pp. 14506-14511.

Brondke, H. "Human Herpesvirus 5, Towne Strain," US3 (NCBI GenBank Acc. No. AAS49002), Dep. Apr. 8, 2004.

Brondke, H. "Human Herpesvirus 5, Towne Strain," US6 (NCBI GenBank Acc. No. AAS49004), Dep. Apr. 8, 2004.

Campadelli-Flume, et al., Editors, "Chapter 15: Betaherpes Viral Genes and Their Functions" Human Herpesviruses: Biology, Therapy, and Immunoprophylaxis. Cambridge: Cambridge University Press, 2007.

Cantrell, Stacy R. et al., "Human Cytomegalovirus (HCMV) UL82 Gene Product (pp. 71) Relieves hDaxx-Mediated Repression of HMCV Replication," Journal of Virology, Jun. 2006, vol. 80, No. 12, pp. 6188-6191.

Cantrell, Stacy R. et al., "Interaction Between the Human Cytomegalovirus UL82 Gene Product (pp. 71) and hDaxx Regulates Immediate-Early Gene Expression and Viral Replication," Journal of Virology, Jun. 2005, vol. 79, No. 12, pp. 7792-7802.

Chang, W.L. et al., "Cloning of the Full-Length Rhesus Ctyomegalovirus Genome as an Infectious and Self-Excisable Bacterial Artificial Chromosome for Analysis of Viral Pathogenesis," Journal of Virology, May 2003, vol. 77, No. 9, pp. 5073-5083.

Chau, Nha H. et al., "Transcriptional Regulation of the Human Cytomegalovirus US11 Early Gene," Journal of Virology, Feb. 1999, vol. 73, No. 2, pp. 863-870.

Davison et al., "New Genes from Old: Redeployment of dUTPase by Herpesviruses," Journal of Virology, Oct. 2005, vol. 79, No. 20, pp. 12880-12892.

Dunn, Walter, et al., "Functional Profiling of a Human Cytomegalovirus Genome," Proc Natl Acad Sci, Nov. 25, 2003, vol. 100, No. 24, pp. 14223-14228.

Gorman, Shelley et al., "Prior Infection with Murine Cytomegalovirus (MCMC) limits the Immunocontraceptive Effects of an MCMV Vector Expressing the Mouse-zona-pellucida-3 Protein," Vaccine, Jun. 2008, vol. 26, pp. 3860-3869.

Grimwood, J_ et al., "NCBI GenBank Direct Submission," Acc. No. AC146906, Sub. Nov. 5, 2003.

Hahn, Gabriele et al., "Human Cytomegalovirus UL 131-128 Genes are Indispensible for Virus Growth in Endothelial Cells and Virus Transfer to Leukocytes," Journal of Virology, Sep. 2004, vol. 78, No. 18, pp. 10023-10032.

Halary, Franck et al., "Human Cytomegalovirus Binding to DC-SIGN is Required for Dendritic Cell Infection and Target Cell trans-Infection," Immunity, Nov. 2002, vol. 17, pp. 653-664.

Hansen, S.G. et al., "Profound Early Control of Highly Pathogenic SIV by an Effector Memory T-cell Vaccine," Nature, May 26, 2011, vol. 473, pp. 523-530.

Hansen, Scott G. et al., "Effector Memory T Cell Responses are Associated with Protection of Rhesus Monkeys from Mucosal Simian Immunodeficiency Virus Challenge," Nature Medicine, Mar. 2009, vol. 15, No. 3, pp. 293-312.

Hansen, Scott G. et al., "Evasion of COB+ T Cells is Critical for Super-Infection by Cytomegalovirus," Science, Apr. 2, 2010, vol. 328, No. 5974, pp. 102-106.

Hansen, Scott G., et al., "Complete Sequence and Genomic Analysis of Rhesus Cytomegalovirus," Journal of Virology, Jun. 2003, vol. 77, No. 12, pp. 6620-6636.

Jones, Thomas R. et al., "Multiple Independent Loci Within the Human Cytomegalovirus Unique Short Region Down-Regulate Expression of Major Histocompatibility Complex Class I Heavy Chains," Journal of Virology, Aug. 1995, vol. 69, No. 8, pp. 4830-4841.

Jones, Thomas R. et al., "Replacement Mutagenesis of the Human Cytomegalovirus Genome: US10 and US11 Gene Products are Nonessential," Journal of Virology, Nov. 1991, vol. 65, No. 11, pp. 5860-5872.

Kaech, Susan M. et al., "Effector and Memory T-Cell Differentiation. Implications for Vaccine Development," Nature Reviews, Apr. 2002, vol. 2 pp. 251-262.

Kalejta, Robert F. et al., "Human Cytomegalovirus pp71: A New Viral Tool to Probe the Mechanisms of Cell Cyle Progression and the Oncogenesis Controlled by the Retinoblastoma Family of Tumor Suppressors," Journal of Cellular Biochemistry, Apr. 2004, vol. 93, pp. 37-45.

Karrer et al., "Expansion of Protective COB+ T-Cell Responses Driven by Recombinant Cytomegaloviruses," Journal of Virology, Mar. 2004, vol. 78, No. 5, pp. 2255-2264.

Lilja, Anders E. et al., "Functional Genetic Analysis of Rhesus Cytomegalovirus: Rh01 is an Epithelial Cell Tropism Factor," Journal of Virology, Mar. 2008, vol. 82, No. 5, pp. 2170-2181.

Mahmood, Kutubuddin et al., "Human Cytomegalovirus Plasmid-based Amplicon Vector System for Gene Therapy," Genetic Vaccines and Therapy, Jan. 26, 2005, vol. 3, No. 1:1.

Marshall, Ker R. et al., "Activity and Intracellular Localization of the Human Cytomegalovirus Protein pp71," Journal of General Virology, Mar. 2002, vol. 83, pp. 1601-1612.

Mc Gregor, Alistair et al., Molelcular, Biological, and In Vivo Characterization of the Guinea Pig Cytomegalovirus (CMV) Homologs of the Human CMV Matrix Proteins pp71 (UL82) and pp65 (UL83), Journal of Virology, Sep. 2004, vol. 78, No. 18, pp. 9872-9889.

Mohr, Christian A. et al., "A Spread-Deficient Cytomegalovirus for Assessment of First-Target Cells in Vaccination," Journal of Virology, Aug. 2010, vol. 84, No. 15, pp. 7730-7742.

Mohr, Christian A. et al., "Engineering of Cytomegalovirus Genomes for Recombinant Live Herpesvirus Vaccines," International Journal of Medical Microbiology, 2008, vol. 298, pp. 115-125.

Moutaftsi, Magdalena et al., "Human Cytomegalovirus Inhibits Maturation and Impairs Function of Monocyte-derived Dendritic Cells," Blood, Apr. 15, 2002, vol. 99, No. 8, pp. 2913-2921.

Murphy, Cynthia G et al., "Vaccine Protection against Simian Immunodeficiency Virus by Recombinant Strains of Herpes Simplex Virus," Journal of Virology, Sep. 2000, vol. 74, No. 17, pp. 7745-7754.

Murphy, Eain et al., "Coding Potential of Laboratory and Clinical Strains of Human Ctyomegalovirus," Proc Nat Acad Sci, Dec. 9, 2003, vol. 100, No. 25, pp. 14976-14981.

(56) References Cited

OTHER PUBLICATIONS

Office Action for U.S. Appl. No. 11/597,457, dated Aug. 4, 2015.
Olaleye, O.D. et al., "Cytomegalovirus Infection Among Tuberculosis Patients in a Chest Hospital in Nigeria," Comp. Immun. Microbial. Infect. Dis. 1990, vol. 13, No. 2, pp. 101-106.
Onuffer, James J_ et al., "Chemokines, Chemokine Receptors and Small-molecule Antagonists: Recent Developments," Trends in Pharmacological Sciences, Oct. 2002, vol. 23, No. 10, pp. 459-467.
Oxford, Kristie et al., "Protein Coding Content of the ULb' Region of Wild-type Rhesus Cytomegalovirus," Virology, Mar. 30, 2008, vol. 373, No. 1, pp. 181-183.
Oxxon Terapeutics Licenses Rights to Xenova's DISC-HSV and DISC-GM-CSF Vector Technolgies, BusinessWire, Jan. 13, 2005.
Plotkin, Stanley A. et al., "Vaccines for the Prevention of Human Cytomegalovirus Infection," Reviews of Infectious Diseases, Sep.-Oct. 1990, vol. 12, Supplement 7, pp. S827-S838.
Powers, Colin et al., "Rhesus CMV: An Emerging Animal Model for Human CMV," Med Microbial Immunol., Jun. 2008, vol. 197, No. 2, pp. 109-115.
Redwood, Alec J_ et al., "Use of a Murine Cytomegalovirus K181-Derived Bacterial Artificial Chromosome as a Vaccine Vector for Immunocontraception," Journal of Virology, Mar. 2005, vol. 79, No. 5, pp. 2998-3008.
Rizvanov, Albert et al., "Generation of a Recombinant Cytomegalovirus for Expression of a Hantavirus Glycoprotein," Journal of Virology, 2003, vol. 77, No. 22, pp. 12203-12210.
Ryckman, Brent J_ et al., "Characterization of the Human Cytomegalovirus gH/gL/US128-131 Complex That Mediates Entry into Epithelian and Endothelial Cells," Journal of Virology, Jan. 2008, vol. 82, No. 1, pp. 60-70.
Tessmer, Marlowe S. et al., "Salivary Gland NK Cells are Phenotypically and Functionally Unique," PLoS Pathogens, Jan. 2011, vol. 7, Issue 1, pp. 1-9.
Wang, Xiuqing et al., "Murine Cytomegalovirus Abortively Infects Human Dendritic Cells, Leading to Expression and Presentation of Virally Vectored Genes," Journal of Virology, Jul. 2003, vol. 77, No. 13, pp. 7182-7192.
Wiertz, Emmanuel J.H. J_ et al, "The Human Cytomegalovirus US11 Gene Product Dislocates MHC Class I Heavy Chains from the Endoplasmic Reticulum to the Cytosol," Cell, Mar. 8, 1996, vol. 84, pp. 769-779.
Dudek, T., et al., "Replication-defective Viruses as Vaccines and Vaccine vectors," Virology 344:230-239, Elsevier, Netherlands (2006).
Kropff, B., et al., "Identification of the gene coding for rhesus cytomegalovirus glycoprotein B and immunological analysis of the protein," J. Gen Virol. 78(pt 8):1999-2007, Microbiology Society, United Kingdom (1997).
Schleiss M.R., et al., "Genetically engineered live-attenuated cytomegalovirus (CMV) vaccines improve pregnancy outcome in the guinea-pig model of the congenital CMV infection," Retrovirology, Dominique Dormont Int'l Conf Paris, France, Dec. 13-15, 2007.
Hagemier, S.C., "Functional Analysis of the Human Cytomegalovirus UL82 gene product PP71 protein during Virus Replication," Doctoral Dissertation, The University of Texas Southwestern Medical Center at Dallas, 2007.
Office Action dated Jan. 9, 2015, in U.S. Appl. No. 14/179,152, inventors Picker, L., et al., filed Feb. 12, 2014, 20 pages.
Office Action dated Mar. 14, 2016, in U.S. Appl. No. 14/179,152, inventors Picker, L., et al., filed Feb. 12, 2014, 16 pages.

B

C

RM#23716 (CMV/CMV)

(analysis of purified blood CD4+ T cells)

| 23716 Draw Date | plasma vl per ml | C-A DNA Per 10(5) | C-A RNA Per 10(5) |
|---|---|---|---|
| 4/13/09 | BELOW 30 | Below 10 | Below 10 |
| 4/20/09 | BELOW 30 | 80 | Below 10 |
| 4/27/09 | 40,000,000 | 11,000 | 28,000 |
| 5/4/09 | 280,000 | 1,100 | 1,000 |
| 5/11/09 | BELOW 30 | Below 10 | Below 10 |
| 5/18/09 | BELOW 30 | | |
| 5/24/09 | BELOW 30 | | |
| 6/1/09 | BELOW 30 | | |
| 6/8/09 | BELOW 30 | | |
| 6/15/09 | BELOW 30 | 330 | Below 10 |
| 6/22/09 | 60 | 120 | Below 10 |
| 6/29/09 | BELOW 30 | 30 | Below 10 |
| 7/6/09 | BELOW 30 | 40 | Below 10 |

FIG. 15

Ag-Specific Response Assays: Routine Staining Panel

| | PB | AmCy | FITC | PE | ECD | TrR | PC7 | APC | A700 | AC7 | Comments |
|---|---|---|---|---|---|---|---|---|---|---|---|
| A | Cytokine flow cytometry tubes | | | | | | | | | | |
| 1 | CCR7 | CD4 | Ki-67 | TNFα | CD28* | CD69 | CD95 | IFNγ | CD3 | CD8 | TNFa, IFNg: *in vivo* prolif.; central/effector memory |
| 2 | CCR7 | CD4 | CD107 | MIP-1β*** | CD28* | CD69 | CD95 | TNFα | CD3 | CD8 | TNFa, MIP-1b;: degranulation;. cent./effec. mem. |
| 3 | HLA-DR | CD4 | IFNγ | CD25 | CD28* | CD69 | TNFα | PD-1 | CD3 | CD8 | TNFa, IFNg: *in vivo* activation |
| B | CFSE dilution tubes | | | | | | | | | | |
| 1 | CD3 | ... | CFSE^ | Ki-67 | ... | CD4 | ... | CD8 | ... | ... | proliferative capacity |

Notes: PB=Pacific Blue; AmCy=AmCyan; FITC=fluorescein; PE=phycoerythrin; ECD=PE-TexasRed; TrR=TrueRed (PerCP-Cy5.5); APC=allophycocyanin;

A700=Alexa700; PC7=PE-Cy7; AC7=APC-Cy7 intracellular Ags are in bold; *CD28 conjugates provided as co-stimulation along with CD49d mAb in stim.

culture; CD107 Ab also included with cells during incubation; *IL-2 may be substituted in selected analyses; ^CFSE is incorporated into cells prior to assay

FIG. 21

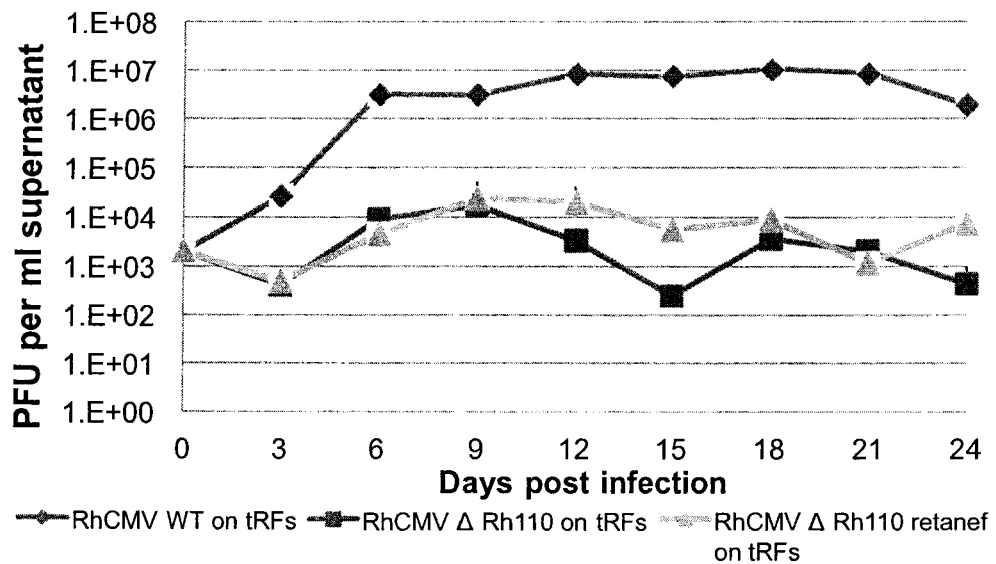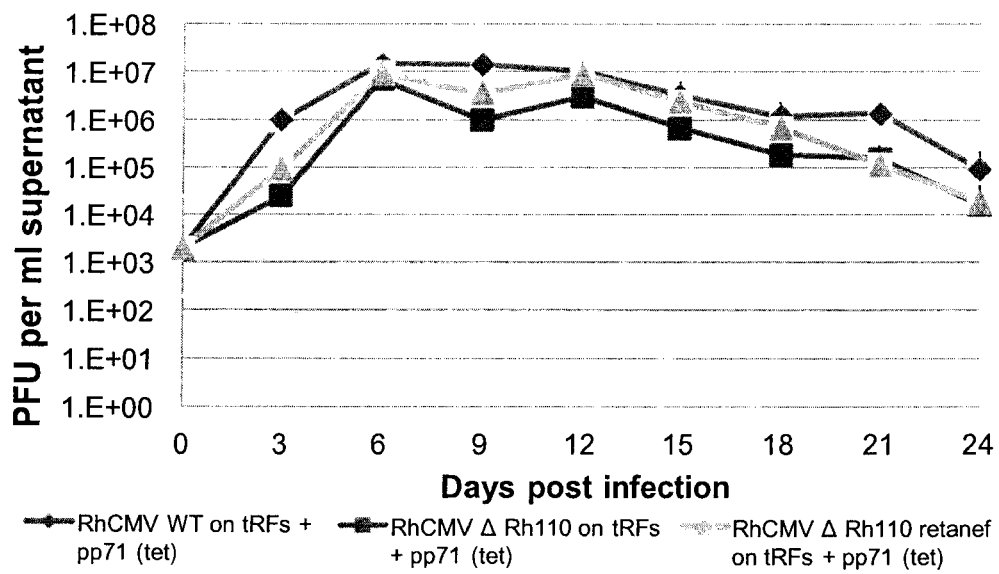
FIG. 22

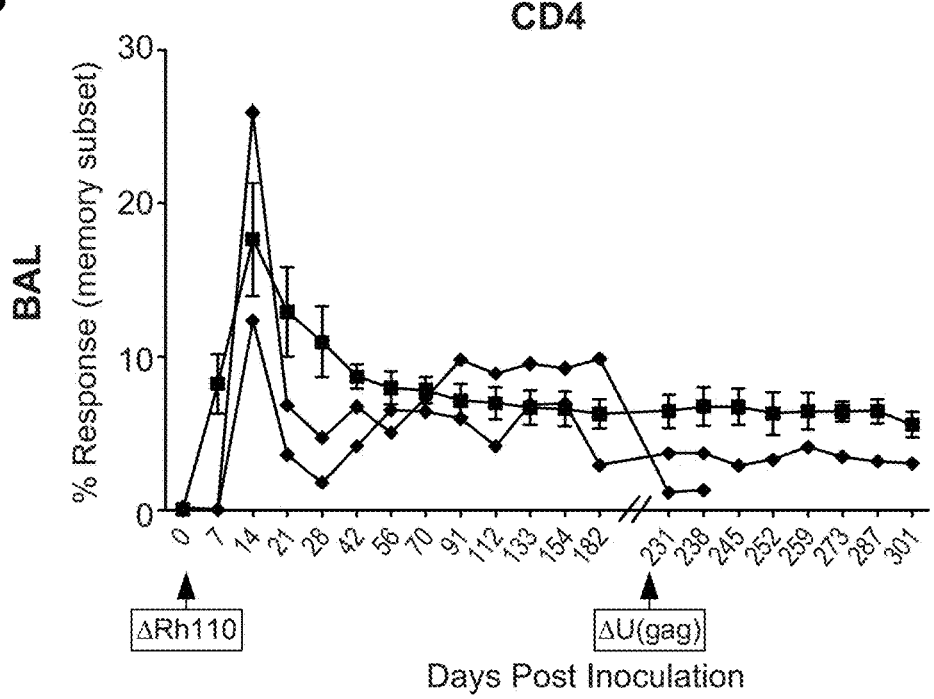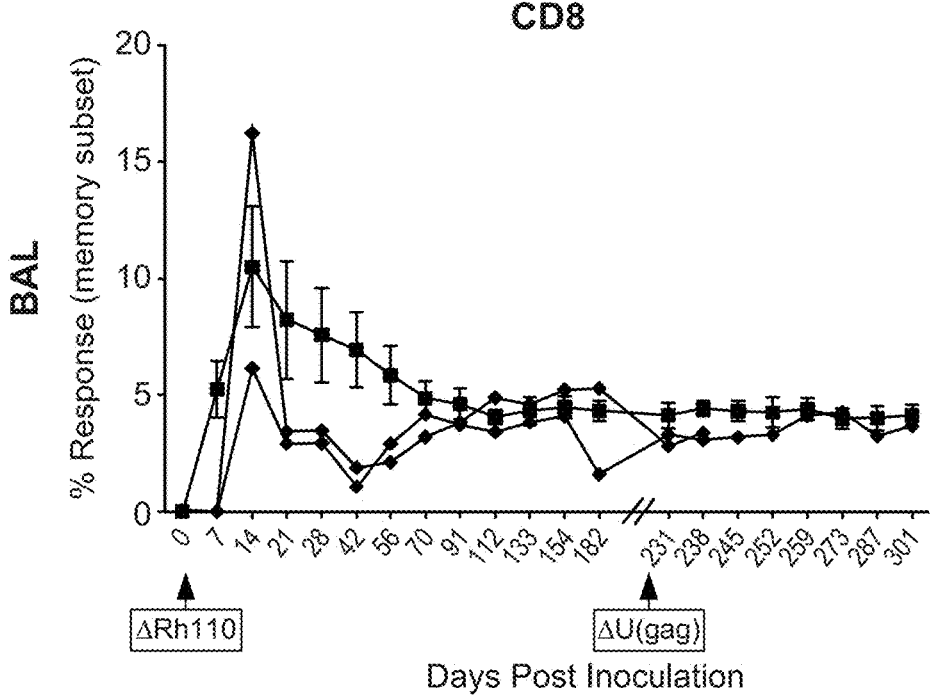
FIG. 23B

SEQUENCE LISTING

<160> NUMBER OF SEQ ID NOS: 44

<210> SEQ ID NO 1
<211> LENGTH: 60
<212> TYPE: DNA
<213> ORGANISM: Artificial Sequence
<220> FEATURE:
<223> OTHER INFORMATION: primer

<400> SEQUENCE: 1
taaaagtgtc ggatgaatgt gcggcgccaa cacgcagacc gaaaagtgcc acctgcagat    60

<210> SEQ ID NO 2
<211> LENGTH: 60
<212> TYPE: DNA
<213> ORGANISM: Artificial Sequence
<220> FEATURE:
<223> OTHER INFORMATION: primer

<400> SEQUENCE: 2
gcctgactga tgactagtca tcgcacgcct cttcccgccc caggaacact taacggctga    60

<210> SEQ ID NO 3

```
<211> LENGTH: 67
<212> TYPE: DNA
<213> ORGANISM: Artificial Sequence
<220> FEATURE:
<223> OTHER INFORMATION: primer

<400> SEQUENCE: 3
tttgttcgta taaaagtgtc ggatgaatgt gcggcgccaa cacgcagacc gtaaaacgac    60
ggccagt                                                              67

<210> SEQ ID NO 4
<211> LENGTH: 72
<212> TYPE: DNA
<213> ORGANISM: Artificial Sequence
<220> FEATURE:
<223> OTHER INFORMATION: primer

<400> SEQUENCE: 4
cgctccctcg gcctgactga tgactagtca tcgcacgcct cttcccgccc gtatgttgtg    60
tggaattgtg ag                                                        72

<210> SEQ ID NO 5
<211> LENGTH: 20
<212> TYPE: DNA
<213> ORGANISM: Artificial Sequence
<220> FEATURE:
<223> OTHER INFORMATION: SIVgag primer

<400> SEQUENCE: 5
acccacaacc agctccacaa                                                20

<210> SEQ ID NO 6
<211> LENGTH: 22
<212> TYPE: DNA
<213> ORGANISM: Artificial Sequence
<220> FEATURE:
<223> OTHER INFORMATION: SIVgag primer

<400> SEQUENCE: 6
atccactgga tctgttcgtc aa                                             22

<210> SEQ ID NO 7
<211> LENGTH: 23
<212> TYPE: DNA
<213> ORGANISM: Artificial Sequence
<220> FEATURE:
<223> OTHER INFORMATION: Rh156 primer

<400> SEQUENCE: 7
caatgaggat aggttcccag ttg                                            23

<210> SEQ ID NO 8
<211> LENGTH: 21
<212> TYPE: DNA
<213> ORGANISM: Artificial Sequence
<220> FEATURE:
<223> OTHER INFORMATION: Rh156 primer

<400> SEQUENCE: 8
gccagtggga tgtcagtacc a                                              21

<210> SEQ ID NO 9
<211> LENGTH: 20
<212> TYPE: DNA
<213> ORGANISM: Artificial Sequence
```

```
<220> FEATURE:
<223> OTHER INFORMATION: Rh175 primer

<400> SEQUENCE: 9
ctagcagtac tgagagctag                                                20

<210> SEQ ID NO 10
<211> LENGTH: 22
<212> TYPE: DNA
<213> ORGANISM: Artificial Sequence
<220> FEATURE:
<223> OTHER INFORMATION: Rh175 primer

<400> SEQUENCE: 10
tcacgccaat cgacagtgca cg                                             22

<210> SEQ ID NO 11
<211> LENGTH: 21
<212> TYPE: DNA
<213> ORGANISM: Artificial Sequence
<220> FEATURE:
<223> OTHER INFORMATION: Rh178 primer

<400> SEQUENCE: 11
cgcatactga caagccaggg c                                              21

<210> SEQ ID NO 12
<211> LENGTH: 21
<212> TYPE: DNA
<213> ORGANISM: Artificial Sequence
<220> FEATURE:
<223> OTHER INFORMATION: Rh178 primer

<400> SEQUENCE: 12
gcgaaagaag gtgcacatga c                                              21

<210> SEQ ID NO 13
<211> LENGTH: 22
<212> TYPE: DNA
<213> ORGANISM: Artificial Sequence
<220> FEATURE:
<223> OTHER INFORMATION: Rh181 primer

<400> SEQUENCE: 13
ccttacggag tcgctcgttg ac                                             22

<210> SEQ ID NO 14
<211> LENGTH: 22
<212> TYPE: DNA
<213> ORGANISM: Artificial Sequence
<220> FEATURE:
<223> OTHER INFORMATION: Rh181 primer

<400> SEQUENCE: 14
tgtgtcgtct ctttctccgc ag                                             22

<210> SEQ ID NO 15
<211> LENGTH: 23
<212> TYPE: DNA
<213> ORGANISM: Artificial Sequence
<220> FEATURE:
<223> OTHER INFORMATION: Rh182 primer

<400> SEQUENCE: 15
gattttcgtt gaacatgtcc gac                                            23
```

<210> SEQ ID NO 16
<211> LENGTH: 20
<212> TYPE: DNA
<213> ORGANISM: Artificial Sequence
<220> FEATURE:
<223> OTHER INFORMATION: Rh182 primer

<400> SEQUENCE: 16
gttatgtgtc agaaagtccg                                           20

<210> SEQ ID NO 17
<211> LENGTH: 19
<212> TYPE: DNA
<213> ORGANISM: Artificial Sequence
<220> FEATURE:
<223> OTHER INFORMATION: Rh189 primer

<400> SEQUENCE: 17
tgcttcgtcc tggtgctgt                                            19

<210> SEQ ID NO 18
<211> LENGTH: 21
<212> TYPE: DNA
<213> ORGANISM: Artificial Sequence
<220> FEATURE:
<223> OTHER INFORMATION: Rh189 primer

<400> SEQUENCE: 18
ttagcagttt catggttgcg a                                         21

<210> SEQ ID NO 19
<211> LENGTH: 21
<212> TYPE: DNA
<213> ORGANISM: Artificial Sequence
<220> FEATURE:
<223> OTHER INFORMATION: RH190 primer

<400> SEQUENCE: 19
gaaatggata gcggtgctca c                                         21

<210> SEQ ID NO 20
<211> LENGTH: 20
<212> TYPE: DNA
<213> ORGANISM: Artificial Sequence
<220> FEATURE:
<223> OTHER INFORMATION: Rh190 primer

<400> SEQUENCE: 20
cagacaacag gttgttcagg                                           20

<210> SEQ ID NO 21
<211> LENGTH: 21
<212> TYPE: DNA
<213> ORGANISM: Artificial Sequence
<220> FEATURE:
<223> OTHER INFORMATION: GAPDH primer

<400> SEQUENCE: 21
gcaccaccaa ctgcttagca c                                         21

<210> SEQ ID NO 22
<211> LENGTH: 20
<212> TYPE: DNA
<213> ORGANISM: Artificial Sequence
<220> FEATURE:
<223> OTHER INFORMATION: GAPDH primer

```
<400> SEQUENCE: 22
tcttctgggt ggcagtgatg                                              20

<210> SEQ ID NO 23
<211> LENGTH: 22
<212> TYPE: DNA
<213> ORGANISM: Artificial Sequence
<220> FEATURE:
<223> OTHER INFORMATION: Rh185 primer

<400> SEQUENCE: 23
agcgtagctc ctccataccg ct                                           22

<210> SEQ ID NO 24
<211> LENGTH: 21
<212> TYPE: DNA
<213> ORGANISM: Artificial Sequence
<220> FEATURE:
<223> OTHER INFORMATION: Rh185 primer

<400> SEQUENCE: 24
atccgcggac tgtttgggtg t                                            21

<210> SEQ ID NO 25
<211> LENGTH: 27
<212> TYPE: DNA
<213> ORGANISM: Artificial Sequence
<220> FEATURE:
<223> OTHER INFORMATION: Rh186 primer

<400> SEQUENCE: 25
gcttcttcca gaagttgcat aggatga                                      27

<210> SEQ ID NO 26
<211> LENGTH: 23
<212> TYPE: DNA
<213> ORGANISM: Artificial Sequence
<220> FEATURE:
<223> OTHER INFORMATION: Rh186 primer

<400> SEQUENCE: 26
cgactttccg gatcctacgt ggc                                          23

<210> SEQ ID NO 27
<211> LENGTH: 22
<212> TYPE: DNA
<213> ORGANISM: Artificial Sequence
<220> FEATURE:
<223> OTHER INFORMATION: Rh187 primer

<400> SEQUENCE: 27
ccatagccat gcaatggtcg ca                                           22

<210> SEQ ID NO 28
<211> LENGTH: 20
<212> TYPE: DNA
<213> ORGANISM: Artificial Sequence
<220> FEATURE:
<223> OTHER INFORMATION: Rh187 primer

<400> SEQUENCE: 28
gcgccatccc gtgttacccc                                              20

<210> SEQ ID NO 29
```

```
<211> LENGTH: 20
<212> TYPE: DNA
<213> ORGANISM: Artificial Sequence
<220> FEATURE:
<223> OTHER INFORMATION: Rh188 primer

<400> SEQUENCE: 29
agagctctgg tcgtcggcgt                                              20

<210> SEQ ID NO 30
<211> LENGTH: 22
<212> TYPE: DNA
<213> ORGANISM: Artificial Sequence
<220> FEATURE:
<223> OTHER INFORMATION: Rh188 primer

<400> SEQUENCE: 30
tggctggcca ccagatggat gt                                           22

<210> SEQ ID NO 31
<211> LENGTH: 20
<212> TYPE: DNA
<213> ORGANISM: Artificial Sequence
<220> FEATURE:
<223> OTHER INFORMATION: Rh189 primer

<400> SEQUENCE: 31
aaccagtagg agcgcccggt                                              20

<210> SEQ ID NO 32
<211> LENGTH: 24
<212> TYPE: DNA
<213> ORGANISM: Artificial Sequence
<220> FEATURE:
<223> OTHER INFORMATION: Rh189 primer

<400> SEQUENCE: 32
cgactcctgc atgcttactg ggga                                         24

<210> SEQ ID NO 33
<211> LENGTH: 25
<212> TYPE: DNA
<213> ORGANISM: Artificial Sequence
<220> FEATURE:
<223> OTHER INFORMATION: beta-actin primer

<400> SEQUENCE: 33
tcacccacac tgtgcccatc tacga                                        25

<210> SEQ ID NO 34
<211> LENGTH: 25
<212> TYPE: DNA
<213> ORGANISM: Artificial Sequence
<220> FEATURE:
<223> OTHER INFORMATION: beta-actin primer

<400> SEQUENCE: 34
cagcggaacc gctcattgcc aatgg                                        25

<210> SEQ ID NO 35
<211> LENGTH: 21
<212> TYPE: DNA
<213> ORGANISM: Artificial Sequence
<220> FEATURE:
<223> OTHER INFORMATION: Rh156 primer

<400> SEQUENCE: 35
```
gtttagggaa ccgccattct g            21

<210> SEQ ID NO 36
<211> LENGTH: 19
<212> TYPE: DNA
<213> ORGANISM: Artificial Sequence
<220> FEATURE:
<223> OTHER INFORMATION: Rh156 primer

<400> SEQUENCE: 36
gtatccgcgt tccaatgca            19

<210> SEQ ID NO 37
<211> LENGTH: 20
<212> TYPE: DNA
<213> ORGANISM: Artificial Sequence
<220> FEATURE:
<223> OTHER INFORMATION: SIVgag primer

<400> SEQUENCE: 37
acccacaacc agctccacaa            20

<210> SEQ ID NO 38
<211> LENGTH: 16
<212> TYPE: DNA
<213> ORGANISM: Artificial Sequence
<220> FEATURE:
<223> OTHER INFORMATION: SIVgag primer

<400> SEQUENCE: 38
ctgccattaa tctagc            16

<210> SEQ ID NO 39
<211> LENGTH: 19
<212> TYPE: DNA
<213> ORGANISM: Artificial Sequence
<220> FEATURE:
<223> OTHER INFORMATION: Rh189 primer

<400> SEQUENCE: 39
ctctggtcgt cggcgtatg            19

<210> SEQ ID NO 40
<211> LENGTH: 19
<212> TYPE: DNA
<213> ORGANISM: Artificial Sequence
<220> FEATURE:
<223> OTHER INFORMATION: Rh189 primer

<400> SEQUENCE: 40 tgcttcgtcct ggtgctgt            19

<210> SEQ ID NO 41
<211> LENGTH: 22
<212> TYPE: DNA
<213> ORGANISM: Artificial Sequence
<220> FEATURE:
<223> OTHER INFORMATION: Rh180 primer

<400> SEQUENCE: 41
ggcaagggag ctcaatggaa ac            22

<210> SEQ ID NO 42
<211> LENGTH: 20
<212> TYPE: DNA

```
<213> ORGANISM: Artificial Sequence
<220> FEATURE:
<223> OTHER INFORMATION: Rh180 primer

<400> SEQUENCE: 42
tcaacgccca tctaaagccg                                              20

<210> SEQ ID NO 43
<211> LENGTH: 20
<212> TYPE: DNA
<213> ORGANISM: Artificial Sequence
<220> FEATURE:
<223> OTHER INFORMATION: Rh178 primer

<400> SEQUENCE: 43
cgtttgcttc ctatgtccgc                                              20

<210> SEQ ID NO 44
<211> LENGTH: 20
<212> TYPE: DNA
<213> ORGANISM: Artificial Sequence
<220> FEATURE:
<223> OTHER INFORMATION: Rh178 primer

<400> SEQUENCE: 44
catttgcatg cagctgtgcg                                              20
```

CMV GLYCOPROTEINS AND RECOMBINANT VECTORS

RELATED APPLICATIONS AND INCORPORATION BY REFERENCE

This application is a continuation of U.S. non-provisional patent application Ser. No. 14/179,152, filed Feb. 12, 2014, now issued as U.S. Pat. No. 9,541,553, which is a continuation of U.S. non-provisional patent application Ser. No. 13/626,398 filed on Sep. 25, 2012, which is a continuation-in-part application of international patent application Serial No. PCT/US2011/029930 filed Mar. 25, 2011, which published as PCT Publication No. WO 2011/119920 on Sep. 29, 2011, which claims priority to U.S. provisional patent application Ser. No. 61/317,647 filed Mar. 25, 2010. Reference is made to U.S. patent application Ser. No. 11/597,457 filed Apr. 28, 2008.

FEDERAL FUNDING LEGEND

This invention was supported, in part, by the National Institutes of Health grant numbers RO1 AI059457 and RO1 AI060392), the National Center for Research Resources grant numbers RR016025, RR18107 and RR00163 supporting the Oregon National and the Ruth L. Kirschstein National Research Service Awards grant numbers T32 AI007472 and T32 HL007781. The federal government may have certain rights to this invention.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

REFERENCE TO SEQUENCE LISTING SUBMITTED ELECTRONICALLY

The instant application contains a Sequence Listing, which has been submitted in ASCII text file format via EFS-Web and is hereby incorporated by reference in its entirety. Said ASCII copy, created on Aug. 9, 2017, is named "065335-220123_Sequence_Listing," and is 12,288 bytes in size.

FIELD OF THE INVENTION

This invention relates to recombinant cytomegalovirus vectors, methods of making them, uses for them, expression products from them, and uses for the expression products. This invention also relates to cytomegalovirus glycoproteins US2, US3, US6 and US11, in particular recombinant cytomegalovirus vectors lacking one or more of the glycoproteins US2, US3, US6 and US11. This invention also relates to recombinant vectors expressing one or more of the glycoproteins US2, US3, US6 and US11 of HCMV and the homologous proteins Rh182, Rh184, Rh185 and Rh189 of RhCMV.

BACKGROUND OF THE INVENTION

HCMV is an ubiquitous virus that is present in over 60% of the population depending on socioeconomic status. Following primary infection, HCMV persists for the life span of the host. Although HCMV is generally benign in healthy individuals, the virus may cause devastating disease in immunocompromised populations resulting in high morbidity and mortality (for review, see (Pass, R. F. 2001. Cytomegalovirus, p. 2675-2705. In P. M. H. David M. Knipe, Diane E. Griffin, Robert A. Lamb Malcolm A. Martin, Bernard Roizman and Stephen E. Straus (ed.), Fields Virology, 4th ed. Lippincott Williams & Wilkins, Philadelphia)). Recent increases in the number of patients undergoing immunosuppressive therapy following solid organ (SOT) or allogeneic hematopoietic cell transplantation (HCT), as well as the expanded use of HCT for diseases such as sickle cell anemia, multiple sclerosis and solid cancers have increased the number of patient populations susceptible to HCMV disease (Chou, S. 1999. Transpl Infect Dis 1:105-14, Nichols, W. G., and M. Boeckh. 2000. J Clin Virol 16:25-40 and Sepkowitz, K. A. 2002. Clin Infect Dis 34:1098-107). HCMV is also the most common congenital viral infection, and the leading infectious cause of central nervous system maldevelopment in neonates (Fowler, K. B. et al. 1997. J Pediatr 130:624-30, Larke, R. P. et al. 1980. J Infect Dis 142:647-53 and Peckham, C. S. et al. 1983. Lancet 1:1352-5). In this regard, HCMV is considered the major cause of sensorineural deafness in neonates independent of infectious status (Fowler, K. B. et al. 1997. J Pediatr 130:624-30). HCMV therefore remains a major cause of mortality in multiple patient populations emphasizing the need for new antiviral pharmacologic and vaccine strategies. Immunity induced by natural wild-type (WT) CMV infection has consistently been shown unable to prevent CMV re-infection (see below). This unique characteristic of CMV presumably explains the poor efficacy of candidate vaccines in trials to prevent CMV infection (Pass, R. F. et al. 2009. N Engl J Med 360:1191-9). Nevertheless, immunity to HCMV acquired through natural infection has been shown to significantly decrease maternal to fetal transmission of HCMV during pregnancy. This observation would indicate that induction of an immunity in pregnant women that is comparable to that induced by natural CMV infection, but that is induced in a safe manner, may be able to decrease maternal to fetal transmission and have a significant impact on clinical CMV disease in the neonate. HCMV-specific T cell immunity has also been shown to afford protection against CMV disease in transplant patients, presenting another population wherein the ability to safely induce an immunity comparable to that acquired by natural CMV infection would have a clinical impact on CMV disease (Leen, A. M., and H. E. Heslop. 2008. Br J Haematol 143:169-79, Riddell, S. R., and P. D. Greenberg. 2000. J Antimicrob Chemother 45 Suppl T3:35-43 and Riddell, S. R. et al. 1994. Bone Marrow Transplantation 14:78-84). Cytomegalovirus is highly immunogenic, but has evolved immune evasion mechanisms to enable virus persistence and re-infection of the sero-positive host:

The immunological resources specifically devoted to controlling HCMV infection are enormous, with CMV being one of the most immunogenic viruses known. High antibody titers are directed against the main HCMV envelope glycoprotein (gB) during primary infection of healthy individuals (Alberola, J. et al. 2000. J Clin Virol 16:113-22 and Rasmussen, L. et al., 1991. J Infect Dis 164:835-42), and against multiple viral proteins (both structural and non-structural) during MCMV infection of mice (Farrell, H. E., and G. R. Shellam. 1989. J Gen Virol 70 (Pt 10):2573-86). A large proportion of the host T cell repertoire is also directed against CMV antigens, with 5-10 fold higher median CD4+ T cell response frequencies to HCMV than to acute viruses (measles, mumps, influenza, adenovirus) or even other persistent viruses such as herpes simplex and varicella-zoster viruses (Sylwester, A. W. et al. 2005. J Exp Med 202:673-85). A high frequency of CD8+ responses to defined HCMV epitopes or proteins is also commonly observed (Gillespie, G. M. et al. 2000. J Virol 74:8140-50, Kern, F. et al. 2002. J Infect Dis 185:1709-16, Kern, F. et al. 1999. Eur J Immunol 29:2908-15, Kern, F. et al. 1999. J Virol 73:8179-84 and Sylwester, A. W. et al. 2005. J Exp Med 202:673-85). In a large-scale human study quantifying CD4+ and CD8+ T cell responses to the entire HCMV genome, the mean frequencies of CMV-specific CD4+ and CD8+ T cells exceeded 10% of the memory population for both subsets (Sylwester, A. W. et al. 2005. J Exp Med 202:673-85). In this study, it was not unusual for CMV-specific T cells to account for >25% of the memory T cell repertoire of a specific individual or at specific tissue sites. The clinical importance of this high level of CMV-specific immunity is most clearly shown by the occurrence of multi-organ CMV disease in immune-suppressed individuals during transplantation, and the ability of adoptive transfer of T cells to protect these patients from CMV disease (Riddell, S. R. et al. 1994. Bone Marrow Transplantation 14:78-84).

Paradoxically, the high levels of CMV-specific immunity are unable to either eradicate the virus from the healthy infected individual, or confer protection of the CMV seropositive individual against re-infection. This ability of CMV to escape eradication by the immune system, and to re-infect the sero-positive host has long been believed to be linked to the multiple viral immunomodulators encoded by the virus (for review, see (Mocarski, E. S., Jr. 2002. Trends Microbiol 10:332-9)). The HCMV US6 family of proteins (RhCMV homologues: Rh182-Rh189) are the most extensively studied of these immunomodulators (Loenen, W. A. et al. 2001. Semin Immunol 13:41-9). At least four different genes, US2, US3, US6 and US11—and the respective RhCMV homologues (Rh182, Rh184, Rh185, and Rh189)—are known to interfere with assembly and transport of MHC I molecules (Ahn, K. et al. 1996. Proc Natl Acad Sci USA 93:10990-5, Ahn, K. et al. 1997. Immunity 6:613-21, Jones, T. R. et al. 1995. J Virol 69:4830-41, Pande, N. T. et al. 2005. J Virol 79:5786-98, Wiertz, E. J. et al. 1996. Cell 84:769-79 and Wiertz, E. J. et al. 1996. Nature 384:432-8). Each of these four molecules interferes at different essential points of MHC I protein maturation. Briefly, US2 binds to newly synthesized heavy chain (HC) and reverse translocates the protein through the translocation channel SEC61 back into the cytosol where HC is degraded by the proteasome (Wiertz, E. J. et al. 1996. Cell 84:769-79 and Wiertz, E. J. et al. 1996. Nature 384:432-8). Similarly, US11 ejects MHC I back out into the cytoplasm (Wiertz, E. J. et al. 1996. Cell 84:769-). US3 and US6 act later in the MHC-I assembly process (Ahn, K. et al. 1996. Proc Natl Acad Sci USA 93:10990-5 and Ahn, K. et al. 1997. Immunity 6:613-21), with US3 retaining fully formed heterotrimers in the ER thus preventing their transport to the cell surface (Ahn, K. et al. 1996. Proc Natl Acad Sci USA 93:10990-5 and Jones, T. R. et al. 1996. PNAS USA 93:11327-33), and US6 preventing peptide transport by TAP (and thus formation of the trimeric complex of HC, β2m and peptide) (Ahn, K. et al. 1997. Immunity 6:613-21, Hengel, H. et al. 1997. Immunity 6:623-32 and Lehner, P. J. et al. 1997. Proc Natl Acad Sci USA 94:6904-9).

Consistent with persistent replication/chronic reactivation within the host, CMV also induces and maintains a characteristic and unique T cell immune response. Memory T cells induced by vaccination or infection may be broadly characterized into either effector (TEM) or central (TCM) memory, which follow from the distinct functions of these two memory populations (Cheroutre, H., and L. Madakamutil. 2005. Cell Mol Life Sci 62:2853-66, Mackay, C. R. et al. 1990. J Exp Med 171:801-17, Masopust, D. et al. 2001. Science 291:2413-7, Sallusto, F. et al. 1999. Nature 401: 708-12 and Wherry, E. J. et al. 2003. Nat Immunol 4:225-34). TEM are designed for immediate function against the invading pathogen, being highly enriched at epithelial mucosal surfaces, are polyfunctional expressing high levels of multiple effector cytokines (expressing TNFα, IFNγ, MIP-1β effector molecules), and have high cytotoxic potential (CD8+). TEM and TCM may also be easily distinguished on the basis of cell surface markers, with TEM being CCR7−, CD28+/− and TCM being CCR7+, CD28+. Multiple studies indicate that persistently replicating viruses such as CMV maintain a T cell response that is heavily biased toward the TEM phenotype (Amyes, E. et al. 2003. J Exp Med 198:903-11, Appay, V., and S. Rowland-Jones. 2002. J Immunol Methods 268:9, Champagne, P. et al. 2001. Nature 410:106-11, Halwani, R. et al. 2006. Springer Semin Immunopathol 28:197-208 and Robinson, H. L., and R. R. Amara. 2005. Nat Med 11:S25-32). Indeed, CMV is regarded as the prototypic inducer of long-term TEM (Halwani, R. et al. 2006. Springer Semin Immunopathol 28:197-208, Holtappels, R. et al. 2000. Journal of Virology 74:11495-503, Robinson, H. L., and R. R. Amara. 2005. Nat Med 11:S25-32 and Sierro, S. et al. 2005. Eur J Immunol 35:1113-23). In contrast, analysis of T cell responses against non-persistent viruses (ie., influenza virus) in non-acutely infected humans, or following immunization with live non-persistent virus-based vaccines (YFV-17D, yellow fever vaccine, or Dryvax smallpox vaccine) shows that following a short-lived effector T cell phenotype, long-term virus-specific memory T cells against these non-persistent viruses is maintained primarily as TCM (Lucas, M. et al. 2004. J Virol 78:7284-7 and Miller, J. D. et al. 2008. Immunity 28:710-22).

Citation or identification of any document in this application is not an admission that such document is available as prior art to the present invention.

SUMMARY OF THE INVENTION

The present invention relates to relates to recombinant vectors, advantageously viral vectors that either express human cytomegalovirus (HCMV) glycoproteins US2, US3, US6 and US11 or rhesus cytomegalovirus (RCMV) glycoproteins Rh182, Rh184, Rh185 and Rh189. The invention also related to HCMV vectors that have HCMV glycoproteins US2, US3, US6 and US11 deleted therefrom.

Further objects of the invention include any or all of: to provide expression products from such recombinants, methods for expressing products from such recombinants, compositions containing the recombinants or the expression products, methods for using the expression products, methods for using the compositions, DNA from the recombinants, and methods for replicating DNA from the recombinants.

One embodiment of the invention relates to a method of superinfecting or repeatedly an animal (including human) which may comprise (a) constructing a vector containing and expressing at least one human cytomegalovirus (HCMV) glycoprotein, wherein the glycoprotein is US2, US3, US6 or US11 (or the corresponding RhCMV homologues), and (b) administering the vector into the animal, wherein the animal might have already been infected with the same vector.

The vector may be an adenovirus vector, adeno-associated virus (AAV) vector, alphavirus vector, herpesvirus vector (including HCMV), retrovirus vector and poxvirus vector. The vector may contain and express US2, US3, US6 and US11 or Rh182, Rh184, Rh185 and Rh189 or the vector may contain and express all of the glycoproteins within the US2 to US11 region of HCMV or the Rh182-189 region of RhCMV Another embodiment of the present invention relates to a method of determining efficacy of a HCMV vaccine, which may comprise (a) administering a HCMV vaccine to a test subject, (b) challenging the test subject with a HCMV vector, wherein glycoproteins within the US2 to US11 region of HCMV are deleted from the HCMV vector, and (c) measuring a protective CD8+ T cell response, wherein the HCMV vaccine is efficacious if a CD8+ T cell response protects against challenge with the HCMV vector with the glycoproteins within the US2 to US11 region of CMV deleted.

The US2-11 deleted HCMV vector maybe an HIV vaccine. Advantageously, the HIV antigen may be a HIV protein.

The US2-11 deleted HCMV vector may be a HCMV vaccine.

A further embodiment of the present invention relates to a method of inducing a different CD8+ T cell response in an animal or human, which may comprise (a) administering a HCMV vector with at least one cytomegalovirus (CMV) glycoprotein deleted from the CMV vector, wherein the glycoprotein is US2, US3, US6 or US11, and wherein the CMV vector contains and expresses at least one immunogen, and (b) administering the vector to the animal or human, wherein the CD8+ T cell response in the animal or human differs as compared to a CMV vector that contains and expresses the same at least one immunogen and wherein a CMV glycoprotein is not deleted from the CMV vector.

The vector may have CMV glycoproteins US2, US3, US6 and US11 deleted individually from the CMV vector. The vector may also have all of the glycoproteins within the US2 to US11 region of CMV deleted from the CMV vector.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The following detailed description, given by way of example, but not intended to limit the invention solely to the specific embodiments described, may best be understood in conjunction with the accompanying drawings.

FIG. 15. CD4+ T Cell-associated SIV in a protected RM.

FIG. 21. Antigen-specific response assays: routine staining panel.

FIG. 22. Deletion of the pp71-homologue Rh110 attenuates RhCMV in vitro. Reduced growth of RhCMV ΔRh110 and ΔRh110(retanef), but not control RhCMV WT virus on telomerized rhesus fibroblasts (tRF). Growth is rescued by growth in pp71-expressing complementing cells (tRFs+pp71 tet). Fibroblasts were infected with the indicated viruses at a multiplicity of infection (MOI) of 0.01. Culture supernatant was collected at the indicated days and the viral titer was determined on pp71-expressing complementing cells. Multi-step growth curves show replication deficiency of only ΔRh110 and ΔRh110(retanef), but not WT RhCMV on normal tRFs. Rescue of normal growth of ΔRh110 and ΔRh110(retanef) on pp71 complementing cells (cTRF/pp71) shows that growth deficiency is due to lack of pp71 expression.

FIG. 23A-23C. RhCMV ΔRh110 is attenuated in vivo and protects against challenge with ΔUS2-11(gag). Upper panels: Two sero-negative RM were inoculated s.c. with 107 PFU of RhCMV ΔRh110 at day 0. The CD8+ and CD4+ T cell response against RhCMV lysate was measured by ICCS in PBMC and BAL at the indicated intervals. At day 231, the ΔRh110-infected animals were challenged with 107 PFU of RhCMV ΔUS2-11(gag) (ΔUgag) and the T cell response against RhCMV lysate was measured at the indicated intervals. The absence of a T cell boost indicates that the animals were protected against ΔUS2-11 challenge. Lower panels: Detection of RhCMV in urine collected at the indicated days from two RM infected with RhCMV(gag) or two RM infected with ΔRh110. Expression of SIVgag, RhCMV IE or the cellular protein GAPDH (included as loading control) was determined from viral cocultures by immunoblot using specific antibodies (S. G. Hansen et al. Science 328, 5974 (2010)). The two animals infected with RhCMV(gag) secreted RhCMV (as shown by IE expression) because they were CMV-positive at the onset of the experiment. At day 56, these animals also secreted SIVgag expressing RhCMV indicating infection. In contrast, the two CMV-negative RM infected with ΔRh110 did not secrete RhCMV as indicated by the absence of IE-positive cocultures up to day 231. This result indicates that ΔRh110 is attenuated in vivo.

DETAILED DESCRIPTION OF THE INVENTION

Figure 1A:
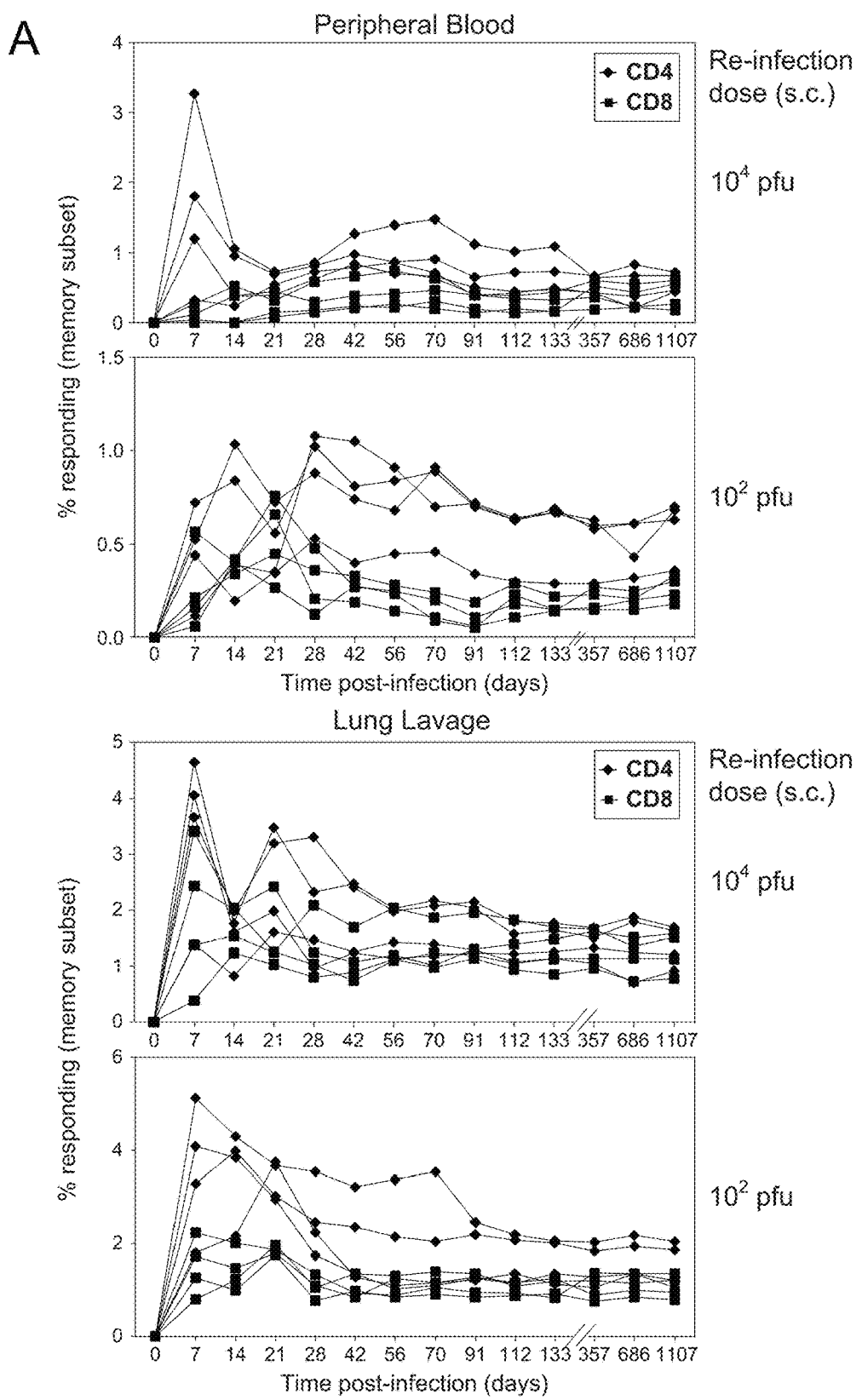
FIGS. 1A-1C. CMV-infected rhesus macaques are not protected against super-infection with RhCMV and super-infection of RhCMV-positive animals is independent of viral dose. (A) At day 0, two cohorts of four RhCMV+ animals each were infected subcutaneously with 102 or 104 PFU of RhCMV(gagL). The SIVgag-specific T cell responses in PBMC or in bronchoalveolar lavage (BAL) were monitored by flow cytometric analysis of intracellular cytokine staining (ICCS) for CD69 and tumor necrosis factor-$\alpha$ (TNF-$\alpha$) (S. G. Hansen et al. *Science* 328, 5974 (2010)) (see FIGS. 6 and 7). (B) Day of first detection of SIVgag-expressing virus in the urine or buccal swabs collected at the indicated intervals from each animal in the two cohorts shown in (A). Also included are results from a third cohort of eight RhCMV+ animals inoculated with 107 plaque forming units (PFU) of RhCMV(gagL). Expression of SIVgag was determined by immunoblot using antibody to SIVgag from viral cocultures (S. G. Hansen et al. Science 328, 5974 (2010)). Each circle represents an individual animal. (C) Long-term secretion of SIVgag-expressing virus. Urine was isolated at the indicated days post-infection (PID) from each of the RhCMV(gagL)-infected RM, and SIVgag expression was detected from cocultured virus by immunoblot. For control, a RhCMV-positive animal that did not receive RhCMV(gagL) was included.

The invention relates to a method of a vector capable of repeatedly infecting an organism which may comprise (a) constructing a vector containing and expressing at least one cytomegalovirus (CMV) glycoprotein, wherein the glycoprotein is US2, US3, US6 or US11, and (b) administering the vector repeatedly into the animal or human. Where superinfectivity is desired, any vector, advantageously a viral vector, may express one or more of the HCMV glycoproteins US2, US3, US6 and US11 (or the RhCMV homologues Rh182, Rh184, Rh185, Rh189). Viral expression vectors are well known to those skilled in the art and include, for example, viruses such as adenoviruses, adeno-associated viruses (AAV), alphaviruses, herpesviruses (including cytomegalovirus itself), retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and may be used as gene delivery vectors. Without US2-11 all of these vectors (except for CMV which contains US2-11 naturally) elicit vector-specific immunity which prohibits their repeated use.

In an embodiment where repeated infection of a vector is desired, any vector, advantageously a viral vector, may express one or more of the glycoproteins US2, US3, US6 and US11. In a particularly advantageous embodiment, the vector expresses glycoproteins US2, US3, US6 and US11. More advantageously, the vector contains and expresses all of the glycoproteins within the US2 to US11 region of CMV. In an advantageous embodiment, the one or more of the glycoproteins US2, US3, US6 and US11 may include, but not limited to, the glycoproteins of U.S. Pat. Nos. 7,892,564; 7,749,745; 7,364,893; 6,953,661; 6,913,751; 6,740,324; 6,613,892; 6,410,033; 6,140,114; 6,103,531; 6,033,671; 5,908,780; 5,906,935; 5,874,279; 5,853,733; 5,846,806; 5,843,458; 5,837,532; 5,804,372; 5,753,476; 5,741,696; 5,731,188; 5,720,957; 5,676,952; 5,599,544; 5,593,873 and 5,334,498.

In an embodiment where repeated infection of a vector is desired, any vector, advantageously a viral vector, may express one or more of the glycoproteins RhCMV homologues Rh182, Rh184, Rh185, Rh189. In a particularly advantageous embodiment, the vector expresses glycoproteins RhCMV homologues Rh182, Rh184, Rh185 and Rh189. In an advantageous embodiment, the one or more of the glycoproteins Rh182, Rh184, Rh185 and Rh189 may include, but not limited to, the glycoproteins of U.S. Pat. Nos. 7,635,485; 7,323,619; 6,964,762; 6,712,612; 6,544,780; 6,426,196; 6,391,632; 5,858,740; 5,834,256; 5,767,250 and 5,750,106.

The present invention also encompasses a method of determining efficacy of a CMV vaccine. Currently, efficacy of CMV vaccines are difficult to measure because CMV easily superinfects CMV-immune individuals. The invention may comprise (a) administering a CMV vaccine to a test subject, (b) challenging the test subject with a CMV vector, wherein glycoproteins within the US2 to US11 region of CMV are deleted from the CMV vector, and wherein the CMV vector contains and expresses at least one immunogen of the CMV vaccine, and (c) measuring a CD8+ T cell response, wherein the CMV vaccine is efficacious if a CD8+ T cell response is able to prevent infection with the CMV vector lacking the glycoproteins within the US2 to US11 region of CMV and wherein the CMV vector contains and expresses at least one immunogen of the CMV vaccine.

Applicants have infected rhesus macaques with RhCMV lacking the gene Rh110 that encodes for the viral transactivator pp71. RhCMVΔRh110 is growth-deficient in vitro and is attenuated in vitro since it is not secreted from infected monkeys (see FIG. 22). RhCMVΔRh1110 thus represents an example for an attenuated CMV vaccine. Applicants tested whether monkeys infected with RhCMVΔRh110 are protected against challenge with RhCMVΔUS2-11 expressing the SIV antigen Gag as immunological marker. Protection against infection with RhCMVΔUS2-11 was demonstrated by the absence of a boost in RhCMV-specific T cell responses and absence of a SIVgag-specific immune response. In contrast, monkeys infected with wildtype-virus typically show a boost of the CMV-specific T cell response and develop a de novo response to SIIVgag (see FIG. 43). This result indicates that spread-deficient, attenuated CMV is capable of inducing a T cell response that protects against challenge with US2-11 deleted virus. This result also indicates that a US2-11 deleted virus may be used to monitor the efficacy of the T cell response. Because of the similarities between RhCMV and HCMV, Applicants believe that a CMV-vector lacking pp71 may be used as a vaccine against CMV. Applicants further believe that a vaccine against HCMV may be validated by challenge with HCMV lacking US2-11.

Figure 24:
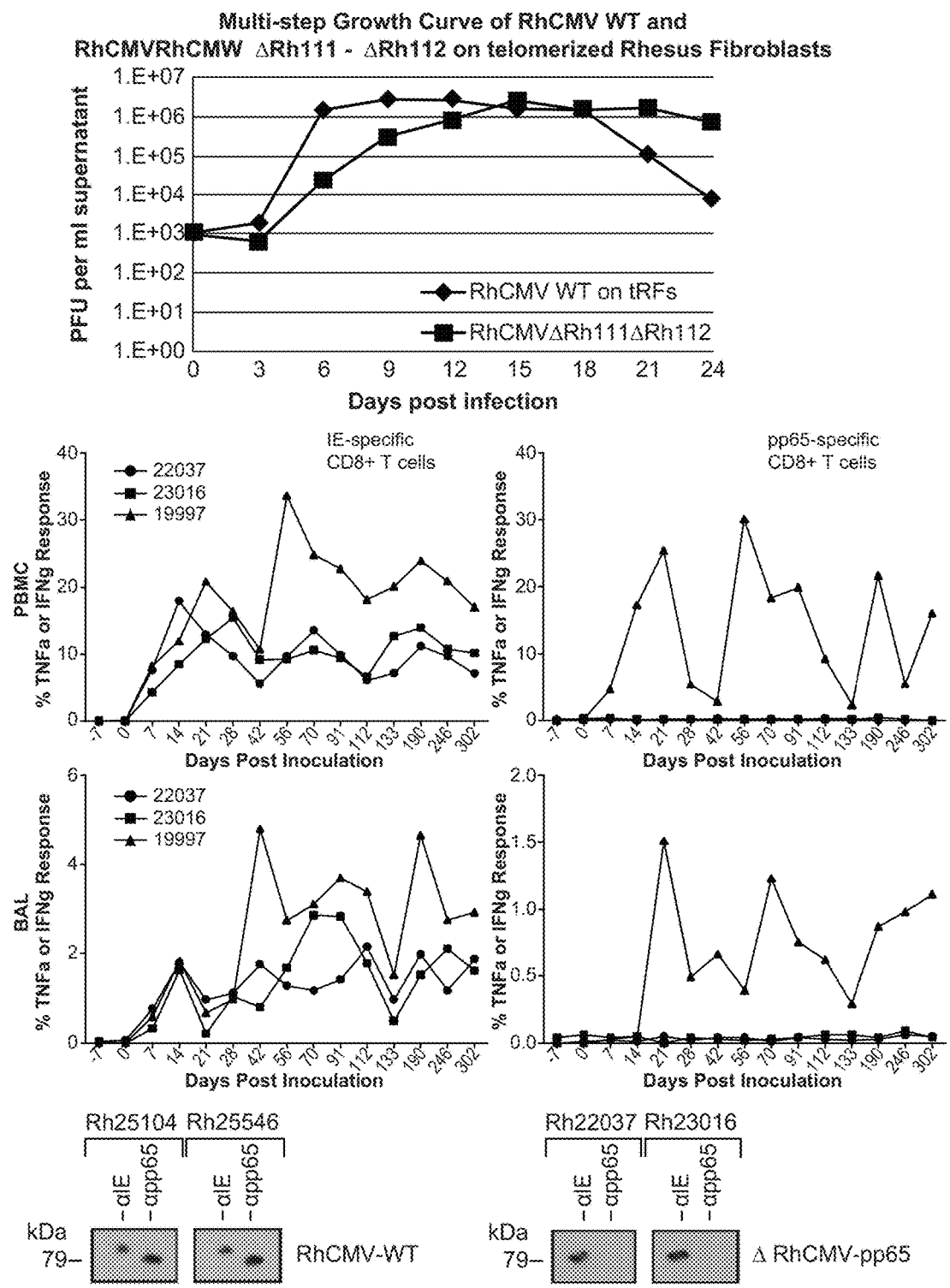
FIG. 24. RhCMV lacking the tegument proteins pp65a and pp65b (ΔRh111-112) encoded by the genes Rh111 and Rh112, respectively, was created. Upper panel: ΔRh111-112 grows like WT RhCMV in tissue culture. Telomerized rhesus fibroblasts (tRFs) were infected with the indicated viruses at a multiplicity of infection (MOI) of 0.01. Culture supernatant was collected at the indicated days and the viral titer was determined. Middle left panel: ΔRh110-112 induces an IE-specific, but not a pp65-specific T cell response. Two CMV-negative animals (lines with black squares and circles) were infected with 5×106 pfu ΔRh111-112 and one animal was infected with WT RhCMV (line with black triangles) at day 0. CD8+ T cell responses to CMV were measured by intracellular cytokine staining (TNFalpha and IFNgamma) in broncho-aveolar lavages (BAL, upper panels) or PBMC (lower panels) using overlapping peptides for RhCMV IE or RhCMV pp65. The panels show the % T cell reactive to each peptide pool. Lower panel: RhCMVΔRh111-112 is secreted from infected animals. Urine was collected at 56 days post-infection with WT RhCMV (animals 25104 and 25546) or ΔRh111-112 (animals 22037 and 23016). Expression of RhCMV IE or RhCMV pp65 was determined from viral cocultures by immunoblot using specific antibodies. All animals infected with WT and ΔRh111-112 secreted RhCMV as shown by IE expression. While the virus secreted from WT-infected animals also expressed pp65, this was not observed for ΔRh111-112 because this virus lacks the genes encoding pp65a and pp65b. This demonstrates that the secreted virus corresponds to ΔRh111-112 and that this virus is not attenuated in vivo.
Figure 25A:
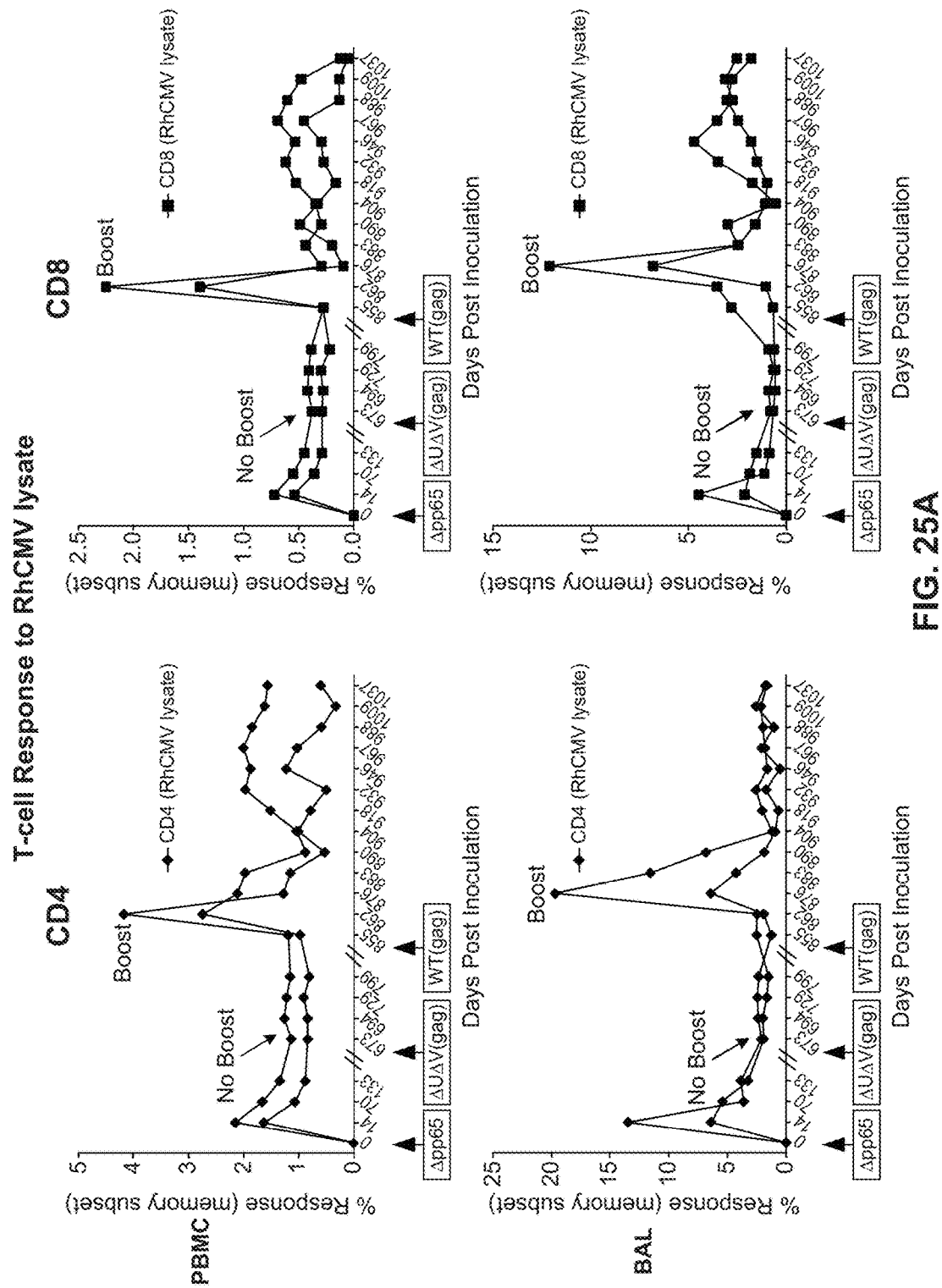
FIG. 25A-25B. RhCMV lacking pp65 protects against challenge with ΔUS2-11(gag). Two animals were infected with 5×106 pfu ΔRh111-112 and the T-cell response to SIV gag (overlapping 15 mers; 4 amino acid overlap) and T-cell response to RhCMV lysate was determined by ICCS at the indicated days. At day 673, animals were challenged by subcutaneous inoculation of 107 PFU of ΔUS2-11(gag) and the T cell response to RhCMV and SIVgag was measured. The absence of a boost in the RhCMV-specific T cell response and the absence of a de novo response to SIVgag indicates that both animals were protected against ΔUS2-11 (gag) challenge. This result indicates that pp65-deleted CMV induces long term protective T cell responses. At day 855, animals were challenged with US2-11 containing RhCMV(gag). Both animals displayed a boost in the CMV-specific T cell response and developed a de novo T cell response to SIVgag consistent with super-infection by RhCMV(gag). This result indicates that, similar to naturally infected animals, animals experimentally infected with replicating recombinant CMV vaccines are not protected against super-infection with US2-11 containing viruses.
Figure 25B:
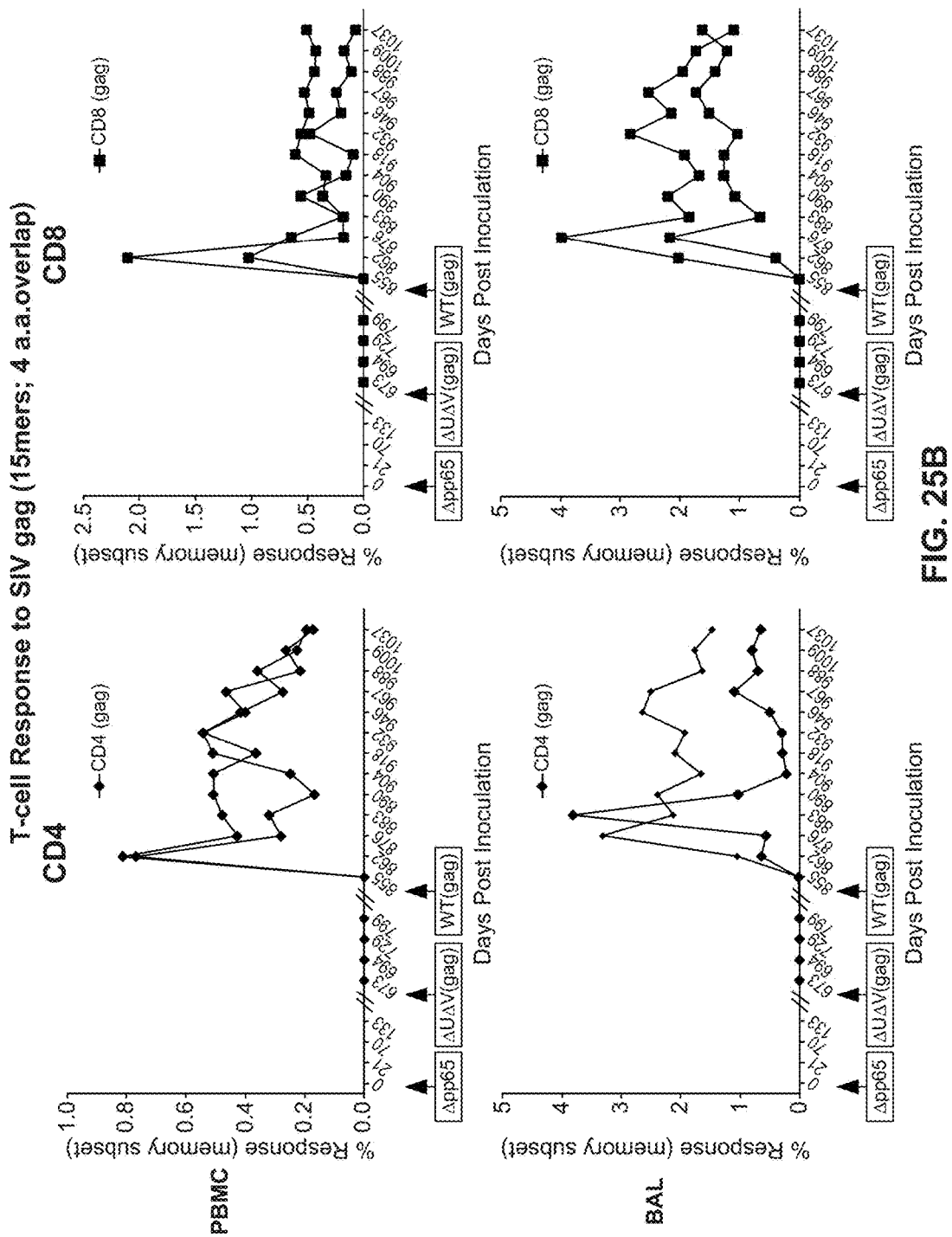

In a similar experiment Applicants created a RhCMV lacking the tegument proteins pp65a and pp65b encoded by the genes Rh111 and Rh112, respectively (see FIG. 24). These proteins are not required for viral growth in vitro or in vivo since Applicants observed that RhCMVΔRh111-112 is secreted from infected animals However, pp65 is an immunodominant protein that is included in current formulations of subunit vaccines for CMV developed by various investigators. To examine whether pp65-specific T cells are required for protection against challenge with ΔUS2-11, Applicants infected rhesus macaques with RhCMVΔRh111-112. As expected Applicants observed an immune response against the IE-proteins of CMV, but not against pp65. In contrast, a pp65-specific T cell response was readily detected in animals infected with RhCMV (blue line). Applicants tested whether monkeys infected with RhCMVΔRh111-2 are protected against challenge with RhCMVΔUS2-11 expressing the SIV antigen Gag as immunological marker. Protection against infection with RhCMVΔUS2-11 was demonstrated by the absence of a boost in RhCMV-specific T cell responses and absence of a SIVgag-specific immune response (see FIG. 25). In contrast, monkeys infected with wildtype-virus typically show a boost of the CMV-specific T cell response and develop a de novo response to SIVgag (see FIG. 25).

The present invention also relates to a method of inducing a different CD8+ T cell response in an animal, which may comprise (a) administering a CMV vector with at least one cytomegalovirus (CMV) glycoprotein deleted from the CMV vector, wherein the glycoprotein is US2, US3, US6 or US11, and wherein the CMV vector contains and expresses at least one immunogen, and (b) administering the vector to the animal or human, wherein the CD8+ T cell response in the animal or human differs as compared to a CMV vector that contains and expresses the same immunogen and wherein a CMV glycoprotein is not deleted from the CMV vector.

The present invention also relates to a method of inducing a different pathogen-specific CD8+ T cell response in an animal, which may comprise (a) administering a CMV vector with at least one cytomegalovirus (CMV) glycoprotein deleted from the CMV vector, wherein the glycoprotein is US2, US3, US6 or US11, and wherein the CMV vector contains and expresses at least one pathogen-derived immunogen, and (b) administering the vector to the animal, wherein the CD8+ T cell response in the animal differs as compared to a CMV vaccine with a CMV vector that contains and expresses the same immunogen and wherein a CMV glycoprotein is not deleted from the CMV vector.

Advantageously, the animal is a human.

The pathogen may be a viral pathogen and the immunogen may be a protein derived from the viral pathogen. Viruses include, but are not limited to Adenovirus, coxsackievirus, hepatitis A virus, poliovirus, rhinovirus, Herpes simplex, type 1, Herpes simplex, type 2, Varicella-zoster virus, Epstein-barr virus, Human cytomegalovirus, Human herpesvirus, type 8, Hepatitis B virus, Hepatitis C virus, yellow fever virus, dengue virus, West Nile virus, Human immunodeficiency virus (HIV), Influenza virus, Measles virus, Mumps virus, Parainfluenza virus, Respiratory syncytial virus, Human metapneumovirus, Human papillomavirus, Rabies virus, Rubella virus, Human bocavirus and Parvovirus B19.

The pathogen may be a bacterial pathogen and the immunogen may be a protein derived from the bacterial pathogen. The pathogenic bacteria include, but are not limited to, *Bordetella pertussis*, *Borrelia burgdorferi*, *Brucella abortus*, *Brucella canis*, *Brucella melitensis*, *Brucella suis*, *Campylobacter jejuni*, *Chlamydia pneumoniae*, *Chlamydia trachomatis*, *Chlamydophila psittaci*, *Clostridium botulinum*, *Clostridium difficile*, *Clostridium perfringens*, *Clostridium tetani*, *Corynebacterium diphtherias*, *Enterococcus faecalis*, *Enterococcus faecium*, *Escherichia coli*, *Francisella tularensis*, *Haemophilus influenzae*, *Helicobacter pylori*, *Legionella pneumophila*, *Leptospira interrogans*, *Listeria monocytogenes*, *Mycobacterium leprae*, *Mycobacterium tuberculosis*, *Mycobacterium ulcerans*, *Mycoplasma pneumoniae*, *Neisseria gonorrhoeae*, *Neisseria meningitidis*, *Pseudomonas aeruginosa*, *Rickettsia rickettsii*, *Salmonella typhi*, *Salmonella typhimurium*, *Shigella sonnei*, *Staphylococcus aureus*, *Staphylococcus epidermidis*, *Staphylococcus saprophyticus*, *Streptococcus agalactiae*, *Streptococcus pneumoniae*, *Streptococcus pyogenes*, *Treponema pallidum*, *Vibrio cholera* and *Yersinia pestis*.

The pathogen may be a parasite and the immunogen may be a protein derived from the parasite pathogen. The parasite may be a protozoan organism or disease caused by a protozoan organism such as, but not limited to, Acanthamoeba, Babesiosis, Balantidiasis, Blastocystosis, Coccidia, Dientamoebiasis, Amoebiasis, Giardia, Isosporiasis, Leishmaniasis, Primary amoebic meningoencephalitis (PAM), Malaria, Rhinosporidiosis, Toxoplasmosis—Parasitic pneumonia, Trichomoniasis, Sleeping sickness and Chagas disease. The parasite may be a helminth organism or worm or a disease caused by a helminth organism such as, but not limited to, Ancylostomiasis/Hookworm, Anisakiasis, Roundworm—Parasitic pneumonia, Roundworm—Baylisascariasis, Tapeworm—Tapeworm infection, Clonorchiasis, Dioctophyme renalis infection, Diphyllobothriasis—tapeworm, Guinea worm—Dracunculiasis, Echinococcosis—tapeworm, Pinworm—Enterobiasis, Liver fluke—Fasciolosis, Fasciolopsiasis—intestinal fluke, Gnathostomiasis, Hymenolepiasis, Loa loa filariasis, Calabar swellings, Mansonelliasis, Filariasis, Metagonimiasis—intestinal fluke, River blindness, Chinese Liver Fluke, Paragonimiasis, Lung Fluke, Schistosomiasis—bilharzia, bilharziosis or snail fever (all types), intestinal schistosomiasis, urinary schistosomiasis, Schistosomiasis by Schistosoma japonicum, Asian intestinal schistosomiasis, Sparganosis, Strongyloidiasis—Parasitic pneumonia, Beef tapeworm, Pork tapeworm, Toxocariasis, Trichinosis, Swimmer's itch, Whipworm and Elephantiasis Lymphatic filariasis. The parasite may be an organism or disease caused by an organism such as, but not limited to, parasitic worm, Halzoun Syndrome, Myiasis, Chigoe flea, Human Botfly and Candiru. The parasite may be an ectoparasite or disease caused by an ectoparasite such as, but not limited to, Bedbug, Head louse—Pediculosis, Body louse—Pediculosis, Crab louse—Pediculosis, Demodex—Demodicosis, Scabies, Screwworm and Cochliomyia.

The pathogen may be a cancer and the immunogen may be a protein derived from the cancer. The cancers, include, but are not limited to, Acute lymphoblastic leukemia; Acute myeloid leukemia; Adrenocortical carcinoma; AIDS-related cancers; AIDS-related lymphoma; Anal cancer; Appendix cancer; Astrocytoma, childhood cerebellar or cerebral; Basal cell carcinoma; Bile duct cancer, extrahepatic; Bladder cancer; Bone cancer, Osteosarcoma/Malignant fibrous histiocytoma; Brainstem glioma; Brain tumor; Brain tumor, cerebellar astrocytoma; Brain tumor, cerebral astrocytoma/ malignant glioma; Brain tumor, ependymoma; Brain tumor, medulloblastoma; Brain tumor, supratentorial primitive neuroectodermal tumors; Brain tumor, visual pathway and hypothalamic glioma; Breast cancer; Bronchial adenomas/ carcinoids; Burkitt lymphoma; Carcinoid tumor, childhood; Carcinoid tumor, gastrointestinal; Carcinoma of unknown primary; Central nervous system lymphoma, primary; Cerebellar astrocytoma, childhood; Cerebral astrocytoma/Malignant glioma, childhood; Cervical cancer; Childhood cancers; Chronic lymphocytic leukemia; Chronic myelogenous leukemia; Chronic myeloproliferative disorders; Colon Cancer; Cutaneous T-cell lymphoma; Desmoplastic small round cell tumor; Endometrial cancer; Ependymoma; Esophageal cancer; Ewing's sarcoma in the Ewing family of tumors; Extracranial germ cell tumor, Childhood; Extragonadal Germ cell tumor; Extrahepatic bile duct cancer; Eye Cancer, Intraocular melanoma; Eye Cancer, Retinoblastoma; Gallbladder cancer; Gastric (Stomach) cancer; Gastrointestinal Carcinoid Tumor; Gastrointestinal stromal tumor (GIST); Germ cell tumor: extracranial, extragonadal, or ovarian; Gestational trophoblastic tumor; Glioma of the brain stem; Glioma, Childhood Cerebral Astrocytoma; Glioma, Childhood Visual Pathway and Hypothalamic; Gastric carcinoid; Hairy cell leukemia; Head and neck cancer; Heart cancer; Hepatocellular (liver) cancer; Hodgkin lymphoma; Hypopharyngeal cancer; Hypothalamic and visual pathway glioma, childhood; Intraocular Melanoma; Islet Cell Carcinoma (Endocrine Pancreas); Kaposi sarcoma; Kidney cancer (renal cell cancer); Laryngeal Cancer; Leukemias; Leukemia, acute lymphoblastic (also called acute lymphocytic leukemia); Leukemia, acute myeloid (also called acute myelogenous leukemia); Leukemia, chronic lymphocytic (also called chronic lymphocytic leukemia); Leukemia, chronic myelogenous (also called chronic myeloid leukemia); Leukemia, hairy cell; Lip and Oral Cavity Cancer; Liver Cancer (Primary); Lung Cancer, Non-Small Cell; Lung Cancer, Small Cell; Lymphomas; Lymphoma, AIDS-related; Lymphoma, Burkitt; Lymphoma, cutaneous T-Cell; Lymphoma, Hodgkin; Lymphomas, Non-Hodgkin (an old classification of all lymphomas except Hodgkin's); Lymphoma, Primary Central Nervous System; Marcus Whittle, Deadly Disease; Macroglobulinemia, Waldenström; Malignant Fibrous Histiocytoma of Bone/Osteosarcoma; Medulloblastoma, Childhood; Melanoma; Melanoma, Intraocular (Eye); Merkel Cell Carcinoma; Mesothelioma, Adult Malignant; Mesothelioma, Childhood; Metastatic Squamous Neck Cancer with Occult Primary; Mouth Cancer; Multiple Endocrine Neoplasia Syndrome, Childhood; Multiple Myeloma/Plasma Cell Neoplasm; Mycosis Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple (Cancer of the Bone-Marrow); Myeloproliferative Disorders, Chronic; Nasal cavity and paranasal sinus cancer; Nasopharyngeal carcinoma; Neuroblastoma; Non-Hodgkin lymphoma; Non-small cell lung cancer; Oral Cancer; Oropharyngeal cancer; Osteosarcoma/malignant fibrous histiocytoma of bone; Ovarian cancer; Ovarian epithelial cancer (Surface epithelial-stromal tumor); Ovarian germ cell tumor; Ovarian low malignant potential tumor; Pancreatic cancer; Pancreatic cancer, islet cell; Paranasal sinus and nasal cavity cancer; Parathyroid cancer; Penile cancer; Pharyngeal cancer; Pheochromocytoma; Pineal astrocytoma; Pineal germinoma; Pineoblastoma and supratentorial primitive neuroectodermal tumors, childhood; Pituitary adenoma; Plasma cell neoplasia/Multiple myeloma; Pleuropulmonary blastoma; Primary central nervous system lymphoma; Prostate cancer; Rectal cancer; Renal cell carcinoma (kidney cancer); Renal pelvis and ureter, transitional cell cancer; Retinoblastoma; Rhabdomyosarcoma, childhood; Salivary gland cancer; Sarcoma, Ewing family of tumors; Sarcoma, Kaposi; Sarcoma, soft tissue; Sarcoma, uterine; Sézary syndrome; Skin cancer (nonmelanoma); Skin cancer (melanoma); Skin carcinoma, Merkel cell; Small cell lung cancer; Small intestine cancer; Soft tissue sarcoma; Squamous cell carcinoma—see Skin cancer (nonmelanoma); Squamous neck cancer with occult primary, metastatic; Stomach cancer; Supratentorial primitive neuroectodermal tumor, childhood; T-Cell lymphoma, cutaneous (Mycosis Fungoides and Sézary syndrome); Testicular cancer; Throat cancer; Thymoma, childhood; Thymoma and Thymic carcinoma; Thyroid cancer; Thyroid cancer, childhood; Transitional cell cancer of the renal pelvis and ureter; Trophoblastic tumor, gestational; Unknown primary site, carcinoma of, adult; Unknown primary site, cancer of, childhood; Ureter and renal pelvis, transitional cell cancer; Urethral cancer; Uterine cancer, endometrial; Uterine sarcoma; Vaginal cancer; Visual pathway and hypothalamic glioma, childhood; Vulvar cancer; Waldenström macroglobulinemia and Wilms tumor (kidney cancer), childhood.

Figure 19:
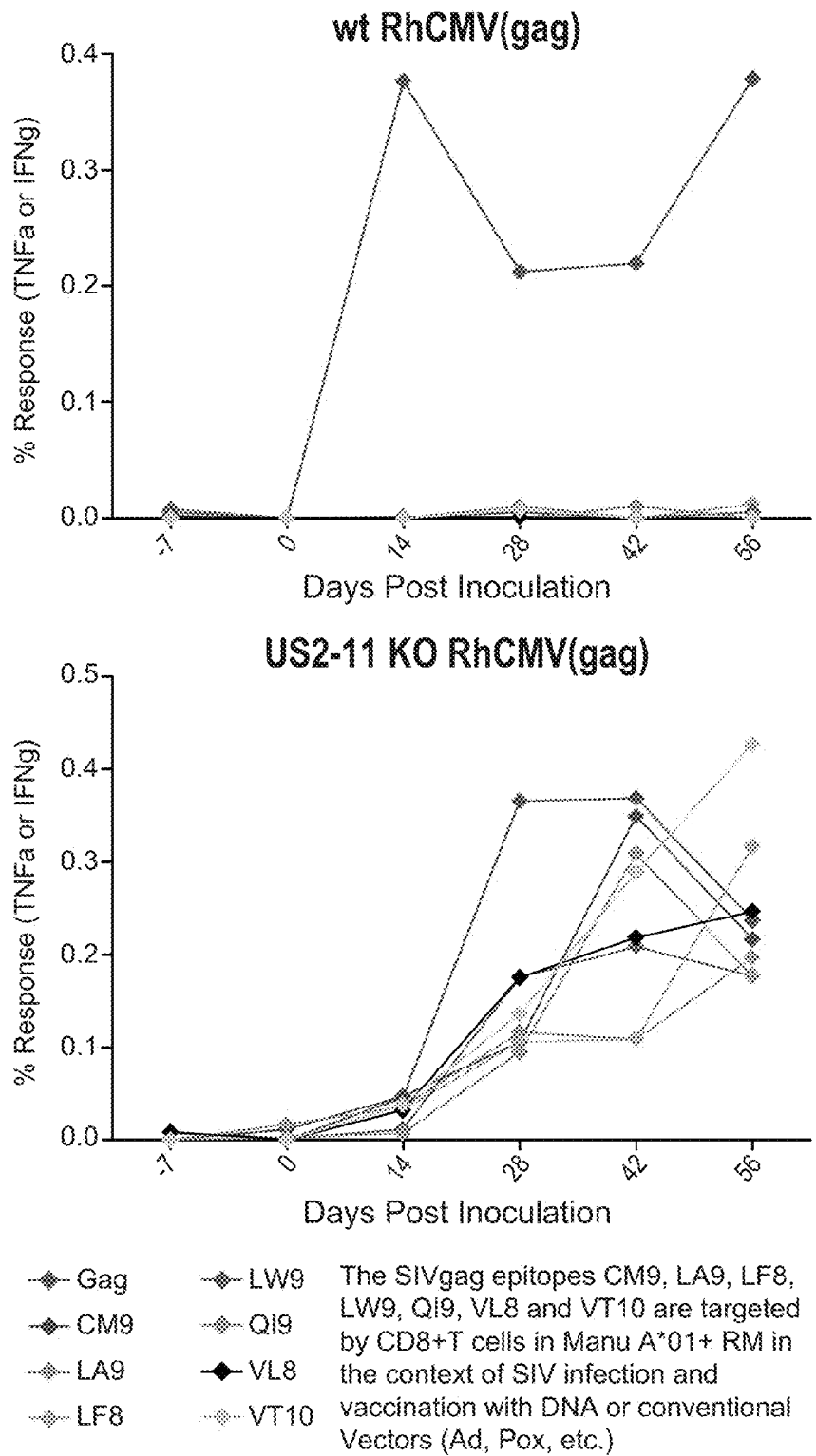
FIG. 19. Comparison of CD8+ T cell epitope targeting of SIVgag-specific responses arising after vaccination of Mamu A*01+, CMV-naïve RM with wt RhCMV(gag) vs. ΔUS2-11(gag) (US2-11 KO RhCMV(gag)) vectors. The US2-11 KO vector elicits responses to all previously characterized Mamu A*01-restricted gag epitopes, whereas wt CMV vectors elicit gag-specific CD8+ T cell responses that do not target these epitopes (gag=total gag 15mer mixes).
Figure 20:
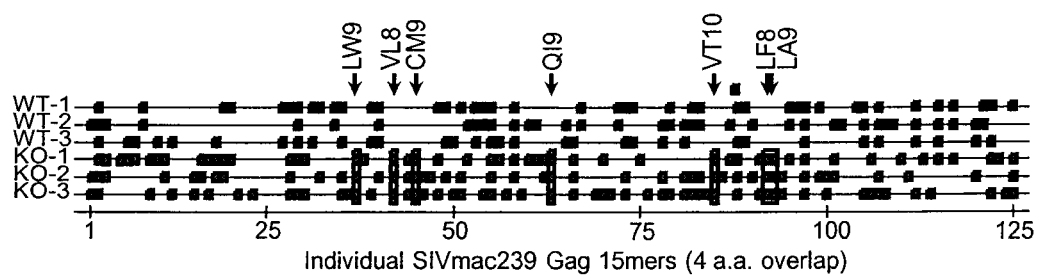
FIG. 20. Recognition of individual, consecutive gag 15mer peptides by 3 each Mamu A*01+, CMV-naïve RM vaccinated with RhCMV(gag) (WT) vs. ΔUS2-11(gag) (KO) vectors. Note that whereas both wt and KO vectors elicit diverse CD8+ T cell recognition of gag epitopes, only the KO vector-elicited responses include recognition of peptides containing conventional immunodominant epitopes (yellow rectangles; epitopes designated at top).

Applicants demonstrate that US2-11 deleted vector may induce a qualitatively different immune response to a heterologous antigen as compared to a recombinant wildtype virus (see FIGS. 19 and 20). Applicants inoculate animals carrying different US2-11 deleted vectors expressing antigens from SIV and examining T cell responses SIV antigens such as gag, retanef, env and pol, which are used to vaccinate CMV-naïve rhesus macaques (RMs) against SIV. The T cell response is determined as indicated below.

It is an object of the invention to provide a recombinant cytomegalovirus (CMV).

It is a further object of the invention to provide such a recombinant which contains exogenous DNA, preferably in a non-essential region, and which has had one or more glycoproteins US2, US3, US6 and US11, deleted therefrom.

It is also an object of the invention to provide such a recombinant CMV containing exogenous DNA.

Further objects of the invention include any or all of: to provide expression products from such recombinants, methods for expressing products from such recombinants, compositions containing the recombinants or the expression products, methods for using the expression products, methods for using the compositions, DNA from the recombinants, and methods for replicating DNA from the recombinants.

Accordingly, the invention provides a CMV synthetically modified to contain therein exogenous DNA. The CMV advantageously has had one or more glycoproteins US2, US3, US6 and US11, deleted therefrom.

The invention also pertains to any viral vector that contains and expresses one or more CMV glycoproteins US2, US3, US6 and US11.

The invention further provides a vector for cloning or expression of heterologous DNA which may comprise the recombinant CMV.

The heterologous DNA encodes an expression product which may comprise: an epitope of interest, a biological response modulator, a growth factor, a recognition sequence, a therapeutic gene, or a fusion protein.

An epitope of interest is an antigen or immunogen or immunologically active fragment thereof from a pathogen or toxin of veterinary or human interest.

An epitope of interest may be an antigen of pathogen or toxin, or from an antigen of a pathogen or toxin, or another antigen or toxin which elicits a response with respect to the pathogen, of from another antigen or toxin which elicits a response with respect to the pathogen.

An epitope of interest may be an antigen of a human pathogen or toxin, or from an antigen of a human pathogen or toxin, or another antigen or toxin which elicits a response with respect to the pathogen, or from another antigen or toxin which elicits a response with respect to the pathogen, such as, for instance: a Morbillivirus antigen, e.g., a measles virus antigen such as HA or F; a rabies glycoprotein, e.g., rabies virus glycoprotein G; an influenza antigen, e.g., influenza virus HA or N; a Herpesvirus antigen, e.g., a glycoprotein of a herpes simplex virus (HSV), a human cytomegalovirus (HCMV), Epstein-Barr; a flavivirus antigen, a JEV, Yellow Fever virus or Dengue virus antigen; a Hepatitis virus antigen, e.g., HBsAg; an immunodeficiency virus antigen, e.g., an HIV antigen such as gp120, gp160; a Hantaan virus antigen; a *C. tetani* antigen; a mumps antigen; a pneumococcal antigen, e.g., PspA; a *Borrelia* antigen, e.g., OspA, OspB, OspC of *Borrelia* associated with Lyme disease such as *Borrelia burgdoreferi, Borrelia atzelli* and *Borrelia garinii*; a chicken pox (varicella zoster) antigen; or a *Plasmodium* antigen.

Advantageously, the epitope of interest is an immunodeficiency antigen, advantageously HIV or SIV.

Of course, the foregoing lists are intended as exemplary, as the epitope of interest may be an antigen of any veterinary or human pathogen or from any antigen of any veterinary or human pathogen.

Since the heterologous DNA may be a growth factor or therapeutic gene, the recombinant CMV may be used in gene therapy. Gene therapy involves transferring genetic information; and, with respect to gene therapy and immunotherapy, reference is made to U.S. Pat. No. 5,252,479, which is incorporated herein by reference, together with the documents cited in it and on its face, and to WO 94/16716 and U.S. application Ser. No. 08/184,009, filed Jan. 19, 1994, each of which is also incorporated herein by reference, together with the documents cited therein. The growth factor or therapeutic gene, for example, may encode a disease-fighting protein, a molecule for treating cancer, a tumor suppressor, a cytokine, a tumor associated antigen, or interferon; and, the growth factor or therapeutic gene may, for example, be selected from the group consisting of a gene encoding alpha-globin, beta-globin, gamma-globin, granulocyte macrophage-colony stimulating factor, tumor necrosis factor, an interleukin, macrophage colony stimulating factor, granulocyte colony stimulating factor, erythropoietin, mast cell growth factor, tumor suppressor p53, retinoblastoma, interferon, melanoma associated antigen or B7.

The invention still further provides an immunogenic, immunological or vaccine composition containing the recombinant CMV virus or vector, and a pharmaceutically acceptable carrier or diluent. An immunological composition containing the recombinant CMV virus or vector (or an expression product thereof) elicits an immunological response—local or systemic. The response may, but need not be, protective. An immunogenic composition containing the recombinant CMV virus or vector (or an expression product thereof) likewise elicits a local or systemic immunological response which may, but need not be, protective. A vaccine composition elicits a local or systemic protective response. Accordingly, the terms "immunological composition" and "immunogenic composition" include a "vaccine composition" (as the two former terms may be protective compositions).

The invention therefore also provides a method of inducing an immunological response in a host vertebrate which may comprise administering to the host an immunogenic, immunological or vaccine composition which may comprise the recombinant CMV virus or vector and a pharmaceutically acceptable carrier or diluent. For purposes of this specification, "animal" includes all vertebrate species, except humans; and "vertebrate" includes all vertebrates, including animals (as "animal" is used herein) and humans. And, of course, a subset of "animal" is "mammal", which for purposes of this specification includes all mammals, except humans.

The invention even further provides a therapeutic composition containing the recombinant CMV virus or vector and a pharmaceutically acceptable carrier or diluent. The therapeutic composition is useful in the gene therapy and immunotherapy embodiments of the invention, e.g., in a method for transferring genetic information to an animal or human in need of such which may comprise administering to the host the composition; and, the invention accordingly includes methods for transferring genetic information.

In yet another embodiment, the invention provides a method of expressing a protein or gene product or an expression product which may comprise infecting or transfecting a cell in vitro with a recombinant CMV virus or vector of the invention and optionally extracting, purifying or isolating the protein, gene product or expression product or DNA from the cell. And, the invention provides a method for cloning or replicating a heterologous DNA sequence which may comprise infecting or transfecting a cell in vitro or in vivo with a recombinant CMV virus or vector of the invention and optionally extracting, purifying or isolating the DNA from the cell or progeny virus The invention in another aspect provides a method for preparing the recombinant CMV virus or vector of the invention which may comprise inserting the exogenous DNA into a non-essential region of the CMV genome.

The method may further comprise deleting a non-essential region from the CMV genome, preferably prior to inserting the exogenous DNA.

The method may comprise in vivo recombination. Thus, the method may comprise transfecting a cell with CMV DNA in a cell-compatible medium in the presence of donor DNA which may comprise the exogenous DNA flanked by DNA sequences homologous with portions of the CMV genome, whereby the exogenous DNA is introduced into the genome of the CMV, and optionally then recovering CMV modified by the in vivo recombination.

The method may also comprise cleaving CMV DNA to obtain cleaved CMV DNA, ligating the exogenous DNA to the cleaved CMV DNA to obtain hybrid CMV-exogenous DNA, transfecting a cell with the hybrid CMV-exogenous DNA, and optionally then recovering CMV modified by the presence of the exogenous DNA.

Since in vivo recombination is comprehended, the invention accordingly also provides a plasmid which may comprise donor DNA not naturally occurring in CMV encoding a polypeptide foreign to CMV, the donor DNA is within a segment of CMV DNA which would otherwise be co-linear with a non-essential region of the CMV genome such that DNA from a non-essential region of CMV is flanking the donor DNA.

The exogenous DNA may be inserted into CMV to generate the recombinant CMV in any orientation which yields stable integration of that DNA, and expression thereof, when desired.

The exogenous DNA in the recombinant CMV virus or vector of the invention may include a promoter. The promoter may be from a herpesvirus. For instance, the promoter may be a cytomegalovirus (CMV) promoter, such as a human CMV (HCMV) or murine CMV promoter.

The promoter may be a truncated transcriptionally active promoter which may comprise a region transactivated with a transactivating protein provided by the virus and the minimal promoter region of the full-length promoter from which the truncated transcriptionally active promoter is derived. For purposes of this specification, a "promoter" is composed of an association of DNA sequences corresponding to the minimal promoter and upstream regulatory sequences; a "minimal promoter" is composed of the CAP site plus TATA box (minimum sequences for basic level of transcription; unregulated level of transcription); and, "upstream regulatory sequences" are composed of the upstream element(s) and enhancer sequence(s). Further, the term "truncated" indicates that the full-length promoter is not completely present, i.e., that some portion of the full-length promoter has been removed. And, the truncated promoter may be derived from a herpesvirus such as MCMV or HCMV, e.g., HCMV-IE or MCMV-IE.

Like the aforementioned promoter, the inventive promoter is preferably a herpesvirus, e.g., a MCMV or HCMV such as MCMV-IE or HCMV-IE promoter; and, there may be up to a 40% and even up to a 90% reduction in size, from a full-length promoter, based upon base pairs.

The invention thus also provides an expression cassette for insertion into a recombinant virus or plasmid which may comprise the truncated transcriptionally active promoter. The expression cassette may further include a functional truncated polyadenylation signal; for instance an SV40 polyadenylation signal which is truncated, yet functional. Considering that nature provided a larger signal, it is indeed surprising that a truncated polyadenylation signal is functional; and, a truncated polyadenylation signal addresses the insert size limit problems of recombinant viruses such as CMV. The expression cassette may also include exogenous or heterologous DNA with respect to the virus or system into which it is inserted; and that DNA may be exogenous or heterologous DNA as described herein.

In a more specific aspect, the present invention encompasses CMV, recombinants which may comprise the HCMV-IE or MCMV-IE promoter, preferably a truncated promoter therefrom. Preferably, the HCMV-IE or MCMV-IE promoter or a truncated promoter therefrom is transactivated by CMV-induced gene products.

The invention further comprehends antibodies elicited by the inventive compositions and/or recombinants and uses for such antibodies. The antibodies, or the product (epitopes of interest) which elicited them, or monoclonal antibodies from the antibodies, may be used in binding assays, tests or kits to determine the presence or absence of an antigen or antibody.

Flanking DNA used in the invention may be from the site of insertion or a portion of the genome adjacent thereto (wherein "adjacent" includes contiguous sequences, e.g., codon or codons, as well as up to as many sequences, e.g., codon or codons, before there is an intervening insertion site).

The exogenous or heterologous DNA (or DNA foreign to CMV, or DNA not naturally occurring in CMV) may be DNA encoding any of the aforementioned epitopes of interest, as listed above. The exogenous DNA may include a marker, e.g., a color or light marker. The exogenous DNA may also code for a product which would be detrimental to an insect host such that the expression product may be a pesticide or insecticide. The exogenous DNA may also code for an anti-fungal polypeptide; and, for information on such a polypeptide and DNA therefor, reference is made to U.S. Pat. No. 5,421,839 and the documents cited therein, incorporated herein by reference.

The heterologous or exogenous DNA in recombinants of the invention preferably encodes an expression product which may comprise: an epitope of interest, a biological response modulator, a growth factor, a recognition sequence, a therapeutic gene, or a fusion protein. With respect to these terms, reference is made to the following discussion, and generally to Kendrew, THE ENCYCLOPEDIA OF MOLECULAR BIOLOGY (Blackwell Science Ltd 1995) and Sambrook, Fritsch, Maniatis, Molecular Cloning, A LABORATORY MANUAL (2d Edition, Cold Spring Harbor Laboratory Press, 1989).

As to antigens for use in vaccine or immunological compositions, see also Stedman's Medical Dictionary (24th edition, 1982, e.g., definition of vaccine (for a list of antigens used in vaccine formulations; such antigens or epitopes of interest from those antigens may be used in the invention, as either an expression product of the inventive recombinant virus, or in a multivalent composition containing an inventive recombinant virus or an expression product therefrom).

As to epitopes of interest, one skilled in the art may determine an epitope or immunodominant region of a peptide or polypeptide and ergo the coding DNA therefor from the knowledge of the amino acid and corresponding DNA sequences of the peptide or polypeptide, as well as from the nature of particular amino acids (e.g., size, charge, etc.) and the codon dictionary, without undue experimentation.

A general method for determining which portions of a protein to use in an immunological composition focuses on the size and sequence of the antigen of interest. "In general, large proteins, because they have more potential determinants are better antigens than small ones. The more foreign an antigen, that is the less similar to self configurations which induce tolerance, the more effective it is in provoking an immune response." Ivan Roitt, Essential Immunology, 1988.

As to size: the skilled artisan may maximize the size of the protein encoded by the DNA sequence to be inserted into the viral vector (keeping in mind the packaging limitations of the vector). To minimize the DNA inserted while maximizing the size of the protein expressed, the DNA sequence may exclude introns (regions of a gene which are transcribed but which are subsequently excised from the primary RNA transcript).

At a minimum, the DNA sequence may code for a peptide at least 8 or 9 amino acids long. This is the minimum length that a peptide needs to be in order to stimulate a CD4+ T cell response (which recognizes virus infected cells or cancerous cells). A minimum peptide length of 13 to 25 amino acids is useful to stimulate a CD8+ T cell response (which recognizes special antigen presenting cells which have engulfed the pathogen). See Kendrew, supra. However, as these are minimum lengths, these peptides are likely to generate an immunological response, i.e., an antibody or T cell response; but, for a protective response (as from a vaccine composition), a longer peptide is preferred.

With respect to the sequence, the DNA sequence preferably encodes at least regions of the peptide that generate an antibody response or a T cell response. One method to determine T and B cell epitopes involves epitope mapping. The protein of interest "is fragmented into overlapping peptides with proteolytic enzymes. The individual peptides are then tested for their ability to bind to an antibody elicited by the native protein or to induce T cell or B cell activation. This approach has been particularly useful in mapping T-cell epitopes since the T cell recognizes short linear peptides complexed with MHC molecules (see FIG. 20). The method is less effective for determining B-cell epitopes" since B cell epitopes are often not linear amino acid sequence but rather result from the tertiary structure of the folded three dimensional protein. Janis Kuby, Immunology, (1992) pp. 79-80.

Another method for determining an epitope of interest is to choose the regions of the protein that are hydrophilic. Hydrophilic residues are often on the surface of the protein and are therefore often the regions of the protein which are accessible to the antibody. Janis Kuby, Immunology, (1992) p. 81.

Yet another method for determining an epitope of interest is to perform an X-ray crystallographic analysis of the antigen (full length)-antibody complex. Janis Kuby, Immunology, (1992) p. 80.

Still another method for choosing an epitope of interest which may generate a T cell response is to identify from the protein sequence potential HLA anchor binding motifs which are peptide sequences which are known to be likely to bind to the MHC molecule.

The peptide which is a putative epitope of interest, to generate a T cell response, should be presented in a MHC complex. The peptide preferably contains appropriate anchor motifs for binding to the MHC molecules, and should bind with high enough affinity to generate an immune response. Factors which may be considered are: the HLA type of the patient (vertebrate, animal or human) expected to be immunized, the sequence of the protein, the presence of appropriate anchor motifs and the occurrence of the peptide sequence in other vital cells.

An immune response is generated, in general, as follows: T cells recognize proteins only when the protein has been cleaved into smaller peptides and is presented in a complex called the "major histocompatability complex MHC" located on another cell's surface. There are two classes of MHC complexes—class I and class II, and each class is made up of many different alleles. Different patients have different types of MHC complex alleles; they are said to have a different HLA type.

Class I MHC complexes are found on virtually every cell and present peptides from proteins produced inside the cell. Thus, Class I MHC complexes are useful for killing cells which when infected by viruses or which have become cancerous and as the result of expression of an oncogene. T cells which have a protein called CD8 on their surface, bind to the MHC class I cells and secrete lymphokines. The lymphokines stimulate a response; cells arrive and kill the viral infected cell.

Class II MHC complexes are found only on antigen-presenting cells and are used to present peptides from circulating pathogens which have been endocytosed by the antigen-presenting cells. T cells which have a protein called CD4 bind to the MHC class II cells and kill the cell by exocytosis of lytic granules.

Some guidelines in determining whether a protein is an epitopes of interest which will stimulate a T cell response, include: Peptide length—the peptide should be at least 8 or 9 amino acids long to fit into the MEW class I complex and at least 13-25 amino acids long to fit into a class II MCH complex. This length is a minimum for the peptide to bind to the MEW complex. It is preferred for the peptides to be longer than these lengths because cells may cut the expressed peptides. The peptide should contain an appropriate anchor motif which will enable it to bind to the various class I or class II molecules with high enough specificity to generate an immune response (See Bocchia, M. et al, Specific Binding of Leukemia Oncogene Fusion Protein Peptides to HLA Class I Molecules, Blood 85:2680-2684; Englehard, V H, Structure of peptides associated with class I and class II MEW molecules Ann. Rev. Immunol. 12:181 (1994)). This may be done, without undue experimentation, by comparing the sequence of the protein of interest with published structures of peptides associated with the MHC molecules. Protein epitopes recognized by T cell receptors are peptides generated by enzymatic degradation of the protein molecule and are presented on the cell surface in association with class I or class II MEW molecules.

Further, the skilled artisan may ascertain an epitope of interest by comparing the protein sequence with sequences listed in the protein data base. Regions of the protein which share little or no homology are better choices for being an epitope of that protein and are therefore useful in a vaccine or immunological composition. Regions which share great homology with widely found sequences present in vital cells should be avoided.

Even further, another method is simply to generate or express portions of a protein of interest, generate monoclonal antibodies to those portions of the protein of interest, and then ascertain whether those antibodies inhibit growth in vitro of the pathogen from which the from which the protein was derived. The skilled artisan may use the other guidelines set forth in this disclosure and in the art for generating or expressing portions of a protein of interest for analysis as to whether antibodies thereto inhibit growth in vitro. For example, the skilled artisan may generate portions of a protein of interest by: selecting 8 to 9 or 13 to 25 amino acid length portions of the protein, selecting hydrophilic regions, selecting portions shown to bind from X-ray data of the antigen (full length)-antibody complex, selecting regions which differ in sequence from other proteins, selecting potential HLA anchor binding motifs, or any combination of these methods or other methods known in the art.

Epitopes recognized by antibodies are expressed on the surface of a protein. To determine the regions of a protein most likely to stimulate an antibody response one skilled in the art may preferably perform an epitope map, using the general methods described above, or other mapping methods known in the art.

As may be seen from the foregoing, without undue experimentation, from this disclosure and the knowledge in the art, the skilled artisan may ascertain the amino acid and corresponding DNA sequence of an epitope of interest for obtaining a T cell, B cell and/or antibody response. In addition, reference is made to Gefter et al., U.S. Pat. No. 5,019,384, issued May 28, 1991, and the documents it cites, incorporated herein by reference (Note especially the "Relevant Literature" section of this patent, and column 13 of this patent which discloses that: "A large number of epitopes have been defined for a wide variety of organisms of interest. Of particular interest are those epitopes to which neutralizing antibodies are directed.

With respect to expression of a biological response modulator, reference is made to Wohlstadter, "Selection Methods," WO 93/19170, published Sep. 30, 1993, and the documents cited therein, incorporated herein by reference.

For instance, a biological response modulator modulates biological activity; for instance, a biological response modulator is a modulatory component such as a high molecular weight protein associated with non-NMDA excitatory amino acid receptors and which allosterically regulates affinity of AMPA binding (See Kendrew, supra). The recombinant of the present invention may express such a high molecular weight protein.

More generally, nature has provided a number of precedents of biological response modulators. Modulation of activity may be carried out through mechanisms as complicated and intricate as allosteric induced quaternary change to simple presence/absence, e.g., expression/degradation, systems. Indeed, the repression/activation of expression of many biological molecules is itself mediated by molecules whose activities are capable of being modulated through a variety of mechanisms.

Table 2 of Neidhardt et al Physiology of the Bacterial Cell (Sinauer Associates Inc., Publishers, 1990), at page 73, lists chemical modifications to bacterial proteins. As is noted in that table, some modifications are involved in proper assembly and other modifications are not, but in either case such modifications are capable of causing modulation of function. From that table, analogous chemical modulations for proteins of other cells may be determined, without undue experimentation.

In some instances modulation of biological functions may be mediated simply through the proper/improper localization of a molecule. Molecules may function to provide a growth advantage or disadvantage only if they are targeted to a particular location. For example, a molecule may be typically not taken up or used by a cell, as a function of that molecule being first degraded by the cell by secretion of an enzyme for that degradation. Thus, production of the enzyme by a recombinant may regulate use or uptake of the molecule by a cell. Likewise, the recombinant may express a molecule which binds to the enzyme necessary for uptake or use of a molecule, thereby similarly regulating its uptake or use.

Localization targeting of proteins carried out through cleavage of signal peptides another type of modulation or regulation. In this case, a specific endoprotease catalytic activity may be expressed by the recombinant.

Other examples of mechanisms through which modulation of function may occur are RNA virus poly-proteins, allosteric effects, and general covalent and non-covalent steric hindrance. HIV is a well studied example of an RNA virus which expresses non-functional poly-protein constructs. In HIV "the gag, pol, and env poly-proteins are processed to yield, respectively, the viral structural proteins p17, p24, and p15—reverse transcriptase and integrase—and the two envelope proteins gp41 and gp120" (Kohl et al., PNAS USA 85:4686-90 (1988)). The proper cleavage of the poly-proteins is crucial for replication of the virus, and virions carrying inactive mutant HIV protease are non-infectious. This is another example of the fusion of proteins down-modulating their activity. Thus, it is possible to construct recombinant viruses which express molecules which interfere with endoproteases, or which provide endoproteases, for inhibiting or enhancing the natural expression of certain proteins (by interfering with or enhancing cleavage).

The functional usefulness of enzymes may also be modulated by altering their capability of catalyzing a reaction. Illustrative examples of modulated molecules are zymogens, formation/disassociation of multi-subunit functional complexes, RNA virus poly-protein chains, allosteric interactions, general steric hindrance (covalent and non-covalent) and a variety of chemical modifications such as phosphorylation, methylation, acetylation, adenylation, and uridenylation (see Table 1 of Neidhardt, supra, at page 315 and Table 2 at page 73).

Zymogens are examples of naturally occurring protein fusions which cause modulation of enzymatic activity. Zymogens are one class of proteins which are converted into their active state through limited proteolysis. See Table 3 of Reich, Proteases and Biological Control, Vol. 2, (1975) at page 54). Nature has developed a mechanism of down-modulating the activity of certain enzymes, such as trypsin, by expressing these enzymes with additional "leader" peptide sequences at their amino termini. With the extra peptide sequence the enzyme is in the inactive zymogen state. Upon cleavage of this sequence the zymogen is converted to its enzymatically active state. The overall reaction rates of the zymogen are "about $10^5$-$10^6$ times lower than those of the corresponding enzyme" (See Table 3 of Reich, supra at page 54).

It is therefore possible to down-modulate the function of certain enzymes simply by the addition of a peptide sequence to one of its termini. For example, with knowledge of this property, a recombinant may express peptide sequences containing additional amino acids at one or both termini.

The formation or disassociation of multi-subunit enzymes is another way through which modulation may occur. Different mechanisms may be responsible for the modulation of activity upon formation or disassociation of multi-subunit enzymes.

Therefore, sterically hindering the proper specific subunit interactions will down-modulate the catalytic activity. And accordingly, the recombinant of the invention may express a molecule which sterically hinders a naturally occurring enzyme or enzyme complex, so as to modulate biological functions.

Certain enzyme inhibitors afford good examples of functional down-modulation through covalent steric hindrance or modification. Suicide substrates which irreversibly bind to the active site of an enzyme at a catalytically important amino acid in the active site are examples of covalent modifications which sterically block the enzymatic active site. An example of a suicide substrate is TPCK for chymotrypsin (Fritsch, Enzyme Structure and Mechanism, 2d ed; Freeman & Co. Publishers, 1984)). This type of modulation is possible by the recombinant expressing a suitable suicide substrate, to thereby modulate biological responses (e.g., by limiting enzyme activity).

There are also examples of non-covalent steric hindrance including many repressor molecules. The recombinant may express repressor molecules which are capable of sterically hindering and thus down-modulating the function of a DNA sequence by preventing particular DNA-RNA polymerase interactions.

Allosteric effects are another way through which modulation is carried out in some biological systems. Aspartate transcarbamoylase is a well characterized allosteric enzyme. Interacting with the catalytic subunits are regulatory domains. Upon binding to CTP or UTP the regulatory subunits are capable of inducing a quaternary structural change in the holoenzyme causing down-modulation of catalytic activity. In contrast, binding of ATP to the regulatory subunits is capable of causing up-modulation of catalytic activity (Fritsch, supra). Using methods of the invention, molecules may be expressed which are capable of binding and causing modulatory quaternary or tertiary changes.

In addition, a variety of chemical modifications, e.g., phosphorylation, methylation, acetylation, adenylation, and uridenylation may be carried out so as to modulate function. It is known that modifications such as these play important roles in the regulation of many important cellular components. Table 2 of Neidhardt, supra, at page 73, lists different bacterial enzymes which undergo such modifications. From that list, one skilled in the art may ascertain other enzymes of other systems which undergo the same or similar modifications, without undue experimentation. In addition, many proteins which are implicated in human disease also undergo such chemical modifications. For example, many oncogenes have been found to be modified by phosphorylation or to modify other proteins through phosphorylation or dephosphorylation. Therefore, the ability afforded by the invention to express modulators which may modify or alter function, e.g., phosphorylation, is of importance.

From the foregoing, the skilled artisan may use the present invention to express a biological response modulator, without any undue experimentation.

With respect to expression of fusion proteins by inventive recombinants, reference is made to Sambrook, Fritsch, Maniatis, Molecular Cloning, A LABORATORY MANUAL (2d Edition, Cold Spring Harbor Laboratory Press, 1989) (especially Volume 3), and Kendrew, supra, incorporated herein by reference. The teachings of Sambrook et al., may be suitably modified, without undue experimentation, from this disclosure, for the skilled artisan to generate recombinants expressing fusion proteins.

With regard to gene therapy and immunotherapy, reference is made to U.S. Pat. Nos. 4,690,915 and 5,252,479, which are incorporated herein by reference, together with the documents cited therein it and on their face, and to WO 94/16716 and U.S. application Ser. No. 08/184,009, filed Jan. 19, 1994, each of which is also incorporated herein by reference, together with the documents cited therein.

A growth factor may be defined as multifunctional, locally acting intercellular signaling peptides which control both ontogeny and maintenance of tissue and function (see Kendrew, especially at page 455 et seq.).

The growth factor or therapeutic gene, for example, may encode a disease-fighting protein, a molecule for treating cancer, a tumor suppressor, a cytokine, a tumor associated antigen, or interferon; and, the growth factor or therapeutic gene may, for example, be selected from the group consisting of a gene encoding alpha-globin, beta-globin, gamma-globin, granulocyte macrophage-colony stimulating factor, tumor necrosis factor, an interleukin (e.g., an interleukin selected from interleukins 1 to 14, or 1 to 11, or any combination thereof), macrophage colony stimulating factor, granulocyte colony stimulating factor, erythropoietin, mast cell growth factor, tumor suppressor p53, retinoblastoma, interferon, melanoma associated antigen or B7. U.S. Pat. No. 5,252,479 provides a list of proteins which may be expressed in an adenovirus system for gene therapy, and the skilled artisan is directed to that disclosure. WO 94/16716 and U.S. application Ser. No. 08/184,009, filed Jan. 19, 1994, provide genes for cytokines and tumor associated antigens and immunotherapy methods, including ex vivo methods, and the skilled artisan is directed to those disclosures.

Thus, one skilled in the art may create recombinants expressing a growth factor or therapeutic gene and use the recombinants, from this disclosure and the knowledge in the art, without undue experimentation.

Moreover, from the foregoing and the knowledge in the art, no undue experimentation is required for the skilled artisan to construct an inventive recombinant which expresses an epitope of interest, a biological response modulator, a growth factor, a recognition sequence, a therapeutic gene, or a fusion protein; or for the skilled artisan to use such a recombinant.

It is noted that the exogenous or heterologous DNA may itself include a promoter for driving expression in the recombinant CMV, or the exogenous DNA may simply be coding DNA and appropriately placed downstream from an endogenous promoter to drive expression. Further, multiple copies of coding DNA or use of a strong or early promoter or early and late promoter, or any combination thereof, may be done so as to amplify or increase expression. Thus, the exogenous or heterologous DNA may be suitably positioned with respect to an endogenous promoter like the E3 or the MLP promoters, or those promoters may be translocated to be inserted at another location, with the exogenous or heterologous DNA. The coding DNA may be DNA coding for more than one protein so as to have expression of more than one product from the recombinant CMV.

The expression products may be antigens, immunogens or epitopes of interest; and therefore, the invention further relates to immunological, antigenic or vaccine compositions containing the expression products. Further, since the CMV vector, in certain instances, may be administered directly to a suitable host, the invention relates to compositions containing the CMV vector. Additionally, since the expression product may be isolated from the CMV vector in vitro or from cells infected or transfected by the CMV vector in vitro, the invention relates to methods for expressing a product, e.g., which may comprise inserting the exogenous DNA into a CMV as a vector, e.g., by restriction/ligation or by recombination followed by infection or transfection of suitable cells in vitro with a recombinant CMV, and optionally extracting, purifying or isolating the expression product from the cells. Any suitable extraction, purification or isolation techniques may be employed.

In particular, after infecting cells with the recombinant CMV, the protein(s) from the expression of the exogenous DNA are collected by known techniques such as chromatography (see Robbins, EPA 0162738A1; Panicali, EPA 0261940A2); Richardson, supra; Smith et al., supra; Pennock et al., supra; EP Patent Publication No. 0265785). The collected protein(s) may then be employed in a vaccine, antigenic or immunological composition which also contains a suitable carrier.

Thus, the recombinant CMV may be used to prepare proteins such as antigens, immunogens, epitopes of interest, etc. which may be further used in immunological, antigenic or vaccine compositions. It is noted that a recombinant CMV expressing a product detrimental to growth or development of insects may be used to prepare an insecticide, and a recombinant CMV expressing a product detrimental to growth of plants may be used to prepare a herbicide (by isolating the expression product and admixing it with an insecticidally or herbicidally acceptable carrier or diluent) and a recombinant CMV expressing an anti-fungal polypeptide may be used to prepare an anti-fungal preparation (by isolating the expression product and admixing it with a suitable carrier or diluent).

As the expression products may provide an antigenic, immunological or protective (vaccine) response, the invention further relates to products therefrom; namely, antibodies and uses thereof. More in particular, the expression products may elicit antibodies. The antibodies may be formed into monoclonal antibodies; and, the antibodies or expression products may be used in kits, assays, tests, and the like involving binding, so that the invention relates to these uses too. Additionally, since the recombinants of the invention may be used to replicate DNA, the invention relates to recombinant CMV as a vector and methods for replicating DNA by infecting or transfecting cells with the recombinant and harvesting DNA therefrom. The resultant DNA may be used as probes or primers or for amplification.

The administration procedure for recombinant CMV or expression product thereof, compositions of the invention such as immunological, antigenic or vaccine compositions or therapeutic compositions may be via a parenteral route (intradermal, intramuscular or subcutaneous). Such an administration enables a systemic immune response. The administration may be via a mucosal route, e.g., oral, nasal, genital, etc. Such an administration enables a local immune response.

More generally, the inventive antigenic, immunological or vaccine compositions or therapeutic compositions (compositions containing the CMV recombinants of the invention or expression products) may be prepared in accordance with standard techniques well known to those skilled in the pharmaceutical arts. Such compositions may be administered in dosages and by techniques well known to those skilled in the medical arts taking into consideration such factors as the breed or species, age, sex, weight, and condition of the particular patient, and the route of administration. The compositions may be administered alone, or may be co-administered or sequentially administered with other compositions of the invention or with other immunological, antigenic or vaccine or therapeutic compositions. Such other compositions may include purified native antigens or epitopes or antigens or epitopes from the expression by a recombinant CMV or another vector system; and are administered taking into account the aforementioned factors.

Examples of compositions of the invention include liquid preparations for orifice, e.g., oral, nasal, anal, genital, e.g., vaginal, etc., administration such as suspensions, syrups or elixirs; and, preparations for parenteral, subcutaneous, intradermal, intramuscular or intravenous administration (e.g., injectable administration) such as sterile suspensions or emulsions. In such compositions the recombinant may be in admixture with a suitable carrier, diluent, or excipient such as sterile water, physiological saline, glucose or the like.

Antigenic, immunological or vaccine compositions typically may contain an adjuvant and an amount of the recombinant CMV or expression product to elicit the desired response. In human applications, alum (aluminum phosphate or aluminum hydroxide) is a typical adjuvant. Saponin and its purified component Quil A, Freund's complete adjuvant and other adjuvants used in research and veterinary applications have toxicities which limit their potential use in human vaccines. Chemically defined preparations such as muramyl dipeptide, monophosphoryl lipid A, phospholipid conjugates such as those described by Goodman-Snitkoff et al. J. Immunol. 147:410-415 (1991) and incorporated by reference herein, encapsulation of the protein within a proteoliposome as described by Miller et al., J. Exp. Med. 176:1739-1744 (1992) and incorporated by reference herein, and encapsulation of the protein in lipid vesicles such as Novasome lipid vesicles (Micro Vescular Systems, Inc., Nashua, N.H.) may also be used.

The composition may be packaged in a single dosage form for immunization by parenteral (i.e., intramuscular, intradermal or subcutaneous) administration or orifice administration, e.g., perlingual (i.e., oral), intragastric, mucosal including intraoral, intraanal, intravaginal, and the like administration. And again, the effective dosage and route of administration are determined by the nature of the composition, by the nature of the expression product, by expression level if recombinant CMV is directly used, and by known factors, such as breed or species, age, sex, weight, condition and nature of host, as well as LD50 and other screening procedures which are known and do not require undue experimentation. Dosages of expressed product may range from a few to a few hundred micrograms, e.g., 5 to 500 µg. The inventive recombinant may be administered in any suitable amount to achieve expression at these dosage levels. The vaccinal CMV is administered in an amount of about 103.5 pfu; thus, the inventive recombinant is preferably administered in at least this amount; more preferably about $10^4$ pfu to about $10^6$ pfu. Other suitable carriers or diluents may be water or a buffered saline, with or without a preservative. The expression product or recombinant CMV may be lyophilized for resuspension at the time of administration or may be in solution.

The carrier may also be a polymeric delayed release system. Synthetic polymers are particularly useful in the formulation of a composition having controlled release. An early example of this was the polymerization of methyl methacrylate into spheres having diameters less than one micron to form so-called nano particles, reported by Kreuter, J., Microcapsules and Nanoparticles in Medicine and Pharmacology, M. Donbrow (Ed). CRC Press, p. 125-148.

Microencapsulation has been applied to the injection of microencapsulated pharmaceuticals to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters and polyamides, particularly those that are biodegradable.

A frequent choice of a carrier for pharmaceuticals and more recently for antigens is poly (d,1-lactide-co-glycolide)

(PLGA). This is a biodegradable polyester that has a long history of medical use in erodible sutures, bone plates and other temporary prostheses where it has not exhibited any toxicity. A wide variety of pharmaceuticals including peptides and antigens have been formulated into PLGA microcapsules. A body of data has accumulated on the adaption of PLGA for the controlled release of antigen, for example, as reviewed by Eldridge, J. H., et al. Current Topics in Microbiology and Immunology. 1989, 146:59-66. The entrapment of antigens in PLGA microspheres of 1 to 10 microns in diameter has been shown to have a remarkable adjuvant effect when administered orally. The PLGA microencapsulation process uses a phase separation of a water-in-oil emulsion. The compound of interest is prepared as an aqueous solution and the PLGA is dissolved in a suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, polyvinylpyrrolidone (PVP), methyl cellulose) and the solvent removed by either drying in vacuo or solvent extraction.

Thus, solid, including solid-containing-liquid, liquid, and gel (including "gel caps") compositions are envisioned.

Additionally, the inventive vectors, e.g., recombinant CMV, and the expression products therefrom may stimulate an immune or antibody response in animals. From those antibodies, by techniques well-known in the art, monoclonal antibodies may be prepared and, those monoclonal antibodies, may be employed in well known antibody binding assays, diagnostic kits or tests to determine the presence or absence of antigen(s) and therefrom the presence or absence of the natural causative agent of the antigen or, to determine whether an immune response to that agent or to the antigen(s) has simply been stimulated.

Monoclonal antibodies are immunoglobulin produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies may be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H., U.S. Pat. No. 4,376,110, issued Mar. 8, 1983, incorporated herein by reference.

Monoclonal antibodies have also been used to recover materials by immunoadsorption chromatography, e.g. Milstein, C., 1980, Scientific American 243:66, 70, incorporated herein by reference.

Furthermore, the inventive recombinant CMV or expression products therefrom may be used to stimulate a response in cells in vitro or ex vivo for subsequent reinfusion into a patient. If the patient is seronegative, the reinfusion is to stimulate an immune response, e.g., an immunological or antigenic response such as active immunization. In a seropositive individual, the reinfusion is to stimulate or boost the immune system against a pathogen.

The recombinant CMV of the invention are also useful for generating DNA for probes or for PCR primers which may be used to detect the presence or absence of hybridizable DNA or to amplify DNA, e.g., to detect a pathogen in a sample or for amplifying DNA.

Furthermore, as discussed above, the invention comprehends promoters and expression cassettes which are useful in adenovirus systems, as well as in any viral or cell system which provides a transactivating protein.

The expression cassette of the invention may further include a functional truncated polyadenylation signal; for instance an SV40 polyadenylation signal which is truncated, yet functional. The expression cassette may contain exogenous or heterologous DNA (with respect to the virus or system into which the promoter or expression cassette is being inserted); for instance exogenous or heterologous coding DNA as herein described above, and in the Examples. This DNA may be suitably positioned and operably linked to the promoter for expression. The expression cassette may be inserted in any orientation; preferably the orientation which obtains maximum expression from the system or virus into which the expression cassette is inserted.

While the promoter and expression cassette are specifically exemplified with reference to adenoviruses, the skilled artisan may adapt these embodiments of the invention to other viruses and to plasmids for cells such as eukaryotic cells, without undue experimentation, by simply ascertaining whether the virus, plasmid, cell or system provides the transactivating protein.

As to HCMV promoters, reference is made to U.S. Pat. Nos. 5,168,062 and 5,385,839, incorporated herein by reference. As to transfecting cells with plasmid DNA for expression therefrom, reference is made to Felgner et al. (1994), J. Biol. Chem. 269, 2550-2561, incorporated herein by reference. And, as to direct injection of plasmid DNA as a simple and effective method of vaccination against a variety of infectious diseases reference is made to Science, 259:1745-49, 1993, incorporated herein by reference. It is therefore within the scope of this invention that the inventive promoter and expression cassette be used in systems other than adenovirus; for example, in plasmids for the direct injection of plasmid DNA.

The protein fragments of the present invention form a further aspect of the invention; and, such compounds may be used in methods of medical treatments, such as for diagnosis, preventing or treating HIV or for eliciting antibodies for diagnosis of HIV, including use in vaccines. Further, such compounds may be used in the preparation of medicaments for such treatments or prevention, or compositions for diagnostic purposes. The compounds may be employed alone or in combination with other treatments, vaccines or preventatives; and, the compounds may be used in the preparation of combination medicaments for such treatments or prevention, or in kits containing the compound and the other treatment or preventative.

In yet another embodiment, the present invention also encompassed the use of the protein fragments of the present invention described herein as immunogens, advantageously as HIV-1 vaccine components.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, F(ab')2, Fv and scFv which are capable of binding the epitope determinant. These antibody fragments retain some ability to selectively bind with its antigen or receptor and include, for example:

a. Fab, the fragment which contains a monovalent antigen-binding fragment of an antibody molecule may be produced by digestion of whole antibody with the enzyme papain to yield an intact light chain and a portion of one heavy chain;
b. Fab', the fragment of an antibody molecule may be obtained by treating whole antibody with pepsin, followed by reduction, to yield an intact light chain and a portion of the heavy chain; two Fab' fragments are obtained per antibody molecule;
c. F(ab')2, the fragment of the antibody that may be obtained by treating whole antibody with the enzyme pepsin without subsequent reduction; F(ab')2 is a dimer of two Fab' fragments held together by two disulfide bonds;
d. scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

A "neutralizing antibody" may inhibit the entry of HIV-1 virus for example SF162 and/or JRCSF with a neutralization index >1.5 or >2.0. Broad and potent neutralizing antibodies may neutralize greater than about 50% of HIV-1 viruses (from diverse clades and different strains within a clade) in a neutralization assay. The inhibitory concentration of the monoclonal antibody may be less than about 25 mg/ml to neutralize about 50% of the input virus in the neutralization assay.

It should be understood that the proteins, including the antibodies and/or antigens of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid may be single-stranded, or partially or completely double-stranded (duplex). Duplex nucleic acids may be homoduplex or heteroduplex.

As used herein the term "transgene" may be used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

As regards codon optimization, the nucleic acid molecules of the invention have a nucleotide sequence that encodes the antigens of the invention and may be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens may be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart. Thus, the nucleotide sequences of the invention may readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 may be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms may be downloaded. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies and/or antigens of the present invention may be used in accordance with the present invention. In certain embodiments, the antigens and/or antibodies of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the antigens and/or antibodies in vitro and/or in cultured cells may be used.

For applications where it is desired that the antibodies and/or antigens be expressed in vivo, for example when the transgenes of the invention are used in DNA or DNA-containing vaccines, any vector that allows for the expression of the antibodies and/or antigens of the present invention and is safe for use in vivo may be used. In preferred embodiments the vectors used are safe for use in humans, mammals and/or laboratory animals.

For the antibodies and/or antigens of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" may be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention may be under the control of a constitutive promoter or of an inducible promoter, which initiates transcription only when exposed to some particular external stimulus, such as, without limitation, antibiotics such as tetracycline, hormones such as ecdysone, or heavy metals. The promoter may also be specific to a particular cell-type, tissue or organ. Many suitable promoters and enhancers are known in the art, and any such suitable promoter or enhancer may be used for expression of the transgenes of the invention. For example, suitable promoters and/or enhancers may be selected from the Eukaryotic Promoter Database (EPDB).

The present invention relates to a recombinant vector expressing a foreign epitope. Advantageously, the epitope is an HIV epitope. In an advantageous embodiment, the HIV epitope is a protein fragment of the present invention, however, the present invention may encompass additional HIV antigens, epitopes or immunogens. Advantageously, the HIV epitope is an HIV antigen, HIV epitope or an HIV immunogen, such as, but not limited to, the HIV antigens, HIV epitopes or HIV immunogens of U.S. Pat. Nos. 7,341,731; 7,335,364; 7,329,807; 7,323,553; 7,320,859; 7,311,920; 7,306,798; 7,285,646; 7,285,289; 7,285,271; 7,282,364; 7,273,695; 7,270,997; 7,262,270; 7,244,819; 7,244,575; 7,232,567; 7,232,566; 7,223,844; 7,223,739; 7,223,534; 7,223,368; 7,220,554; 7,214,530; 7,211,659; 7,211,432; 7,205,159; 7,198,934; 7,195,768; 7,192,555; 7,189,826; 7,189,522; 7,186,507; 7,179,645; 7,175,843; 7,172,761; 7,169,550; 7,157,083; 7,153,509; 7,147,862; 7,141,550; 7,129,219; 7,122,188; 7,118,859; 7,118,855; 7,118,751; 7,118,742; 7,105,655; 7,101,552; 7,097,971 7,097,842; 7,094,405; 7,091,049; 7,090,648; 7,087,377; 7,083,787;

7,070,787; 7,070,781; 7,060,273; 7,056,521; 7,056,519; 7,049,136; 7,048,929; 7,033,593; 7,030,094; 7,022,326; 7,009,037; 7,008,622; 7,001,759; 6,997,863; 6,995,008; 6,979,535; 6,974,574; 6,972,126; 6,969,609; 6,964,769; 6,964,762; 6,958,158; 6,956,059; 6,953,689; 6,951,648; 6,946,075; 6,927,031; 6,919,319; 6,919,318; 6,919,077; 6,913,752; 6,911,315; 6,908,617; 6,908,612; 6,902,743; 6,900,010; 6,893,869; 6,884,785; 6,884,435; 6,875,435; 6,867,005; 6,861,234; 6,855,539; 6,841,381 6,841,345; 6,838,477; 6,821,955; 6,818,392; 6,818,222; 6,815,217; 6,815,201; 6,812,026; 6,812,025; 6,812,024; 6,808,923; 6,806,055; 6,803,231; 6,800,613; 6,800,288; 6,797,811; 6,780,967; 6,780,598; 6,773,920; 6,764,682; 6,761,893; 6,753,015; 6,750,005; 6,737,239; 6,737,067; 6,730,304; 6,720,310; 6,716,823; 6,713,301; 6,713,070; 6,706,859; 6,699,722; 6,699,656; 6,696,291; 6,692,745; 6,670,181; 6,670,115; 6,664,406; 6,657,055; 6,657,050; 6,656,471; 6,653,066; 6,649,409; 6,649,372; 6,645,732; 6,641,816; 6,635,469; 6,613,530; 6,605,427; 6,602,709 6,602,705; 6,600,023; 6,596,477; 6,596,172; 6,593,103; 6,593,079; 6,579,673; 6,576,758; 6,573,245; 6,573,040; 6,569,418; 6,569,340; 6,562,800; 6,558,961; 6,551,828; 6,551,824; 6,548,275; 6,544,780; 6,544,752; 6,544,728; 6,534,482; 6,534,312; 6,534,064; 6,531,572; 6,531,313; 6,525,179; 6,525,028; 6,524,582; 6,521,449; 6,518,030; 6,518,015; 6,514,691; 6,514,503; 6,511,845; 6,511,812; 6,511,801; 6,509,313; 6,506,384; 6,503,882; 6,495,676; 6,495,526; 6,495,347; 6,492,123; 6,489,131; 6,489,129; 6,482,614; 6,479,286; 6,479,284; 6,465,634; 6,461,615 6,458,560; 6,458,527; 6,458,370; 6,451,601; 6,451,592; 6,451,323; 6,436,407; 6,432,633; 6,428,970; 6,428,952; 6,428,790; 6,420,139; 6,416,997; 6,410,318; 6,410,028; 6,410,014; 6,407,221; 6,406,710; 6,403,092; 6,399,295; 6,392,013; 6,391,657; 6,384,198; 6,380,170; 6,376,170; 6,372,426; 6,365,187; 6,358,739; 6,355,248; 6,355,247; 6,348,450; 6,342,372; 6,342,228; 6,338,952; 6,337,179; 6,335,183; 6,335,017; 6,331,404; 6,329,202; 6,329,173; 6,328,976; 6,322,964; 6,319,666; 6,319,665; 6,319,500; 6,319,494; 6,316,205; 6,316,003; 6,309,633; 6,306,625 6,296,807; 6,294,322; 6,291,239; 6,291,157; 6,287,568; 6,284,456; 6,284,194; 6,274,337; 6,270,956; 6,270,769; 6,268,484; 6,265,562; 6,265,149; 6,262,029; 6,261,762; 6,261,571; 6,261,569; 6,258,599; 6,258,358; 6,248,332; 6,245,331; 6,242,461; 6,241,986; 6,235,526; 6,235,466; 6,232,120; 6,228,361; 6,221,579; 6,214,862; 6,214,804; 6,210,963; 6,210,873; 6,207,185; 6,203,974; 6,197,755; 6,197,531; 6,197,496; 6,194,142; 6,190,871; 6,190,666; 6,168,923; 6,156,302; 6,153,408; 6,153,393; 6,153,392; 6,153,378; 6,153,377; 6,146,635; 6,146,614; 6,143,876 6,140,059; 6,140,043; 6,139,746; 6,132,992; 6,124,306; 6,124,132; 6,121,006; 6,120,990; 6,114,507; 6,114,143; 6,110,466; 6,107,020; 6,103,521; 6,100,234; 6,099,848; 6,099,847; 6,096,291; 6,093,405; 6,090,392; 6,087,476; 6,083,903; 6,080,846; 6,080,725; 6,074,650; 6,074,646; 6,070,126; 6,063,905; 6,063,564; 6,060,256; 6,060,064; 6,048,530; 6,045,788; 6,043,347; 6,043,248; 6,042,831; 6,037,165; 6,033,672; 6,030,772; 6,030,770; 6,030,618; 6,025,141; 6,025,125; 6,020,468; 6,019,979; 6,017,543; 6,017,537; 6,015,694; 6,015,661; 6,013,484; 6,013,432 6,007,838; 6,004,811; 6,004,807; 6,004,763; 5,998,132; 5,993,819; 5,989,806; 5,985,926; 5,985,641; 5,985,545; 5,981,537; 5,981,505; 5,981,170; 5,976,551; 5,972,339; 5,965,371; 5,962,428; 5,962,318; 5,961,979; 5,961,970; 5,958,765; 5,958,422; 5,955,647; 5,955,342; 5,951,986; 5,951,975; 5,942,237; 5,939,277; 5,939,074; 5,935,580; 5,928,930; 5,928,913; 5,928,644; 5,928,642; 5,925,513; 5,922,550; 5,922,325; 5,919,458; 5,916,806; 5,916,563; 5,914,395; 5,914,109; 5,912,338; 5,912,176; 5,912,170; 5,906,936; 5,895,650; 5,891,623; 5,888,726; 5,885,580 5,885,578; 5,879,855; 5,876,731; 5,876,716; 5,874,226; 5,872,012; 5,871,747; 5,869,058; 5,866,694; 5,866,341; 5,866,320; 5,866,319; 5,866,137; 5,861,290; 5,858,740; 5,858,647; 5,858,646; 5,858,369; 5,858,368; 5,858,366; 5,856,185; 5,854,400; 5,853,736; 5,853,725; 5,853,724; 5,852,186; 5,851,829; 5,851,529; 5,849,475; 5,849,288; 5,843,728; 5,843,723; 5,843,640; 5,843,635; 5,840,480; 5,837,510; 5,837,250; 5,837,242; 5,834,599; 5,834,441; 5,834,429; 5,834,256; 5,830,876; 5,830,641; 5,830,475; 5,830,458; 5,830,457; 5,827,749; 5,827,723; 5,824,497 5,824,304; 5,821,047; 5,817,767; 5,817,754; 5,817,637; 5,817,470; 5,817,318; 5,814,482; 5,807,707; 5,804,604; 5,804,371; 5,800,822; 5,795,955; 5,795,743; 5,795,572; 5,789,388; 5,780,279; 5,780,038; 5,776,703; 5,773,260; 5,770,572; 5,766,844; 5,766,842; 5,766,625; 5,763,574; 5,763,190; 5,762,965; 5,759,769; 5,756,666; 5,753,258; 5,750,373; 5,747,641; 5,747,526; 5,747,028; 5,736,320; 5,736,146; 5,733,760; 5,731,189; 5,728,385; 5,721,095; 5,716,826; 5,716,637; 5,716,613; 5,714,374; 5,709,879; 5,709,860; 5,709,843; 5,705,331; 5,703,057; 5,702,707 5,698,178; 5,688,914; 5,686,078; 5,681,831; 5,679,784; 5,674,984; 5,672,472; 5,667,964; 5,667,783; 5,665,536; 5,665,355; 5,660,990; 5,658,745; 5,658,569; 5,643,756; 5,641,624; 5,639,854; 5,639,598; 5,637,677; 5,637,455; 5,633,234; 5,629,153; 5,627,025; 5,622,705; 5,614,413; 5,610,035; 5,607,831; 5,606,026; 5,601,819; 5,597,688; 5,593,972; 5,591,829; 5,591,823; 5,589,466; 5,587,285; 5,585,254; 5,585,250; 5,580,773; 5,580,739; 5,580,563; 5,573,916; 5,571,667; 5,569,468; 5,558,865; 5,556,745; 5,550,052; 5,543,328; 5,541,100; 5,541,057; 5,534,406 5,529,765; 5,523,232; 5,516,895; 5,514,541; 5,510,264; 5,500,161; 5,480,967; 5,480,966; 5,470,701; 5,468,606; 5,462,852; 5,459,127; 5,449,601; 5,447,838; 5,447,837; 5,439,809; 5,439,792; 5,418,136; 5,399,501; 5,397,695; 5,391,479; 5,384,240; 5,374,519; 5,374,518; 5,374,516; 5,364,933; 5,359,046; 5,356,772; 5,354,654; 5,344,755; 5,335,673; 5,332,567; 5,320,940; 5,317,009; 5,312,902; 5,304,466; 5,296,347; 5,286,852; 5,268,265; 5,264,356; 5,264,342; 5,260,308; 5,256,767; 5,256,561; 5,252,556; 5,230,998; 5,230,887; 5,227,159; 5,225,347; 5,221,610 5,217,861; 5,208,321; 5,206,136; 5,198,346; 5,185,147; 5,178,865; 5,173,400; 5,173,399; 5,166,050; 5,156,951; 5,135,864; 5,122,446; 5,120,662; 5,103,836; 5,100,777; 5,100,662; 5,093,230; 5,077,284; 5,070,010; 5,068,174; 5,066,782; 5,055,391; 5,043,262; 5,039,604; 5,039,522; 5,030,718; 5,030,555; 5,030,449; 5,019,387; 5,013,556; 5,008,183; 5,004,697; 4,997,772; 4,983,529; 4,983,387; 4,965,069; 4,945,082; 4,921,787; 4,918,166; 4,900,548; 4,888,290; 4,886,742; 4,885,235; 4,870,003; 4,869,903; 4,861,707; 4,853,326; 4,839,288; 4,833,072 and 4,795,739.

In another embodiment, HIV, or immunogenic fragments thereof, may be utilized as the HIV epitope. For example, the HIV nucleotides of U.S. Pat. Nos. 7,393,949, 7,374,877, 7,306,901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any epitope recognized by an HIV antibody may be used in the present invention. For example, the anti-HIV antibodies of U.S. Pat. Nos. 6,949,337, 6,900,010, 6,821,744, 6,768,004, 6,613,743, 6,534,312, 6,511,830, 6,489,131, 6,242,197, 6,114,143, 6,074,646, 6,063,564, 6,060,254, 5,919,457, 5,916,806, 5,871,732, 5,824,304, 5,773,247, 5,736,320, 5,637,455, 5,587,285, 5,514,541, 5,317,009, 4,983,529, 4,886,742, 4,870,003 and 4,795,739 are useful for the present invention. Furthermore, monoclonal anti-HIV antibodies of U.S. Pat. Nos. 7,074,556, 7,074,554, 7,070,787, 7,060,273, 7,045,130, 7,033,593, RE39,057, 7,008,622, 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

The present invention relates to a recombinant vector expressing a foreign epitope. Advantageously, the epitope is a SIV epitope. It is understood by one of skill in the art that anything referring to HIV in the specification also applies to SIV. In an advantageous embodiment, the SIV epitope is a protein fragment of the present invention, however, the present invention may encompass additional SIV antigens, epitopes or immunogens. Advantageously, the SIV epitope is an SIV antigen, SIV epitope or an SIV immunogen, such as, but not limited to, the SIV antigens, SIV epitopes or SIV immunogens of U.S. Pat. Nos. 7,892,729; 7,886,962; 7,879,914; 7,829,287; 7,794,998; 7,767,455; 7,759,477; 7,758,869; 7,754,420; 7,749,973; 7,748,618; 7,732,124; 7,709,606; 7,700,342; 7,700,273; 7,625,917; 7,622,124; 7,611,721; 7,608,422; 7,601,518; 7,585,675; 7,534,603; 7,511,117; 7,508,781; 7,507,417; 7,479,497; 7,464,352; 7,457,973; 7,442,551; 7,439,052; 7,419,829; 7,407,663; 7,378,515; 7,364,760; 7,312,065; 7,261,876; 7,220,554; 7,211,240; 7,198,935; 7,169,394; 7,098,201; 7,078,516; 7,070,993; 7,048,929; 7,034,010; RE39,057; 7,022,814; 7,018,638; 6,955,919; 6,933,377; 6,908,617; 6,902,929; 6,846,477; 6,818,442; 6,803,231; 6,800,281; 6,797,811; 6,790,657; 6,712,612; 6,706,729; 6,703,394; 6,682,907; 6,656,706; 6,645,956; 6,635,472; 6,596,539; 6,589,763; 6,562,571; 6,555,523; 6,555,342; 6,541,009; 6,531,574; 6,531,123; 6,503,713; 6,479,281; 6,475,718; 6,469,083; 6,468,539; 6,455,265; 6,448,390; 6,440,730; 6,423,544; 6,365,150; 6,362,000; 6,326,007; 6,322,969; 6,291,664; 6,277,601; 6,261,571; 6,255,312; 6,207,455; 6,194,142; 6,117,656; 6,111,087; 6,107,020; 6,080,846; 6,060,064; 6,046,228; 6,043,081; 6,027,731; 6,020,123; 6,017,536; 6,004,781; 5,994,515; 5,981,259; 5,961,976; 5,950,176; 5,929,222; 5,928,913; 5,912,176; 5,888,726; 5,861,243; 5,861,161; 5,858,366; 5,830,475; 5,817,316; 5,804,196; 5,786,177; 5,759,768; 5,747,324; 5,705,522; 5,705,331; 5,698,446; 5,688,914; 5,688,637; 5,654,195; 5,650,269; 5,631,154; 5,582,967; 5,552,269; 5,512,281; 5,508,166; 5,470,572; 5,312,902; 5,310,651; 5,268,265; 5,254,457; 5,212,084; 5,087,631 and 4,978,687.

The vectors used in accordance with the present invention should typically be chosen such that they contain a suitable gene regulatory region, such as a promoter or enhancer, such that the antigens and/or antibodies of the invention may be expressed.

When the aim is to express the antibodies and/or antigens of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies and/or antigens of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. Any vectors that are suitable for such uses may be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Advantageously, the vector is a CMV vector, preferably lacking one or more of the glycoproteins US2, US3, US6 and US11. In yet another embodiment, all of the genes between US2 and US11 region of the CMV genome are deleted. In another embodiment, where superinfectivity or repeated infectivity is desired, any vector, advantageously a viral vector, may express one or more of the glycoproteins US2, US3, US6 and US11. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and may be used as gene delivery vectors. However, these vectors are immunogenic and induce immunity against the vector which prohibits their repeated use unless they express US2-11.

In an embodiment where superinfectivity or repeated infectivity is desired, any vector, advantageously a viral vector, may express one or more of the glycoproteins US2, US3, US6 and US11. In a particularly advantageous embodiment, the vector expresses glycoproteins US2, US3, US6 and US11. More advantageously, the vector contains and expresses all of the glycoproteins within the US2 to US11 region of CMV. In an advantageous embodiment, the one or more of the glycoproteins US2, US3, US6 and US11 may include, but not limited to, the glycoproteins of U.S. Pat. Nos. 7,892,564; 7,749,745; 7,364,893; 6,953,661; 6,913,751; 6,740,324; 6,613,892; 6,410,033; 6,140,114; 6,103,531; 6,033,671; 5,908,780; 5,906,935; 5,874,279; 5,853,733; 5,846,806; 5,843,458; 5,837,532; 5,804,372; 5,753,476; 5,741,696; 5,731,188; 5,720,957; 5,676,952; 5,599,544; 5,593,873 and 5,334,498.

The nucleotide sequences and vectors of the invention may be delivered to cells, for example if aim is to express and the HIV-1 antigens in cells in order to produce and isolate the expressed proteins, such as from cells grown in culture. For expressing the antibodies and/or antigens in cells any suitable transfection, transformation, or gene delivery methods may be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies and/or antigens may be carried out in any suitable type of host cells, such as bacterial cells, yeast, insect cells, and mammalian cells. The antibodies and/or antigens of the invention may also be expressed using including in vitro transcription/translation systems. All of such methods are well known by those skilled in the art, and one of skill in the art would readily be able to select a suitable method depending on the nature of the nucleotide sequences, vectors, and cell types used.

In preferred embodiments, the nucleotide sequences, antibodies and/or antigens of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, antibodies and/or antigens of the invention are preferably administered as a component of an immunogenic composition which may comprise the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies and/or antigens of the invention to a subject, such as a human, such that the antibodies and/or antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition may also be formulated in the form of an oil-in-water emulsion. The oil-in-water emulsion may be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri(caprylate/caprate) or propylene glycol dioleate; esters of branched fatty acids or alcohols, e.g., isostearic acid esters. The oil advantageously is used in combination with emulsifiers to form the emulsion. The emulsifiers may be non-ionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant may be a mixture of emulsifier(s), micelle-forming agent, and oil such as that which is commercially available under the name Provax® (IDEC Pharmaceuticals, San Diego, Calif.).

The immunogenic compositions of the invention may contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., AlK(SO4)2, AlNa (SO4)2, AlNH(SO4)2, silica, alum, Al(OH)3, Ca3(PO4)2, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34th Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from *Mycobacterium tuberculosis*, substances found in *Cornyebacterium parvum*, *Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that may be used, especially with DNA vaccines, are cholera toxin, especially CTA1-DD/ISCOMs (see Mowat, A. M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or α-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which may be administered either as proteins or in the form of DNA, on the same expression vectors as those encoding the antigens of the invention or on separate expression vectors.

The immunogenic compositions may be designed to introduce the nucleic acids or expression vectors to a desired site of action and release it at an appropriate and controllable rate. Methods of preparing controlled-release formulations are known in the art. For example, controlled release preparations may be produced by the use of polymers to complex or absorb the immunogen and/or immunogenic composition. A controlled-release formulations may be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention may be readily determined by those of skill in the art. For example, the dosage of the immunogens may vary depending on the route of administration and the size of the subject. Suitable doses may be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions may serve to provide protective immunity of a subject against HIV-1 infection or to prevent or attenuate the progression of AIDS in a subject already infected with HIV-1. When provided therapeutically, the immunogenic compositions may serve to ameliorate and treat AIDS symptoms and are advantageously used as soon after infection as possible, preferably before appearance of any symptoms of AIDS but may also be used at (or after) the onset of the disease symptoms.

The immunogenic compositions may be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes may be oral, intranasal or by any other suitable route. Delivery also be accomplished via a mucosal surface such as the anal, vaginal or oral mucosa.

Immunization schedules (or regimens) are well known for animals (including humans) and may be readily determined for the particular subject and immunogenic composition. Hence, the immunogens may be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. In a particularly advantageous embodiment of the present invention, the interval is longer, advantageously about 10 weeks, 12 weeks, 14 weeks, 16 weeks, 18 weeks, 20 weeks, 22 weeks, 24 weeks, 26 weeks, 28 weeks, 30 weeks, 32 weeks, 34 weeks, 36 weeks, 38 weeks, 40 weeks, 42 weeks, 44 weeks, 46 weeks, 48 weeks, 50 weeks, 52 weeks, 54 weeks, 56 weeks, 58 weeks, 60 weeks, 62 weeks, 64 weeks, 66 weeks, 68 weeks or 70 weeks. In a most advantageous embodiment, the interval is about 16 weeks or about 53 weeks.

The immunization regimes typically have from 1 to 6 administrations of the immunogenic composition, but may have as few as one or two or four. The methods of inducing an immune response may also include administration of an adjuvant with the immunogens. In some instances, annual, biannual or other long interval (5-10 years) booster immunization may supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition may be the same or different for each immunization and the type of immunogenic composition (e.g., containing protein or expression vector), the route, and formulation of the immunogens may also be varied. For example, if an expression vector is used for the priming and boosting steps, it may either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens. In the event that the viral vectors express US2-11 they may be used repeatedly while expressing different antigens derived from different pathogens.

A specific embodiment of the invention provides methods of inducing an immune response against HIV in a subject by administering an immunogenic composition of the invention, preferably which may comprise an US2-11 expressing adenovirus vector containing DNA encoding one or more of the epitopes of the invention, one or more times to a subject wherein the epitopes are expressed at a level sufficient to induce a specific immune response in the subject. Such immunizations may be repeated multiple times at time intervals of at least 2, 4 or 6 weeks (or more) in accordance with a desired immunization regime.

The immunogenic compositions of the invention may be administered alone, or may be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages may be determined taking into consideration such factors as the age, sex, weight, species and condition of the particular subject, and the route of administration.

When used in combination, the other HIV immunogens may be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which may be administered as a protein, on a plasmid (e.g., pTHr.HIVA) or in a viral vector (e.g., MVA-.HIVA). Another such HIV immunogen is RENTA (described in PCT/US2004/037699), which may also be administered as a protein, on a plasmid (e.g., pTHr.RENTA) or in a viral vector (e.g., MVA.RENTA).

For example, one method of inducing an immune response against HIV in a human subject may comprise administering at least one priming dose of an HIV immunogen and at least one boosting dose of an HIV immunogen, wherein the immunogen in each dose may be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response may include an HIV-specific T-cell immune response or an HIV-specific B-cell immune response. Such immunizations may be done at intervals, preferably of at least 2-6 or more weeks.

Although the present invention and its advantages have been described in detail, it should be understood that various changes, substitutions and alterations may be made herein without departing from the spirit and scope of the invention as defined in the appended claims.

EXAMPLES

Example 1: Evasion of $CD8^+$ T Cells is Critical for Superinfection by Cytomegalovirus Cytomegalovirus (CMV) may superinfect persistently infected hosts despite CMV-specific humoral and cellular immunity; however, how it does so remains undefined. Applicants have demonstrated that superinfection of rhesus CMV-infected rhesus macaques (RM) requires evasion of CD8+ T cell immunity by virally encoded inhibitors of major histocompatibility complex class I (MHC-I) antigen presentation, particularly the homologs of human CMV US2, 3, 6, and 11. In contrast, MHC-I interference was dispensable for primary infection of RM, or for the establishment of a persistent secondary infection in CMV-infected RM transiently depleted of CD8+ lymphocytes.

These findings demonstrate that US2-11 glycoproteins promote evasion of CD8+ T cells in vivo, thus supporting viral replication and dissemination during superinfection, a process that complicates the development of preventive CMV vaccines but that may be exploited for CMV-based vector development.

A general characteristic of the adaptive immune response to viruses is its ability to prevent or rapidly extinguish secondary infections by identical or closely related viruses. A notable exception is the herpesvirus family member cytomegalovirus (CMV), which may repeatedly establish persistent infection in immunocompetent hosts (S. B. Boppana et al. *N. Engl. J. Med.* 344, 1366 (2001), S. Gorman et al., *J. Gen. Virol.* 87, 1123 (2006) and S. G. Hansen et al., *Nat. Med.* 15, 293 (2009)). Sequential infections are likely the reason for the presence of multiple human CMV (HCMV) genotypes in the human host (Meyer-Konig et al. *Lancet* 352, 1280 (1998)). This ability to establish secondary persistent infections despite the preexistence of persistent virus (referred to as "superinfection") is particularly notable because healthy CMV-infected individuals develop high-titer neutralizing antibody responses and manifest very-high-frequency CD4+ and CD8+ CMV-specific T cell responses (>10% of circulating memory T cells may be CMV-specific) (A. W. Sylwester et al., *J. Exp. Med.* 202, 673 (2005)). This evasion of pre-existing immunity has frustrated attempts to develop preventive CMV vaccines (S. P. Adler et al., *J. Infect. Dis.* 171, 26 (1995) and S. A. Plotkin et al., *J. Infect. Dis.* 159, 860 (1989)) but may be exploited for the development of CMV vectors capable of repeatedly initiating de novo T cell responses to heterologous pathogens in CMV-positive hosts (S. G. Hansen et al., *Nat. Med.* 15, 293 (2009)).

Figure 1B:
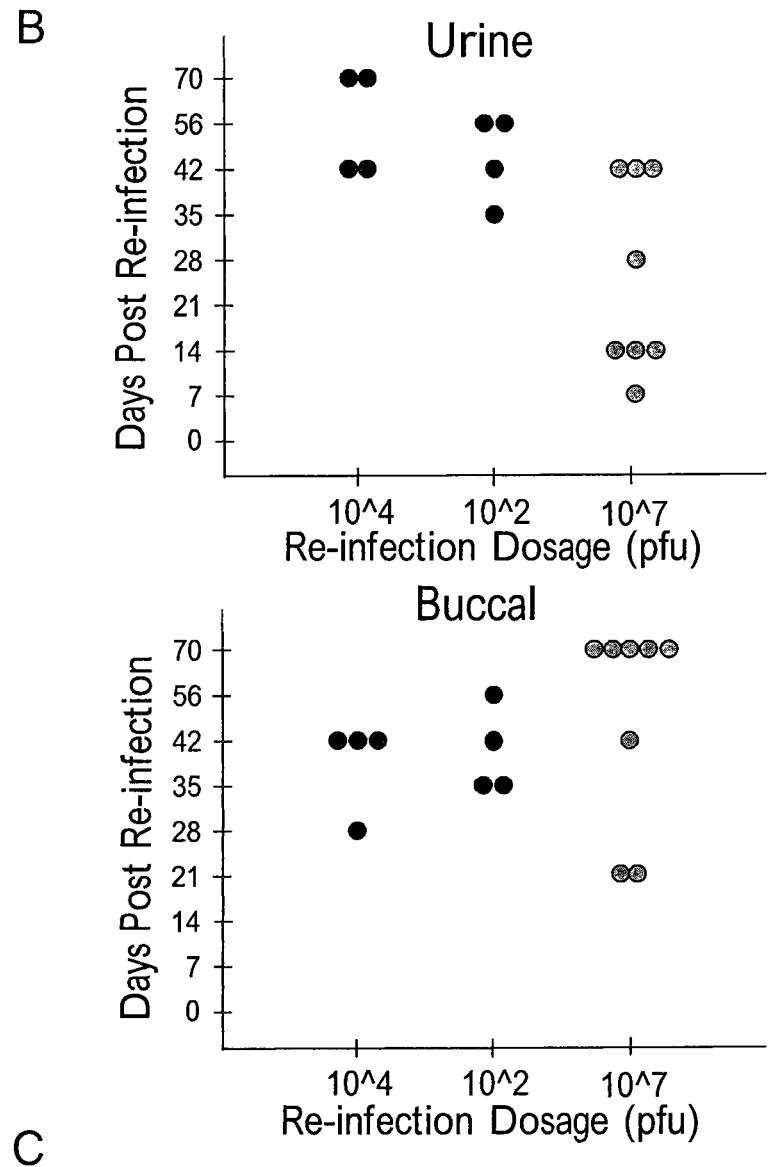
Figure 1C:
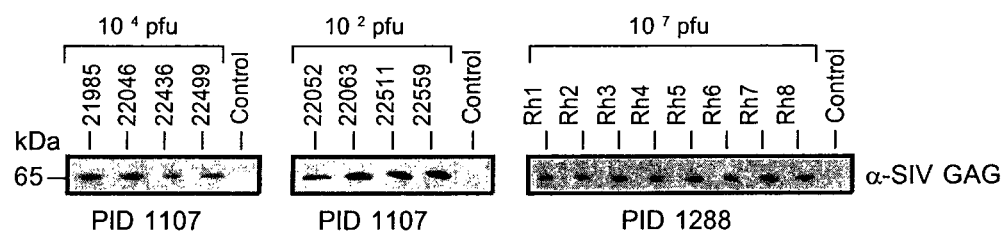
Figure 6:
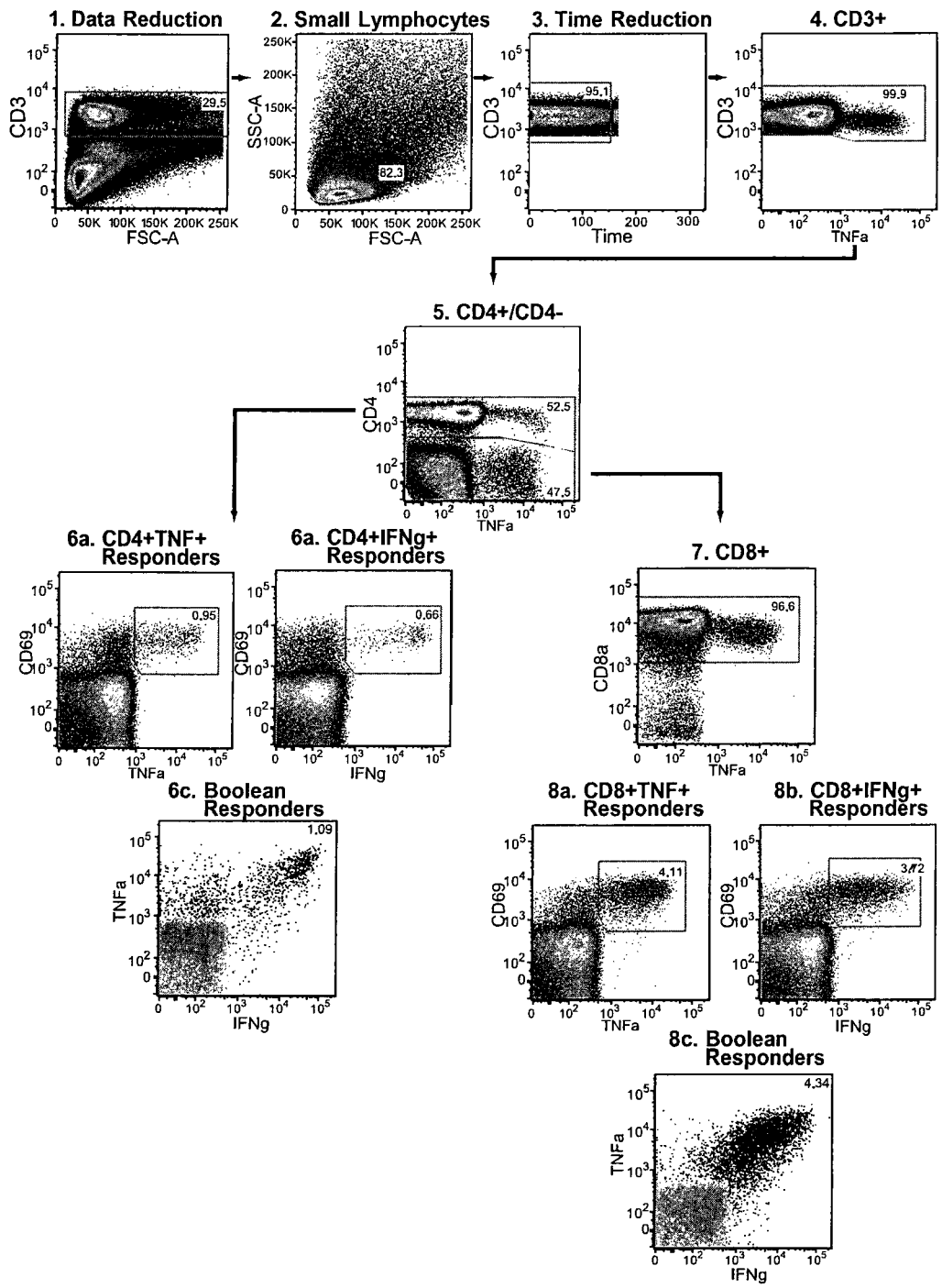
FIG. 6. Response frequency gating strategy. Lymphocytes originating from PBMC and BAL were stimulated with Ag, stained and collected on a flow cytometer as described in Example 1. Data was analyzed using a hierarchical gating strategy to delineate Ag-responding subsets. Gates are depicted here in pink, with corresponding subset names numbered and displayed above the cytometric plots. For FIG. 1, response frequencies were determined using the $CD69^+/TNF\alpha^+$ subset ($CD4^+$, cytometric plot 6a; $CD8^+$, cytometric plot 8a). Response values for all other figures were determined using Boolean gating to delineate cells that are $CD69^+$ and TNFα+/IFN-γ–, TNFα–/IFN-γ+, or TNFα+/IFN-γ+ ("Boolean Responders"; CD4+, cytometric plot 6c; $CD8^+$, cytometric plot 8c).
Figure 7:
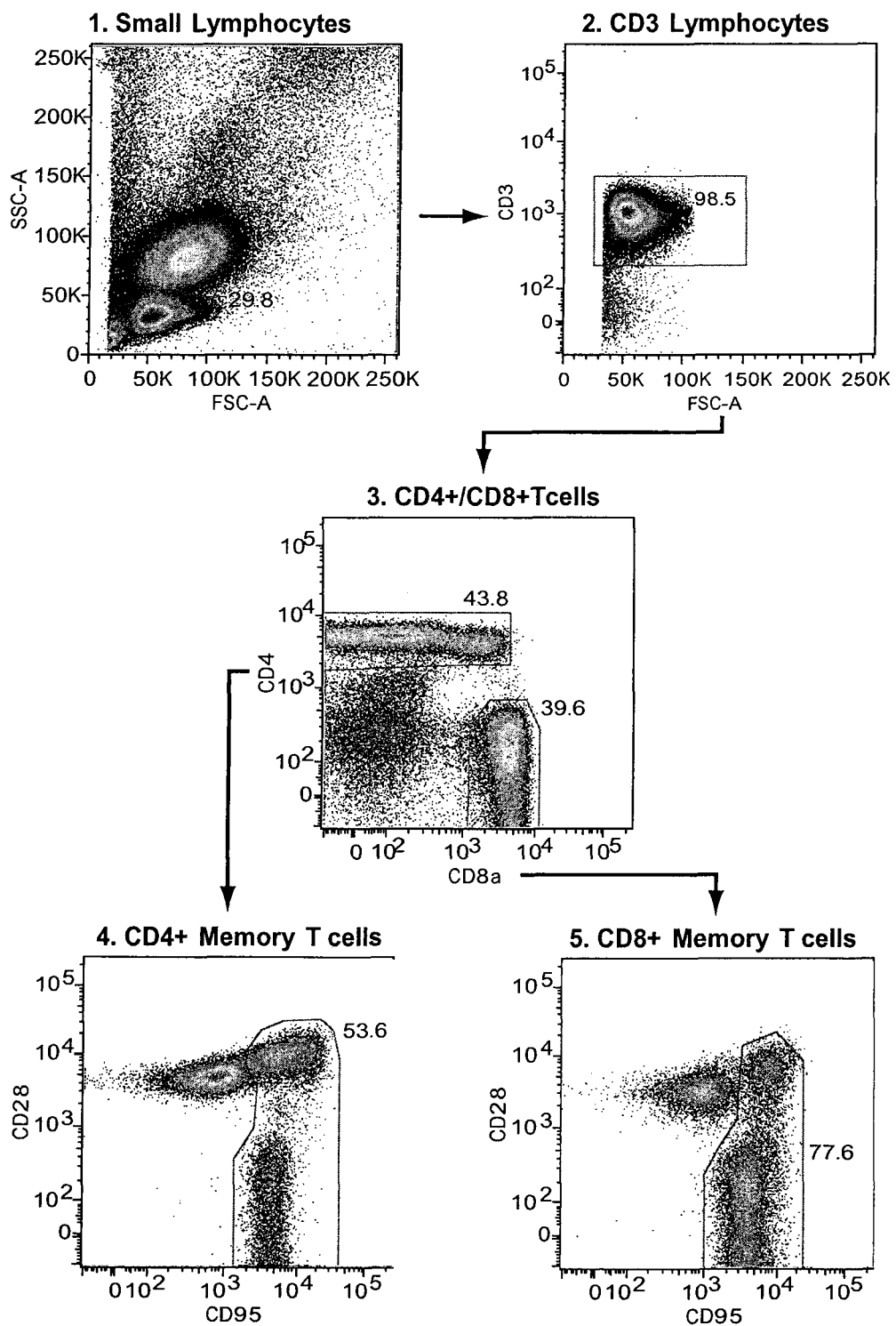
FIG. 7. Memory correction gating hierarchy. Cell preparations were stained and the data collected as described (C. J. Pitcher et al., *J Immunol* 168, 29 (2002)), followed by hierarchical analysis shown here. The pink boxes in cytometric plot 2 and 3 indicate the overall T cell and T cell subset gates, respectively. The memory correction values used for PBMC response calculations reflect the percentage of the events within the memory gate of $CD4^+$ or $CD8^+$ T cell-gated profiles (cytometric plots 4 and 5, respectively).

The biologic importance of this superinfection capability has prompted Applicants' investigation of its extent and mechanism. Applicants previously showed that inoculation of RhCMV+ rhesus macaques (RM) with 107 plaque-forming units (PFU) of genetically modified RhCMV (strain 68-1) expressing simian immunodeficiency virus (SIV) antigens resulted in superinfection manifested by the persistent shedding of the genetically modified CMV in the urine and saliva and by the induction and long-term maintenance of de novo CD4+ and CD8+ T cell responses specific for the SIV insert (S. G. Hansen et al., *Nat. Med.* 15, 293 (2009)). To determine whether RhCMV would be able to overcome immunity at lower, more physiologic doses of infection, as reported for HCMV (S. A. Plotkin et al. *J. Infect. Dis.* 159, 860 (1989)), a recombinant RhCMV containing a loxP-flanked expression cassette for SIVgag [RhCMV(gagL)] (FIG. 5) was inoculated subcutaneously at doses of 104 or 102 PFU into four RM naturally infected by RhCMV, as manifested by the presence of robust RhCMV-specific T cell responses (Table 1A). The SIVgag-specific T cell responses in peripheral blood mononuclear cells (PBMC) or in broncho-alveolar lavage lymphocytes (BAL) were monitored by flow cytometric analysis of intracellular cytokine staining (ICCS) (FIGS. 6 and 7) after stimulation with consecutive overlapping 15-amino acid peptides corresponding to SIV-gag. Reduction of the inoculating dose had minimal impact on superinfection dynamics: All animals developed SIVgag-specific T cell responses within 2 weeks (FIG. 1A), and secretion of SIVgag-expressing virus in urine or buccal swabs was observed within 4 to 10 weeks of infection in both cohorts (FIG. 1B). The time to first detection of secreted virus in these low-dose-challenged RM was not materially different from that of eight RhCMV+ animals infected with 107 PFU of RhCMV(gagL) (FIG. 1B). Moreover, the SIVgag-specific T cell responses and RhCMV (gagL) secretion were stable for more than 3 years regardless of initial dose (FIGS. 1, A and C). These data indicate that, consistent with HCMV in humans, RhCMV is able to overcome high levels of CMV-specific immunity and to establish secondary persistent infections, even with low doses of challenge virus.

TABLE 1

Baseline RhCMV-specific T cell responses in PBMC of study RM.
Shown are the animal numbers as well as the percent RhCMV-specific
CD4+ and CD8+ T cells measured by intracellular cytokine staining.

| | FIGS. | Infecting Virus | RM# | CD4 | CD8 |
|---|---|---|---|---|---|
| A | FIG. 1 | $10^4$ PFU RhCMV (gagL) | 21985 | 1.70 | 0.68 |
| | | | 22046 | 1.29 | 0.37 |
| | | | 22463 | 1.27 | 0.36 |
| | | | 22499 | 1.71 | 0.30 |
| | | $10^2$ PFU RhCMV (gagL) | 22052 | 2.04 | 0.12 |
| | | | 22063 | 2.37 | 0.43 |
| | | | 22511 | 3.16 | 0.55 |
| | | | 22559 | 1.05 | 0.42 |
| | | | avg ± sd | 1.82 ± 0.69 | 0.41 ± 0.16 |
| B | FIG. 2 | ΔUS2-11 (gag) | 21973 | 0 | 0 |
| | | | 24350 | 0 | 0 |
| | | ΔVIHCEΔUS2-11 (gag) | 23609 | 0 | 0 |
| | | | 23634 | 0 | 0 |
| | | | avg ± sd | 0 | 0 |
| C | FIG. 3 | ΔVIHCE (gag) ΔRh186-8(retanef) | 23101 | 2.112 | 0.576 |
| | | | 23126 | 2.242 | 0.809 |
| | | | 23132 | 2.273 | 1.343 |
| | | | 23244 | 3.295 | 0.779 |
| | | | avg ± sd | 2.48 ± 0.55 | 0.88 ± 0.33 |
| D | FIG. 4 | ΔVIHCEΔUS2-11 (gag) | 21308 | 0.612 | 0.197 |
| | | | 21456 | 1.167 | 0.238 |
| | | ΔUS2-11 (gag) | 21794 | 0.961 | 0.214 |
| | | | 23923 | 0.942 | 0.166 |
| | | | avg ± sd | 0.92 ± 0.23 | 0.21 ± 0.03 |

Applicants hypothesized that an essential step during CMV superinfection is the ability of the virus to clear an initial immunological checkpoint. A likely candidate for such an immunological barrier is CD8+ cytotoxic T cells (CTL), because they are crucial for controlling CMV-associated diseases (E. A. Walter et al., *N. Engl. J. Med.* 333, 1038 (1995)). The importance of CTL control for CMV is also suggested by viral expression of multiple proteins that inhibit presentation of viral peptide antigens to CD8+ T cells via major histocompatibility complex class I (MHC-I) molecules (A. K. Pinto, A. B. Hill, *Viral Immunol.* 18, 434 (2005)). HCMV encodes at least four related glycoproteins, each with a unique mechanism to prevent antigen presentation: US2 and US11 mediate the retrograde translocation of MHC-I into the cytosol for proteasomal destruction (F. J. van der Wal et al. *Curr. Top. Microbiol. Immunol.* 269, 37 (2002)), US3 retains MHC-I in the endoplasmic reticulum by interfering with chaperone-controlled peptide loading (Z. Liu et al. *Int. J. Biochem. Cell Biol.* 41, 503 (2009)), and US6 inhibits the translocation of viral and host peptides across the endoplasmic reticulum membrane by the dedicated peptide transporter TAP (transporter associated with antigen processing) (E. W. Hewitt et al. *EMBO J.* 20, 387 (2001)). RhCMV encodes sequence and functional homologs of these genes in a genomic region spanning Rh182 (US2) to Rh189 (US11) (FIG. 5) (N. T. Pande et al. *J. Virol.* 79, 5786 (2005)). Furthermore, the Rh178 gene encodes the RhCMV-specific viral inhibitor of heavy chain expression (VIHCE), which prevents signal-sequence-dependent translation/translocation of MHC-I (C. J. Powers, K. Früh, *PLoS Pathog.* 4, e1000150 (2008)).

Figure 2A:
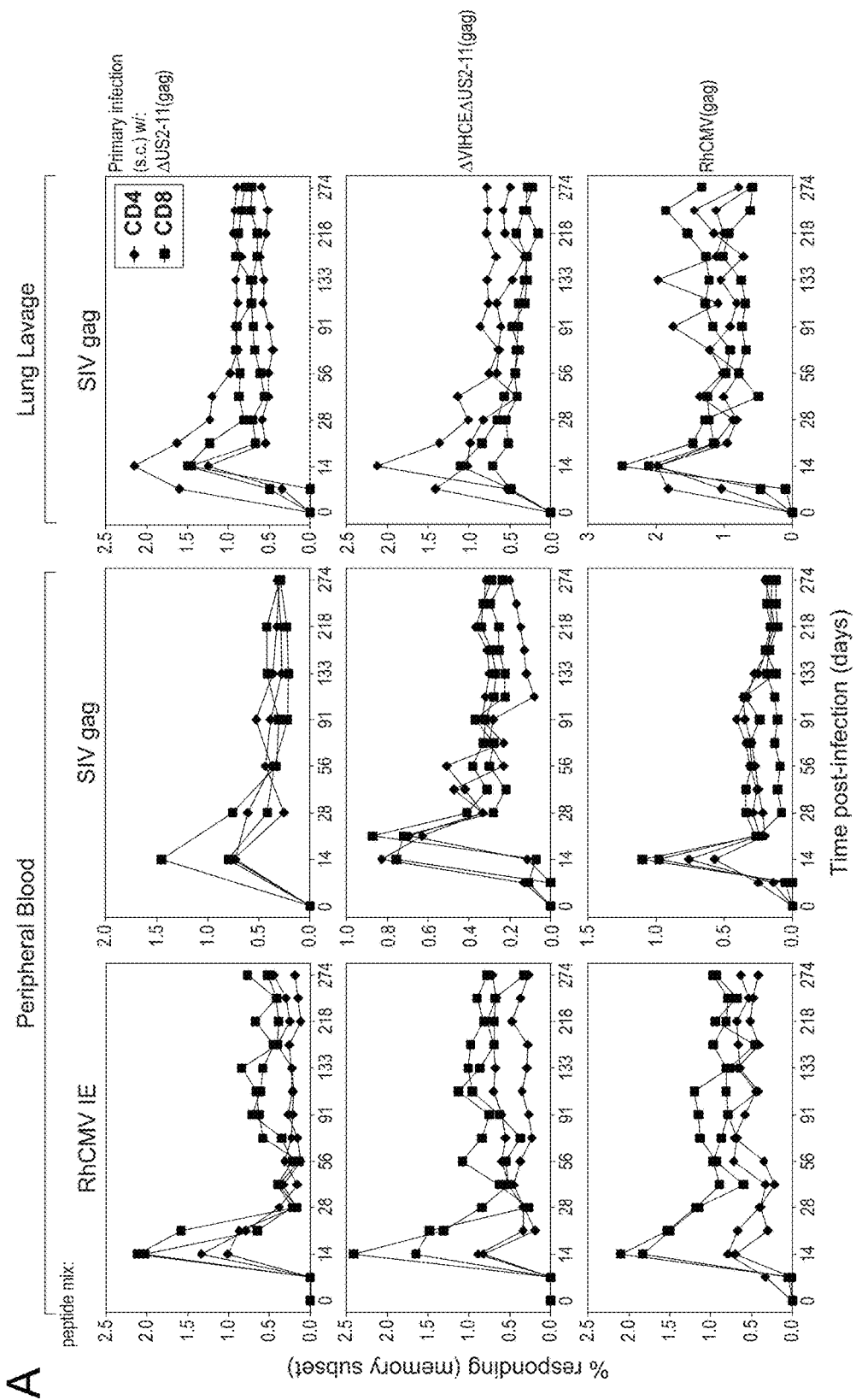
FIGS. 2A-2C. Interference with MHC-I assembly is not required for primary infection of CMV-naïve animals. Three cohorts of two RM each were inoculated subcutaneously with 107 PFU of recombinant $\Delta$US2-11(gag), $\Delta$VIHCE$\Delta$US2-11(gag), or RhCMV(gag). $\Delta$US2-11(gag) lacks the RhCMV gene region Rh182-Rh189 encoding the homologues of HCMV US2-11 (N. T. Pande et al. J Virol 79:5786 (2005)), $\Delta$VIHCE$\Delta$US2-11(gag) additionally lacks the RhCMV gene Rh178 encoding the viral inhibitor of heavy chain expression (VIHCE) (C. J. Powers et al. PLoS Pathog 4:e1000150 (2008). (A) The RhCMV-specific T cell response in PBMC and the SIVgag-specific T cell response in PBMC and BAL were determined at the indicated days post-infection using overlapping peptides to RhCMV immediate early genes IE1 and IE2 or SIVgag by flow cytometric analysis of ICCS for CD69, TNF-$\alpha$, and interferon-$\gamma$ (IFN-$\gamma$) (S. G. Hansen et al. *Science* 328, 5974 (2010)) (see FIGS. 6 and 7). (B) Immunoblot of RhCMV-IE2 or SIVgag expressed in cocultures of urine samples obtained from animals infected with ΔUS2-11(gag) or ΔVIHCEΔUS2-11 (gag). The IE2 blot confirms that the animals were negative for RhCMV before infection, consistent with results from T cell assays (table 1B). (C) PCR analysis of viral genomic DNA isolated from viral cocultures at 428 days post-infection. The presence or absence of indicated ORFs was determined by PCR using specific primers (S. G. Hansen et al. *Science* 328, 5974 (2010)). One of the animals infected with RhCMV(gag) served as a control.
Figures 2B, 2C:
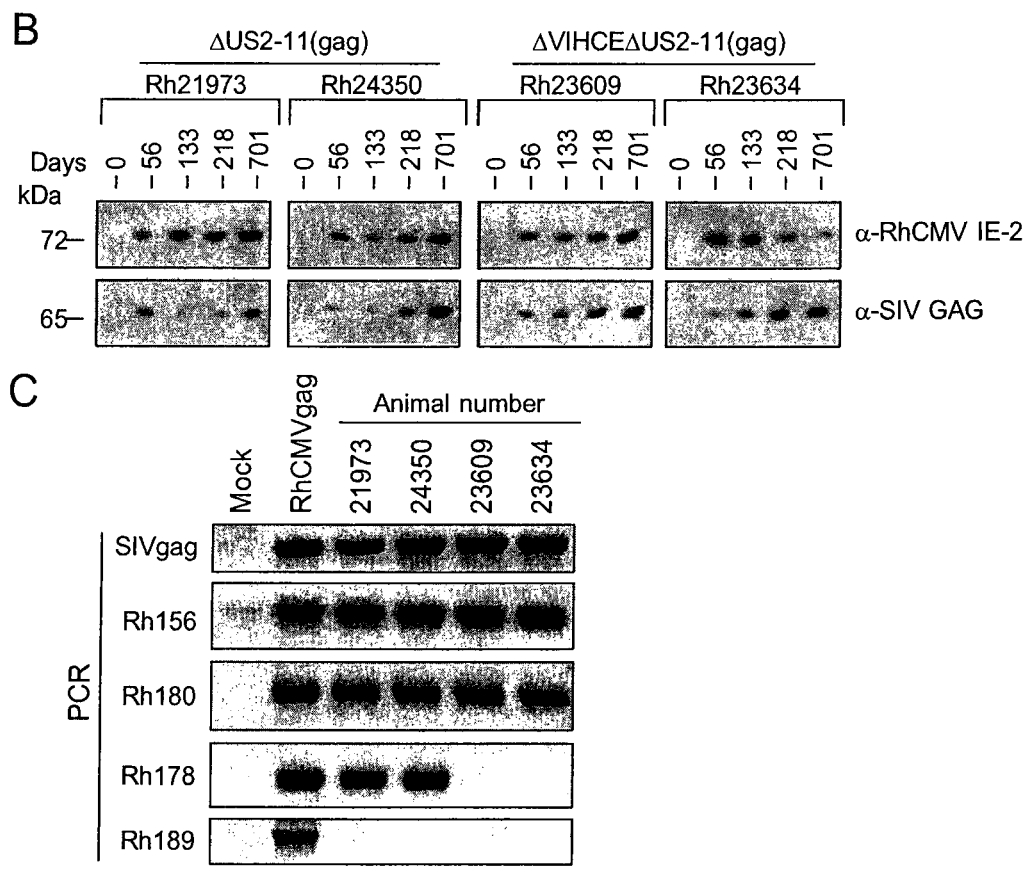
Figure 5:
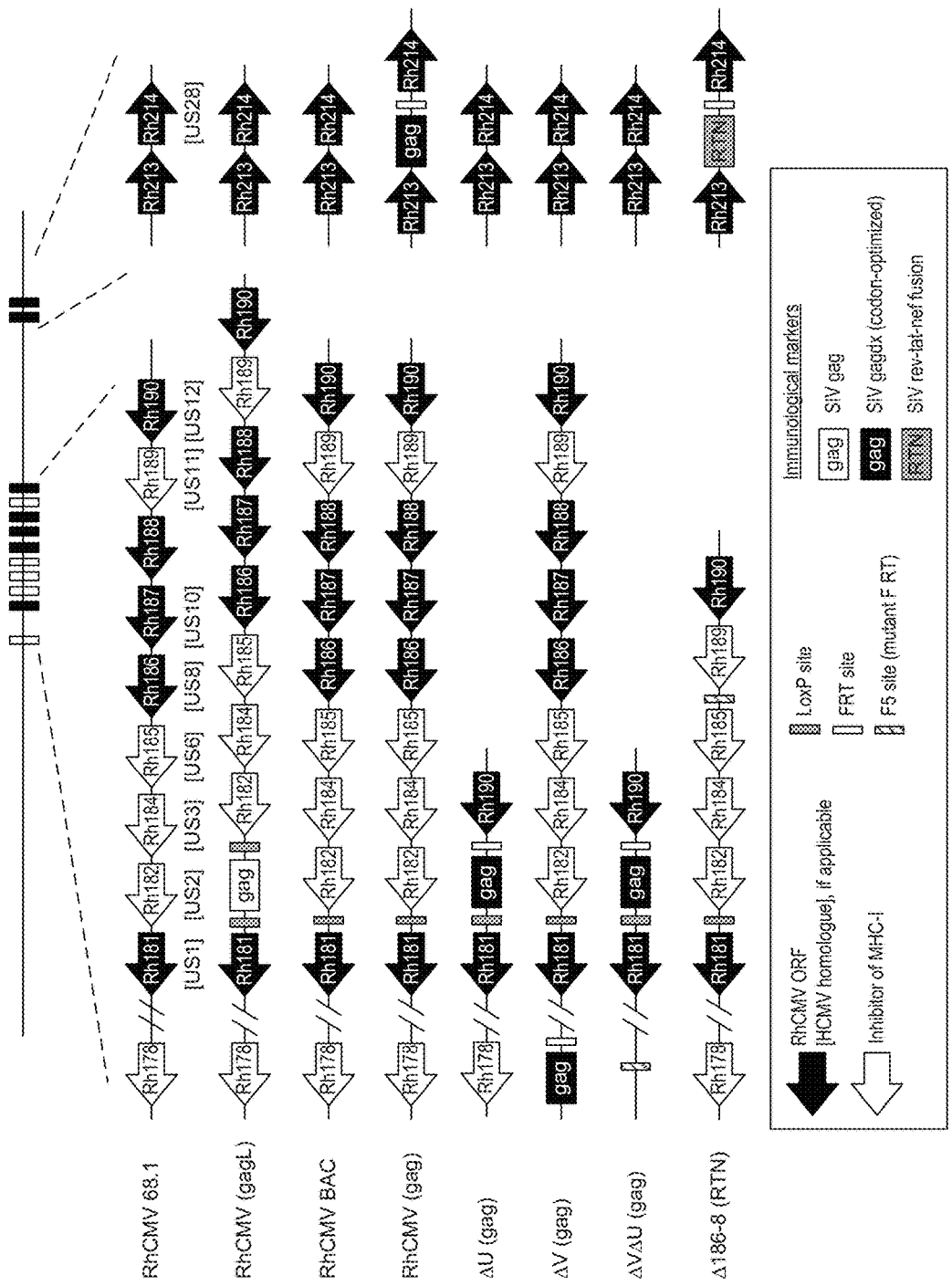
FIG. 5. Diagram of viruses used in Example 1. The deletion strategy is described in (S. G. Hansen et al. *Science* 328, 5974 (2010)). Regions of the genome that were altered to create mutant viruses are shown in detail. All RhCMV ORFs are depicted as arrows that correspond to the direction of the ORF within the genome. White arrows represent genes that downregulate MHC class I. The RhCMV nomenclature is used for all ORFs (S. G. Hansen et al. *J Virol* 77, 6620 (2003)). For ORFs with homology to HCMV genes the name of the corresponding HCMV homologue is shown in brackets.
Figures 8A, 8B:
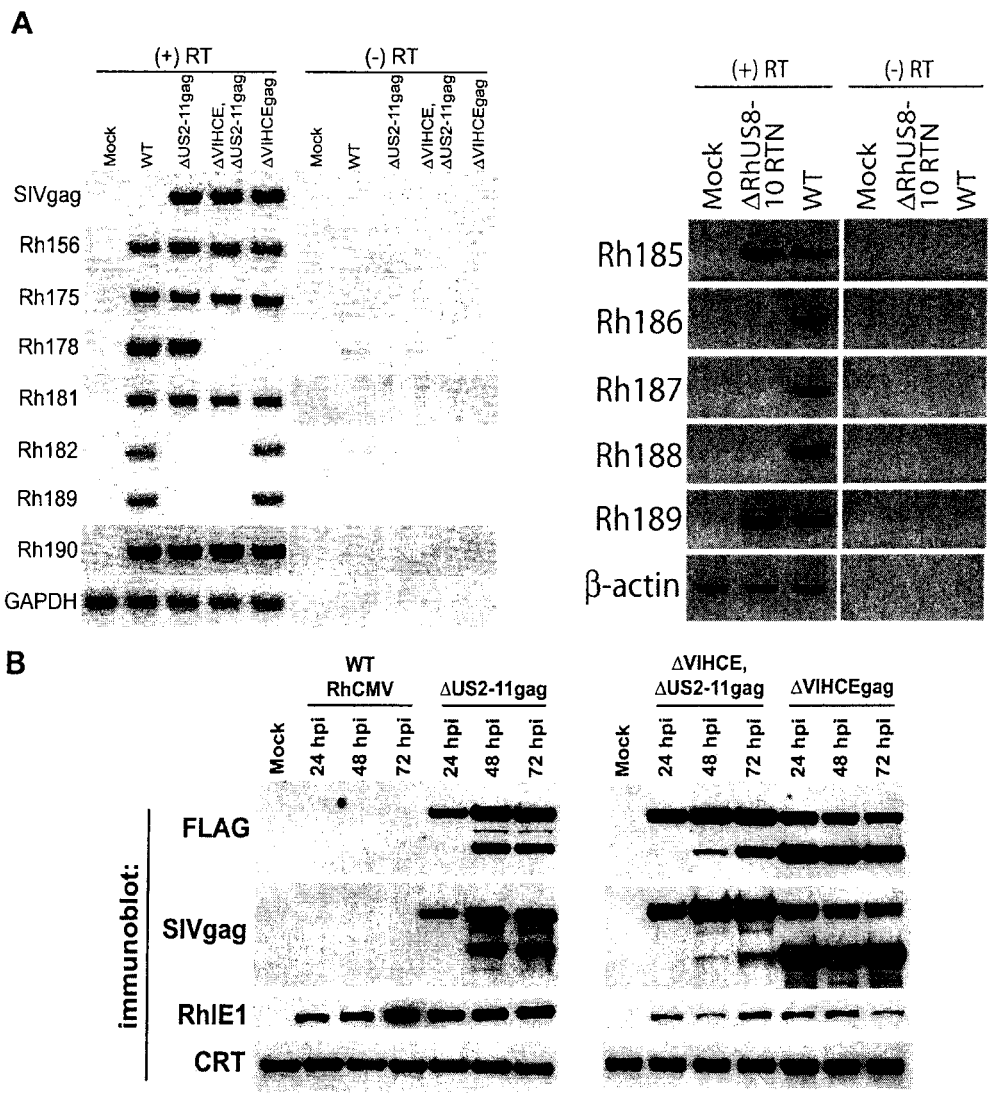
FIGS. 8A-8C. Characterization of recombinant RhCMVs in vitro. A) RT-PCR. TRFs were infected at MOI=1 with the indicated virus and total RNA was harvested at 24 hpi. cDNA was synthesized by random hexamer priming, and transcripts were amplified with primers specific for the ORFs indicated on the left. Genes flanking the deleted regions were included to detect possible changes in transcription due to the deletions. WT=BACderived wild type RhCMV. RT=reverse transcriptase. B) Expression of SIVgag by recombinant viruses. Immunoblot analysis of FLAG-tagged SIVgag expressed by the indicated viruses. TRFs were infected at MOI=1 and total lysate was harvested at the indicated times. Antibodies are described in Example 1. CRT=calreticulin. C) Multi-step viral growth. TRFs were infected at MOI=0.1 and supernatant was titered by plaque assay at the indicated times. Growth is compared to BAC-derived wild type RhCMV.
Figure 8C:
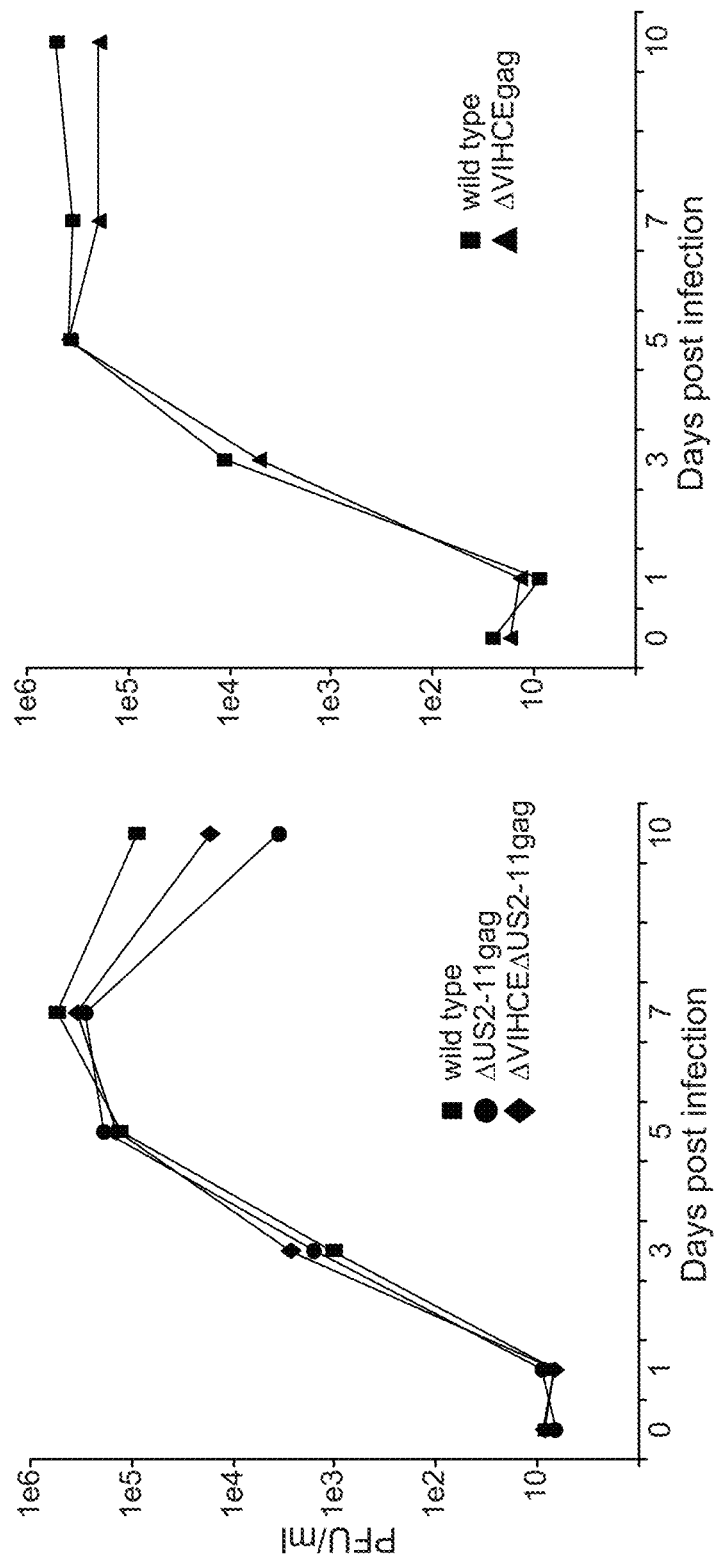
Figure 9:
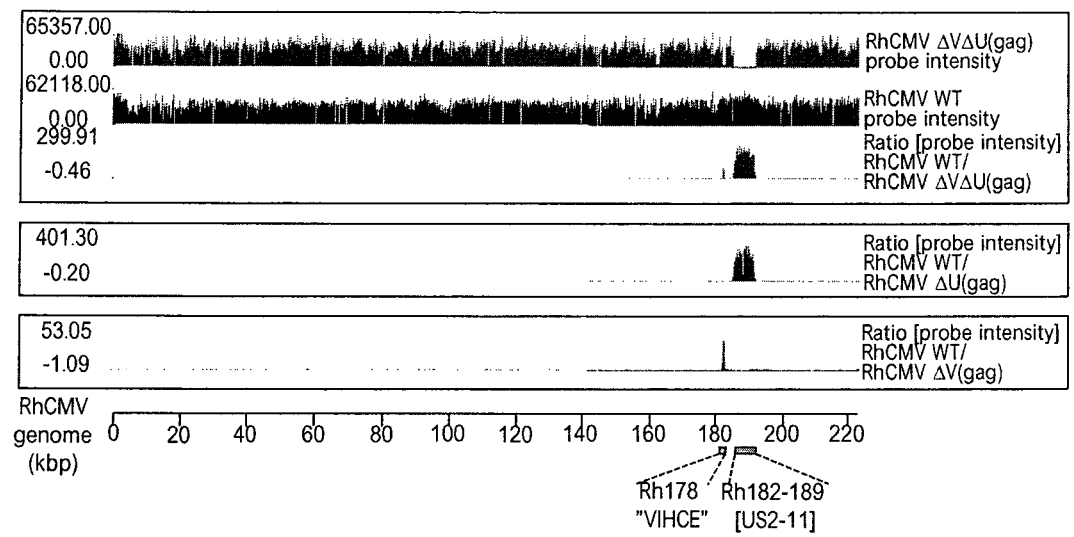
FIG. 9. Comparative genome sequencing of recombinant RhCMV. The top panel shows the probe signal intensities for labeled genomic DNA fragments obtained from the co-hybridization of ΔVIHCEΔUS2-11(gag) (ΔVΔU, Cy5 channel, green) and BACderived RhCMV (WT, Cy3 channel, blue) to the RhCMV-DNA-microarray of overlapping oligonucleotides. Differences in hybridization signals between the reference and test genomes are shown in red as the ratio of probe intensities for WT versus ΔVIHCEΔUS2-11(gag). The second and third panels show the ratios in probe intensities for WT versus ΔUS2-11(gag) (ΔU) and WT versus ΔVIHCE(gag) (ΔV). The bottom panel shows the nucleotide numbers of the RhCMV genome, depicted in 20 kbp increments. Also indicated are the positions of the VIHCE and US2-11 deletions. Positive red spikes represent signals that are present in the reference, but absent in the deletion viruses. These spikes correspond to the expected location of the deletions. Note that significant differences outside the deleted regions were not observed, indicating that the genomes of the deletion viruses are identical to that of the parental BAC in all but the deleted regions.

To determine whether MHC-I interference and CTL evasion played a role in the ability of CMV to superinfect CMV+ animals, Applicants replaced the entire RhUS2-11 region with a SIVgag expression cassette using bacterial artificial chromosome (BAC) mutagenesis, resulting in virus ΔUS2-11(gag). Applicants also deleted Rh178 to generate ΔVIHCEΔUS2-11(gag) (FIG. 5). Applicants previously showed that MHC-I expression is partially restored upon US2-11 deletion, whereas additional deletion of Rh178 fully restores MHC-I expression in RhCMV-infected fibroblasts (C. J. Powers, K. Früh, *PLoS Pathog.* 4, e1000150 (2008)). In vitro analysis showed that all viruses were deleted for the targeted RhCMV open reading frames (ORFs), did not contain any unwanted mutations, and replicated comparably to wild-type RhCMV (FIGS. 8 and 9). First, Applicants examined whether these viruses were able to infect animals that were CMV-naïve as shown by a lack of CMV-specific T cell responses (Table 1B). Three groups of animals were challenged with $10^7$ PFU of ΔUS2-11(gag) (n=2), ΔVIHCEΔUS2-11(gag) (n=2), or BAC-derived (wild-type) RhCMV(gag) (n=2). T cell responses against both CMV and SIVgag in PBMC and against SIVgag in BAL were comparable between animals infected with the deletion mutants and the wild-type RhCMV(gag) control (FIG. 2A). Moreover, all animals secreted SIVgag-expressing virus from day 56 onward for the duration of the experiment (>700 days) (FIG. 2B). Polymerase chain reaction (PCR) analysis of DNA isolated from urine cocultured virus at day 428 confirmed that the secreted viruses lacked the respective gene regions and were able to persist in the host (FIG. 2C). Together these results show that viral MHC-I interference is dispensable for primary infection and the establishment and maintenance of persistent infection, despite the development of a substantial CMV-specific T cell response.

To examine whether viral MHC-I interference was required for superinfection of RhCMV+RM, Applicants challenged two cohorts of four naturally infected RM each with $10^7$ PFU of ΔVIHCEΔUS2-11(gag) or RhCMV(gag).

Figure 3A:
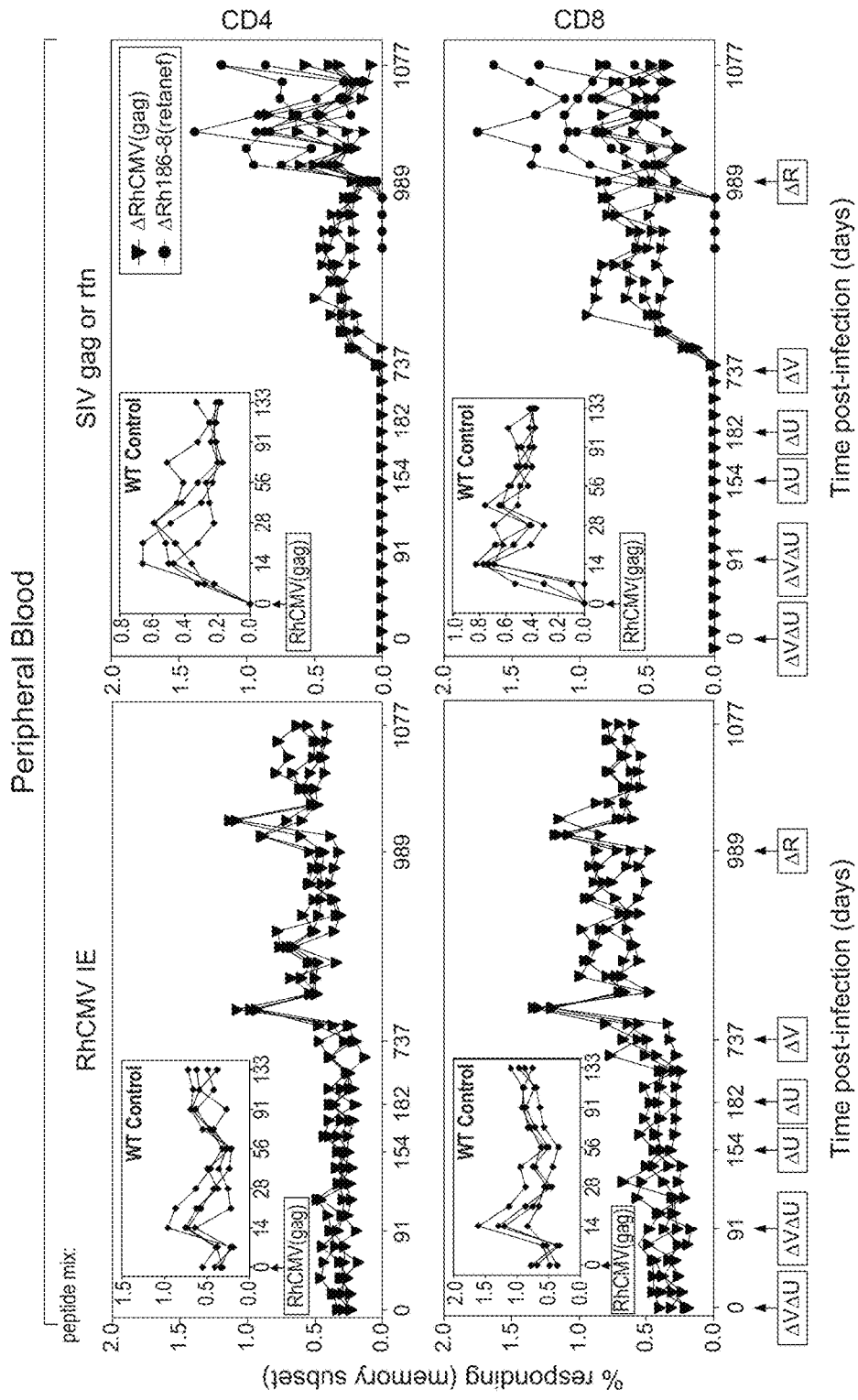
FIGS. 3A-3D. US2-11-deleted RhCMV is unable to superinfect RhCMV+ rhesus macaques. (A) A cohort of four RhCMV+RM was inoculated subcutaneously with 107 PFU of ΔVIHCEΔUS2-11(gag) (ΔVΔU) at days 0 and 91. The CD4+ and CD8+ T cell response to SIVgag or RhCMV-IE was monitored by flow cytometric analysis of ICCS for CD69, TNF-α, and IFN-γ in PBMC. The percentage of the responding, specific T cells within the overall memory subset is shown for each time point. At day 154 and again on day 224, the same cohort was inoculated with $10^7$ PFU of ΔUS2-11(gag) (ΔU), and RhCMV-IE and SIVgag-specific T cell responses were monitored bi-weekly. At day 737, the cohort was inoculated with ΔVIHCE(gag) (ΔV), and the T cell response was monitored as before. At day 989, the cohort was inoculated with ΔRh186-8(retanef) (ΔR). Besides SIVgag, a T cell response to SIVrev/nef/tat was detected by ICCS in all four animals (lines with black circles) using corresponding overlapping peptides. (Inset) A separate cohort of four animals was infected with wild-type RhCMV(gag), and the RhCMV-IE and SIVgag-specific $CD4^+$ and $CD8^+$ T cell response was monitored as described above at the indicated time points for 133 days. (B) The $CD4^+$ and $CD8^+$ T cell response to SIVgag in BAL was measured in parallel to the PBMC T cell responses shown in (A). (C) RhCMV secreted in the urine collected from the cohort infected with RhCMV(gag), or deletion viruses ΔVIHCEΔUS2-11(gag) or ΔUS2-11(gag), labeled ΔCMV. Virus was isolated at the indicated days by coculture with telomerized rhesus fibroblasts (TRFs), and cell lysates were probed for expression of SIVgag by immunoblot. (D) Expression of RhCMV-IE2, SIVgag, and SIVretanef by virus secreted in urine collected at the indicated days. Note that all animals were IE2-positive at the onset of the experiment, confirming their RhCMV-positive T cell status (Table 1D).
Figure 3B:
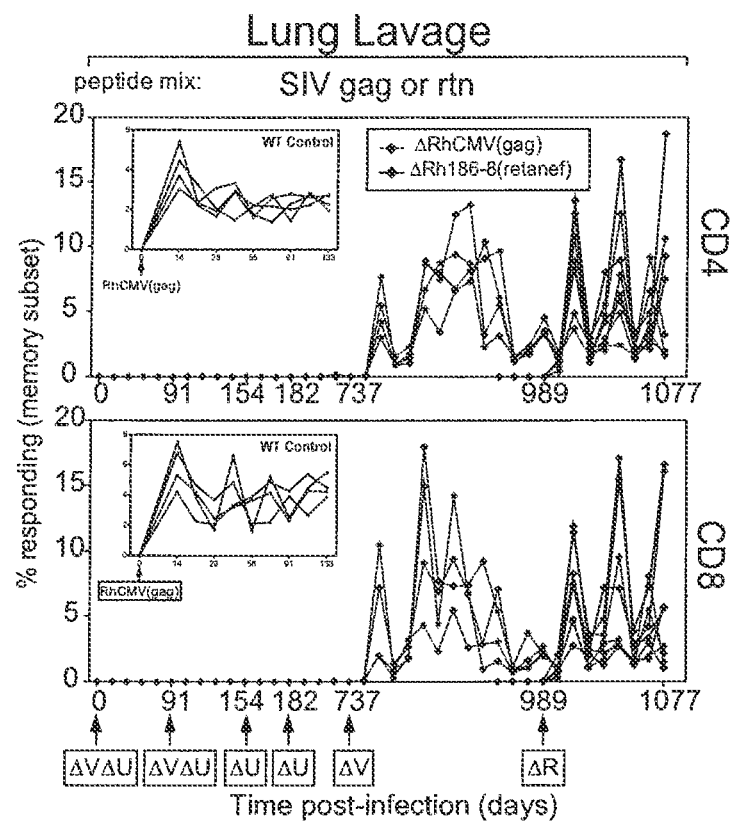
Figure 3C:
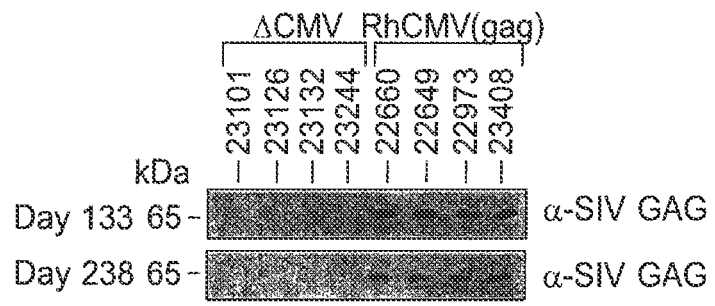

All animals displayed immediate early gene (IE)—specific CD4+ and CD8+ T cell responses before challenge (FIG. 3A and Table 1C). In keeping with previous results (S. G. Hansen et al., *Nat. Med.* 15, 293 (2009)), RM inoculated with wild-type RhCMV(gag) displayed boosting of the RhCMV-specific T cell response and developed a SIVgag-specific immune response (FIGS. 3, A and B, insets). They also secreted SIVgag-expressing virus (FIG. 3C). In contrast, Applicants did not detect SIVgag-specific T cell responses in PBMC or BAL in RM inoculated with ΔVIHCEΔUS2-11(gag), even after repeated inoculation (FIGS. 3, A and B), and SIVgag-expressing virus was not detected in secretions (FIG. 3C). These results suggested that MHC-I interference was essential for superinfection. Inoculation of the same animals with ΔUS2-11(gag) and, later, ΔVIHCE(gag) demonstrated that superinfection required the conserved US2-11 region but not the VIHCE region. The development of SIVgag-specific CD4+ and CD8+ T cell responses in blood and BAL (FIGS. 3, A and B), as well as the boosting of preexisting RhCMV-specific CD4+ and CD8+ T cell responses in blood (FIG. 3A), or shedding of SIVgag-expressing RhCMV (FIG. 3D) were only detectable after challenge with ΔVIHCE(gag) but not with ΔUS2-11(gag).

Figure 3D:
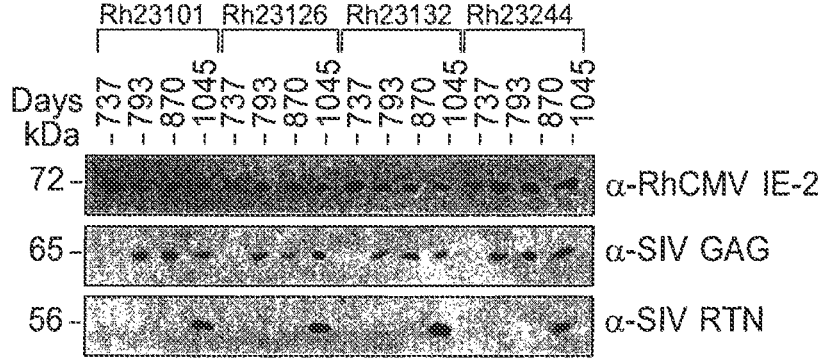

Applicants' results show that genes within the US2-11 region are essential for superinfection, which is consistent with the known function of US2, US3, US6, and US11 as inhibitors of MHC-I antigen presentation. There are, however, three genes of unknown function (Rh186 to Rh188) encoded between US6 and US11. Rh186 and Rh187 are most closely related to the HCMV glycoproteins US8 and US10, respectively (N. T. Pande et al. *J. Virol.* 79, 5786 (2005)), whereas Rh188 is an uncharacterized RhCMV-specific ORF. Although binding of HCMV-US8 and US10 to MHC-I has been reported, it is unclear whether this affects antigen presentation because MHC-I surface expression is not reduced by US8 or US10 from either HCMV or RhCMV (N. T. Pande et al. *J. Virol.* 79, 5786 (2005), R. S. Tirabassi, H. L. Ploegh, *J. Virol.* 76, 6832 (2002) and M. H. Furman et al., *J. Virol.* 76, 11753 (2002)). To determine whether Rh186, Rh187, or Rh188 are required for superinfection, Applicants generated deletion virus ΔRh186-8. To enable us to monitor superinfection by this recombinant in the same cohort of animals that had already been reinfected with ΔVIHCE(gag), Applicants applied a distinct immunological marker, SIVretanef, a fusion-protein consisting of SIV proteins rev, tat, and nef (S. G. Hansen et al., *Nat. Med.* 15, 293 (2009)). ΔRh186-8(retanef) is deleted for Rh186-188 and contains the Retanef expression cassette between the ORFs Rh213 and Rh214 (FIG. 5). Applicants inoculated the same cohort with ΔRh186-8(retanef) and monitored the T cell response to this fusion protein as well as to RhCMV-IE and SIVgag using corresponding peptides. As shown in FIGS. 3, A and B, all four RM developed a SIVretanef-specific T cell response within 2 weeks post-challenge, indicating successful superinfection. Moreover, virus expressing SIVretanef was shed in the secretions of infected animals together with SIVgag-expressing ΔVIHCE(gag) (FIG. 3D). Applicants thus conclude that the Rh186-8 region is dispensable for superinfection.

Figure 4A:
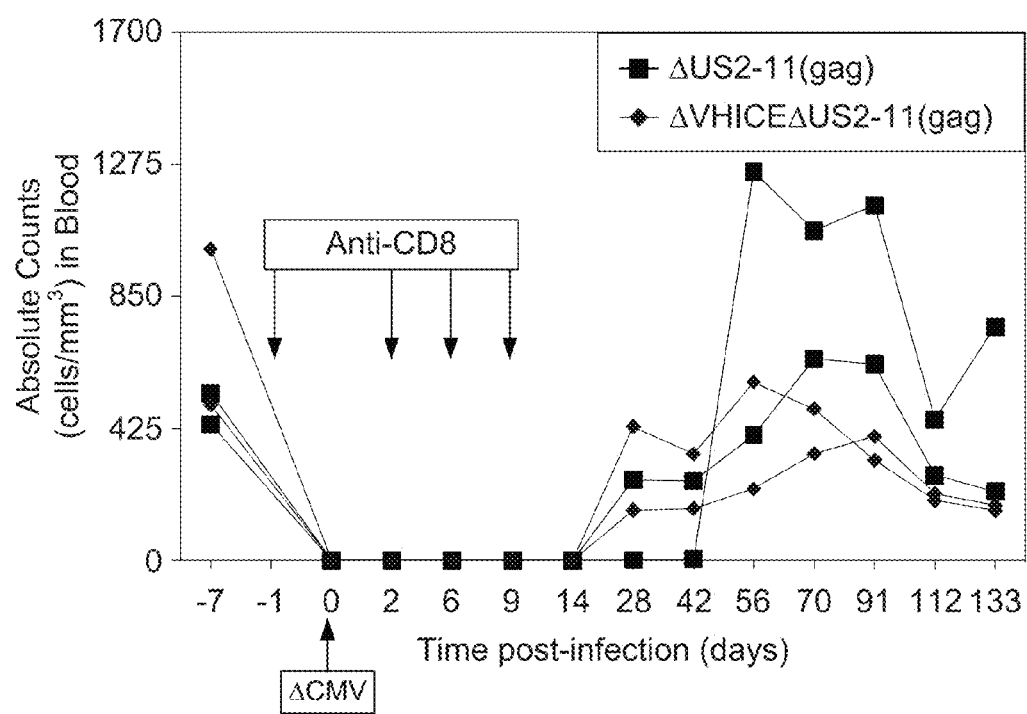
FIGS. 4A-4D. $CD8^+$ T cells protect rhesus macaques from infection by RhCMV lacking MHC-I inhibitors. (A) Four CMV-positive RM were treated at the indicated days with CM-T807, an antibody to CD8, before and after inoculation with 107 PFU of ΔVIHCEΔUS2-11(gag) (two animals, lines with black diamonds) or ΔUS2-11(gag) (two animals, lines with black squares). The absolute counts of $CD8^+$ T cells in the blood of each animal are shown over time. (B) The presence of $CD4^+$ and $CD8^+$ T cell populations in PBMC of one representative animal is shown for the indicated days. (C) SIVgag-specific $CD4^+$ and $CD8^+$ T cell responses in PBMC and BAL of $CD8^+$ T cell-depleted animals were monitored by ICCS for CD69, TNF-α, and IFN-γ and are shown as a percentage of total memory $CD4^+$ or $CD8^+$ T cells. Note the delayed appearance of SIVgag-specific $CD8^+$ T cells. (D) Expression of SIVgag or IE2 by RhCMV secreted in the urine of animals infected upon $CD8^+$ depletion.
Figure 4B:
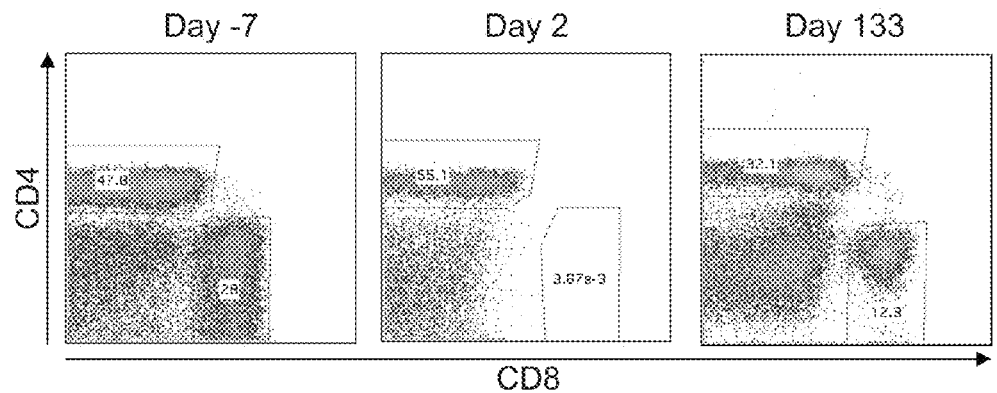
Figure 4C:
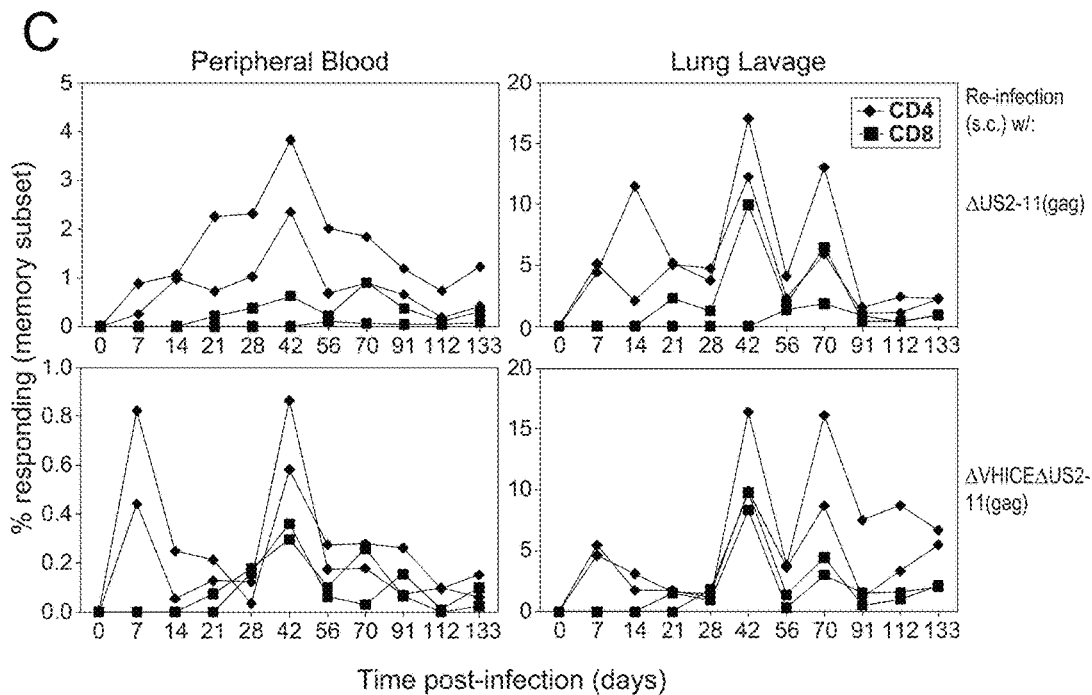
Figure 4D:
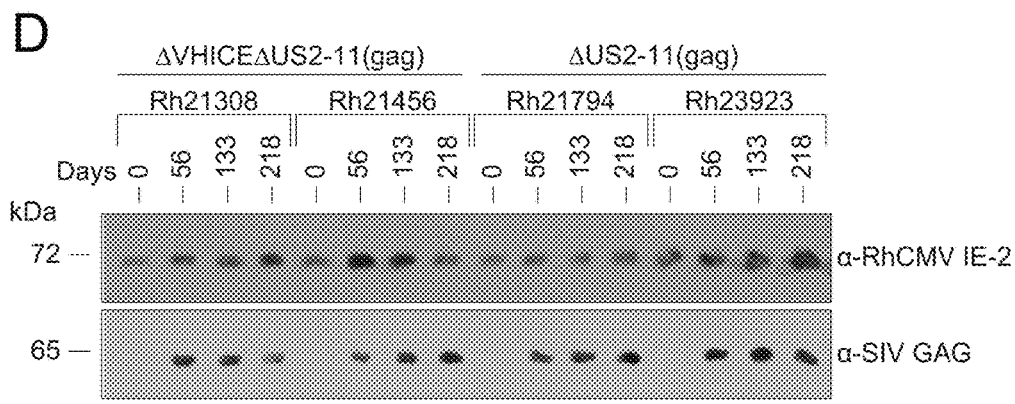

Together, Applicants' results suggested that RhCMV was unable to superinfect in the absence of the homologs of US2, US3, US6, and US11 because the virus was no longer able to avoid elimination by CTL. To further examine this hypothesis, a new group of RhCMV+RM (Table 1D) was depleted for CD8+ lymphocytes by treatment with cM-T807, a humanized monoclonal antibody to CD8, before superinfection with ΔUS2-11(gag) or ΔVIHCEΔUS2-11 (gag). Flow cytometric analysis of total CD8+ T cells revealed that depletion was extensive, but transient, with detectable CD8+ T cell recovery beginning on day 21 after challenge (FIGS. 4, A and B). Upon inoculation with ΔUS2-11(gag) or ΔVIHCEΔUS2-11(gag), SIVgag-specific CD4+ T cell responses were recorded as early as day 7 post-challenge, showing the ability of the deletion viruses to superinfect these animals (FIG. 4C). Moreover, SIVgag-specific CD8+ T cells were observed within the rebounding CD8+ T cells in blood and BAL at day 21 in two RM and at day 28 in a third; in the fourth RM, such responses were only observed in BAL after day 56. From these data, Applicants conclude that CD8+ lymphocytes, most likely CD8+ T cells, were essential for preventing superinfection by ΔUS2-11 virus, strongly indicating that the MHC-I inhibitory function of these molecules is necessary for superinfection of the CMV-positive host. Notably, CMV-specific CD8+ T cells were unable to eliminate RhCMV lacking MHC-I inhibitors once persistent infection had been established (FIG. 4D), providing additional evidence that persistent infection is insensitive to CD8+ T cell immunity, even when the ability of the virus to prevent MHC-I presentation is compromised.

Applicants' data imply that T cell evasion is not required for establishment of primary CMV infection or once the sites of persistence (e.g., kidney and salivary gland epithelial cells) have been occupied, but rather it is essential to enable CMV to reach these sites of persistence from the peripheral site of inoculation in the CMV-immune host. One possible scenario is that viral infection of circulating cells, for example, monocytes, may succeed only if the virus prevents elimination of these cells by virus-specific CTLs. More work, however, will be required to identify the cell type supporting superinfection.

Although the biochemical and cell biological functions of US2, US3, US6, and US11 have been studied extensively (C. Powers et al. Curr. Top. Microbiol. Immunol. 325, 333 (2008)), their role in viral pathogenesis had remained enigmatic. Analogous gene functions in murine CMV (MCMV) had been similarly found to be dispensable for both primary and persistent infection (A. K. Pinto, A. B. Hill, Viral Immunol. 18, 434 (2005)), although reduced viral titers have been reported for MCMV deleted for these genes (A. Krmpotic et al., J. Exp. Med. 190, 1285 (1999)). Thus, the reason all known CMVs dedicate multiple gene products to MHC-I downregulation had remained elusive. Applicants' current results now identify a critical role for these immunomodulators to enable superinfection of the CMV-positive host. Furthermore, these results suggest that the ability to superinfect is an evolutionary conserved function among CMVs and therefore might play an important role in the biology of these viruses. Superinfection could promote the maintenance of genetic diversity of CMV strains in a highly infected host population, which could provide an evolutionary advantage. However, there is another possibility. CMV is a large virus with thousands of potential T cell epitopes and therefore a high potential for CD8+ T cell cross-reactivity (L. K. Selin et al., Immunol. Rev. 211, 164 (2006)). Indeed, in a study of pan-proteome HCMV T cell responses, 40% of HCMV seronegative subsets manifested one or more cross-reactive CD8+ T cell responses to HCMV-encoded epitopes (A. W. Sylwester et al., J. Exp. Med. 202, 673 (2005)). As CMV recognition by cytotoxic T cells appears to effectively block primary CMV infection, individuals with cross-reactive CD8+ T cell immunity might be resistant to CMV. Thus, US2-11 function may be necessary to evade such responses and establish infection in this large population of individuals that might otherwise be CMV-resistant.

Applicants' results also may explain why, so far, it has not been possible to develop a vaccine that efficiently protects humans from HCMV infection. Although antibody-mediated mucosal immunity might reduce the rate of superinfection (S. A. Plotkin et al. J. Infect. Dis. 159, 860 (1989) and L. K. Selin et al., Immunol. Rev. 211, 164 (2006)), once this layer of defense is breached, CMV-specific CTLs seem to be unable to prevent viral dissemination, due to MHC-I downregulation by US2-11. Thus, although CMV vaccines might be able to limit CMV viremia and associated morbidity, this MHC-I interference renders it unlikely that sterilizing protection against CMV infection is an achievable goal.

Antibodies.

The following antibodies were used for immunoblots: anti-Gag Ab from the NIH AIDS Repository for all SIVgag expressing RhCMV recombinants or anti-FLAG (Sigma) for FLAGtagged SIVgag; anti-V5 (Invitrogen) for V5-tagged SIVretanef and anti-calreticulin (SPA-601, StressGen) for control. Anti-RhCMV-IE1 was described previously (S. G. Hansen et al., Nat Med 15, 293 (2009)). The following antibodies used in flow cytometry were from BD Bioscience: L200 (CD4; AmCyan); SP34-2 (CD3; Alex700, PacBlu); SK1 (CD8alpha; TruRed); DX2 (CD95; PE); 25723.11 (IFN-γ; APC); 6.7 (TNF; FITC). The following antibodies were obtained from Beckman Coulter: CD28.2 (CD28; PE-Texas Red); L78 (CD69; PE).

Construction of Recombinant RhCMV.

All recombinant viruses used in this study were derived from strain RhCMV 68-1 (S. G. Hansen et al. J Virol 77, 6620 (2003)) and are graphically depicted in FIG. 5. RhCMV(gagL) was generated by replacing the loxP-flanked enhanced green-fluorescent protein (EGFP) in RhCMV-EGFP (W. L. Chang et al. J Virol 76, 9493 (2002)) with a loxP-flanked expression cassette for SIVmac239-gag under control of the EF1α-promoter by in vivo recombination in tissue culture. All other recombinant viruses were created using the RhCMV bacterial artificial chromosome (RhCMV-BAC) (W. L. Chang, P. A. Barry, J Virol 77, 5073 (2003)) (FIG. 5). The BAC-cassette was inserted between the RhCMV homologs of US1 and US2 and self-excises via Cre-recombinase (W. L. Chang, P. A. Barry, J Virol 77, 5073 (2003)). Recombinant virus RhCMV(gag) contains a codon-optimized, FLAG-tagged SIVmac239-gag sequence under control of the EF1α-promoter inserted between ORFs R213 and R214 (S. G. Hansen et al., Nat Med 15, 293 (2009)). Deletion of the US2-11 region by homologous recombination (ET cloning) with an FRT-flanked Kanamycin-resistance (KanR) cassette was described previously (C. J. Powers, K. Früh, PLoS Pathog 4, e1000150 (2008)). ΔUS2-11 (gag) was created by replacing the entire Rh182-189 region (base pairs 184489-191243) using the same primers and mutagenesis strategy as before (C. J. Powers, K. Früh, PLoS Pathog 4, e1000150 (2008)) except that the inserted fragment harbored both the KanR cassette and the codon-optimized, FLAG-tagged SIVgag-cassette. The KanR-cassette was removed by arabinose-induced FLP-expression (C. J. Powers, K. Früh, PLoS Pathog 4, e1000150 (2008)). ΔVIHCEΔUS2-11(gag) was created by subsequent deletion of Rh178 (VIHCE; base pairs 181320-182060). Since ΔUS2-11(gag) contains a single FRT recombination site from KanR-excision, Applicants used a KanR cassette flanked by the F5-mutant FRT sequence for deletion of VIHCE. This prevents potential recombination between new and existing FRT sites when creating dual-recombinants. The mutant FRT-flanked KanR cassette was obtained from plasmid pOri6K-F5 (E. M. Borst, M. Messerle, *J Virol* 79, 3615 (2005)) using primers 5'-TAAAAGTGTCGGAT-GAATGTGCGGCGCCAACACGCAGACCGAAAAGT-GCCACCTGC AGAT-3' (SEQ ID NO: 1) and 5'-GCCT-GACTGATGACTAGTCATCGCACGCCTCTTCCCGCC CCAGGAACACTTAACGGC TGA-3' (SEQ ID NO: 2). ΔVIHCE was created by replacing base pairs 181320-182060 with the SIVgag expression cassette using primers 5'-TTTGTTCGTATAAAAGTGTCGGATGAATGTGCG-GCGCCAACACGCAGACCGTAAAA CGACGGCCAGT-3' (SEQ ID NO: 3) and 5'-CGCTCCCTCGGCCTGACT-GATGACTAGTCATCGCACGCCTCTTCCCGCCCGTA TGTTG TGTGGAATTGTGAG-3' (SEQ ID NO: 4). ΔRh186-8(retanef) was created from previously described V5-tagged RhCMV(retanef) (S. G. Hansen et al., *Nat Med* 15, 293 (2009)) by deletion of base pairs 187934-190031 using the KanR-cassette flanked by the F5-mutant FRT sites. All recombinant BACs were verified for correct deletions by restriction digest, southern blot and sequence analysis of the insert-borders. RhCMV virus was reconstituted by electroporation of telomerized rhesus fibroblasts (TRFs) (V. Kirchoff et al. *Arch Virol* 147, 321 (2002)).

Characterization of Recombinant Viruses by RT-PCR.

Resulting viruses were plaque-purified and characterized for gene expression of deleted and flanking genes by RT-PCR (FIG. 8). TRFs were infected at MOI=1 and total RNA was collected at 24 hpi using RNeasy mini kit (Qiagen) according to the manufacturer's instructions. 4 μg of RNA was treated with DNAse I (Applied Biosystems) for 30 min at 37° C. 1 μg of DNAse-treated RNA was used in a 20 μl reverse transcription reaction containing 50 ng random hexamers, 0.5 mM dNTPs, 10 mM DTT, and 1 μl superscript III RT in 1×RT buffer (Invitrogen) for 1 hour at 37° C. 1 μl of the RT reaction was used for semi-quantitative PCR with Platinum taq polymerase (Invitrogen) under the following conditions: 1× platinum taq buffer, 1.5 mM $MgCl_2$, 0.2 mM dNTPs, 0.5 μM each primer, and 1.5 U polymerase. 35 cycles of amplification was performed under the following conditions: 94° C. for 30 sec, 55° C. for 30 sec, and 72° C. for 15 sec. The following primer pairs were used: SIVgag 5'-ACCCACAACCAGCTCCACAA-3' (SEQ ID NO: 5) and 5'-ATCCACTGGATCTGTTCGTCAA-3' (SEQ ID NO: 6); Rh156 5'-CAATGAGGATAGGTTCCCAGTTG-3' (SEQ ID NO: 7) and 5'-GCCAGTGGGATGTCAGTACCA-3' (SEQ ID NO: 8); Rh175 5'-CTAGCAGTACT-GAGAGCTAG-3' (SEQ ID NO: 9) and 5'-TCACGC-CAATCGACAGTGCACG-3' (SEQ ID NO: 10); Rh178 5'-CGCATACTGACAAGCCAGGGC-3' (SEQ ID NO: 11) and 5' GCGAAAGAAGGTGCACATGAC-3' (SEQ ID NO: 12); Rh181 5'-CCTTACGGAGTCGCTCGTTGAC-3' (SEQ ID NO: 13) and 5'-TGTGTCGTCTCTTTCTCCGCAG-3' (SEQ ID NO: 14); Rh182 5'-GATTTTCGTTGAACAT-GTCCGAC-3' (SEQ ID NO: 15) and 5'-GTTATGTGTCA-GAAAGTCCG GCT-3' (SEQ ID NO: 16); Rh189 5'-TGCT-TCGTCCTGGTGCTGT-3' (SEQ ID NO: 17) and 5'-TTAGCAGTTTCATGGTTG CGA-3' (SEQ ID NO: 18); Rh190 5'-GAAATGGATAGCGGTGCTCAC-3' (SEQ ID NO: 19) and 5'-CAGACAACAGGTTG TTCAGG-3' (SEQ ID NO: 20); GAPDH 5' 5'-GCACCACCAACTGCTTAG-CAC-3' (SEQ ID NO: 21) and 5'-TCTTCTGGGTGG CAGTGATG-3' (SEQ ID NO: 22). For characterization of the RhΔ186-8(retanef) virus, RT-PCR was performed as described above with the following primer pairs: Rh185 5'-AGCGTAGCTCCTCCATACCG CT-3' (SEQ ID NO: 23) and 5'-ATCCGCGGACTGTTTGGGTGT-3' (SEQ ID NO: 24); Rh186 5'-GCTTCTTCCAGAAGTTGCATAG-GATGA-3' (SEQ ID NO: 25) and 5'-CGACTTTCCGGATC-CTACGTGGC-3' (SEQ ID NO: 26); Rh187 5'-CCATAGC-CATGCAATGGTCGCA-3' (SEQ ID NO: 27) and 5'-GCGCCATCCCGTGTTACCCC-3' (SEQ ID NO: 28); Rh188 5'-AGAGCTCTGGTCGTCGGCGT-3' (SEQ ID NO: 29) and 5'-TGGCTGGCCACCAGATGGATGT-3' (SEQ ID NO: 30); Rh189 5'-AACCAGTAGGAGCGC-CCGGT-3' (SEQ ID NO: 31) and 5'-CGACTCCTGCAT-GCTTACTGGGGA-3' (SEQ ID NO: 32); β-actin 5'-TCACCCACACTGTGCCCATCTACGA-3' (SEQ ID NO: 33) and 5'-CAGCGGAACCGCTCATTGCCAATGG 3' (SEQ ID NO: 34).

Characterization of Recombinant Viruses by Comparative Genome Sequencing.

To confirm that the genetic manipulation of the RhCMV genome did not introduce unwanted mutations outside the regions targeted for deletion, Applicants used Comparative Genome Sequencing (CGS) to compare the deletion viruses against RhCMV-BAC. Single nucleotide differences between reference and test strains of herpesviruses may be identified with CGS (O. Timoshenko et al. *J Med Virol* 81, 511 (2009) and D. Estep et al. *J Virol* 81, 2957 (2007)). CGS of viral DNA was performed using a microarray hybridization-based technique with services provided by NimbleGen Systems, Inc. (Madison, Wis.). A RhCMV comparative genomic hybridization array was created using the published sequence for RhCMV 68.1 (S. G. Hansen et al. *J Virol* 77, 6620 (2003)). Oligonucleotides that comprised this array were designed to be between 29 and 32 bp, with overlapping sequences of at least 7 bp, with coverage of both strands of the RhCMV 68.1 genome. Viral DNA was isolated using standard methods from a) parental RhCMV-BAC (W. L. Chang, P. A. Barry, *J Virol* 77, 5073 (2003)), b) ΔVIHCEΔUS2-11(gag), c) ΔUS2-11(gag), or d) ΔVIHCE (gag). Briefly, virus was produced in telomerized rhesus fibroblasts (TRFs), supernatants were collected and, after proteinase K treatment, DNA was isolated by cesium chloride gradient centrifugation. The resulting viral DNA was ethanol precipitated and brought to a final concentration of 1 μg/μl. Viral DNA was fragmented and labeled with Cy3 (RhCMV-BAC as reference) or Cy5 (deletion viruses). Labeled reference and test viral DNA probes were co-hybridized to the tiling arrays and the Cy3 and Cy5 signals were scanned. SignalMap software (NimbleGen Systems, Inc.) was used to analyze all CGS data.

Rhesus Macaques.

A total of 28 purpose-bred juvenile and adult male rhesus macaques (RM) (*Macaca mulatta*) of Indian genetic background were used in this study, of which four animals were specific pathogen-free (SPF) animals and lacked RhCMV-specific T cells and antibodies. All other animals used in the study acquired RhCMV naturally while in the colony. The presence or absence of RhCMV-specific T cell responses was confirmed by intracellular cytokine staining of RhCMV Ag-stimulated PBMC (Table 1). All RM were free of cercopithicine herpesvirus 1, D-type simian retrovirus, simian T-lymphotrophic virus type 1 and SIV infection. Animal protocols were approved by the Oregon National Primate Research Center Animal Care and Use Committee, under the standards of the US National Institutes of Health Guide for the Care and Use of Laboratory Animals. Animals were inoculated with 102-107 PFU of recombinant virus subcutaneously. For CD8+ cell depletion, RM were treated with 10, 5, 5 and 5 mg per kg body weight of the humanized monoclonal antibody cM-T807 (J. E. Schmitz et al., *Am J*

*Pathol* 154, 1923 (1999)) one day before viral infection and on days 2, 6, and 9 post infection, respectively.

Virological Analysis of Rhesus Macaques.

Isolation and co-culture of virus from urine and buccal swabs was performed as described previously (S. G. Hansen et al., *Nat Med* 15, 293 (2009)). Briefly, virus was concentrated from cleared urine and co-cultured with rhesus fibroblasts and cell lysates were collected after cytopathic effects were observed or after 28 days.

PCR Analysis of Co-Cultured Virus.

Supernatant from cells prepared from urine co-cultures was used to infect fresh TRFs. When the cells reached 90-100% cytopathic effect, total DNA was collected. Cells were scraped and lysed in 300 µl of a buffer containing 10 mM Tris-HCl, pH 8.5, 5 mM EDTA, 0.2M NaCl, and 0.2% SDS for 5 minutes at 60° C., followed by addition of 10 µg RNAse A and 5 µl proteinase K (Fermentas, ~20 mg/mL) for 1 hour at 60° C. Protein was then precipitated with 150 µl of 5M NaCl and incubated on ice for 5 min. Debris was pelleted at 16000×g for 15 min, supernatant removed, and DNA precipitated with 450 µl isopropanol. 50 ng of DNA was used for PCR analysis under the following conditions: 1× platinum taq buffer, 1.5 mM $MgCl_2$, 0.2 mM dNTPs, 0.5 µM each primer, and 1.5 U platinum taq polymerase. 35 cycles of amplification was performed under the following conditions: 94° C. for 30 sec, 55° C. for 30 sec, and 72° C. for 80 sec. The following primer pairs were used: Rh156 5'-GTTTAGGGAACCGCCATTCTG-3' (SEQ ID NO: 35) and 5'-GTATCCGCGTTCCAATGCA-3' (SEQ ID NO: 36); SIVgag 5'-ACCCACAACCAGCTCCACAA-3' (SEQ ID NO: 37) and 5'-CTGCCATTAATCTAGC-3' (SEQ ID NO: 38); Rh189 5'-CTCTGGTCGTCGGCGTATG-3' (SEQ ID NO: 39) and 5'-TGCTTCGTCCTGGTGCTGT-3' (SEQ ID NO: 40); Rh180 5'-GGCAAGGGAGCTCAATGGAAAC-3' (SEQ ID NO: 41) and 5'-TCAACGCCCATCTAAAGCCG-3' (SEQ ID NO: 42); Rh178 5'-CGTTTGCTTCCTATGTC-CGC-3' (SEQ ID NO: 43) and 5'-CATTTGCATGCAGCT-GTGCG-3' (SEQ ID NO: 44).

Immunological Analysis of Rhesus Macaques.

Collection of BAL was performed as described previously (C. J. Pitcher et al., *J Immunol* 168, 29 (2002)). CD4+ and CD8+ T cell responses were measured by flow cytometric intracellular cytokine analysis of PBMC and BAL cells, as previously described (S. G. Hansen et al., *Nat Med* 15, 293 (2009)). For T cell stimulation assays RhCMV lysates (68-1 strain) or overlapping 15mer peptides representing the SIV-mac239 Gag, Rev/Tat/Nef proteins or the RhCMV Immediate Early-1 and 2 proteins (overlap=11 amino acids), were used in the presence of co-stimulatory mAbs CD28 and CD49d (BD Biosciences). Co-stimulation in the absence of antigen served as a background control. Cells were incubated with antigen and the costimulatory molecules alone for 1 hr, and then in the presence of the secretion inhibitor Brefeldin A (10 µm/ml; Sigma Aldrich) for an additional 8 hrs. After surface and intracellular staining with conjugated mAbs, polychromatic (6 to 8 parameter) flow cytometric analysis was performed on an LSR II Becton Dickinson instrument. List mode multi-parameter data files were analyzed using the FlowJO software program (version 8.8.6; Tree Star, Inc.). Using this software CD3+ cells were divided into CD4+ and CD8+ T cells subsets, and then analyzed for a subset manifesting up-regulation of the activation marker CD69 and cytokine, either TNFα alone (FIG. 1 data), or TNFα and/or IFN-γ (FIGS. 2-4 data) (see FIG. 6). For PBMCs, this background-subtracted value was divided by the fraction of total memory cells (determined as described below) to achieve the reported "memory corrected" response frequency (C. J. Pitcher et al., *J Immunol* 168, 29 (2002)). For BAL, the reported responses were background response (no antigen) subtracted only, as BAL T cells are entirely memory cells. (C. J. Pitcher et al., *J Immunol* 168, 29 (2002)). To determine the memory fraction of circulating T cells, memory and naive T cell subset populations were delineated based on CD28 and CD95 expression patterns, as described in (C. J. Pitcher et al., *J Immunol* 168, 29 (2002)) (see FIG. 7).

Example 2

In this Example, Applicants develop a number of attenuated RhCMV-vaccines to examine the highest level of attenuation that may still achieve protection against ΔUS2-11-Gag. A limitation of Applicants' preliminary data was that Applicants had only shown that natural infection with RhCMV was protective against re-infection with ΔUS2-11, but Applicants had yet to demonstrate that experimental infection with recombinant RhCMV would be protective. Applicants now demonstrate that a recombinant virus lacking the major tegument proteins pp65a and pp65b or pp71 protects against re-infection by ΔUS2-11-Gag.

PP65 is one of the most abundant proteins in HCMV particles and the most abundant component of the viral tegument, an amorphous protein structure layered between the capsid and the envelope. In addition to its role in evading innate immune responses, pp65 is one of the most immunogenic proteins encoded by HCMV and it is therefore included in most experimental vaccines and pp65-specific T cells are routinely included in adoptive transfer protocols. However, the role of pp65 for acute and persistent infection in vivo has never been examined.

Figure 10:
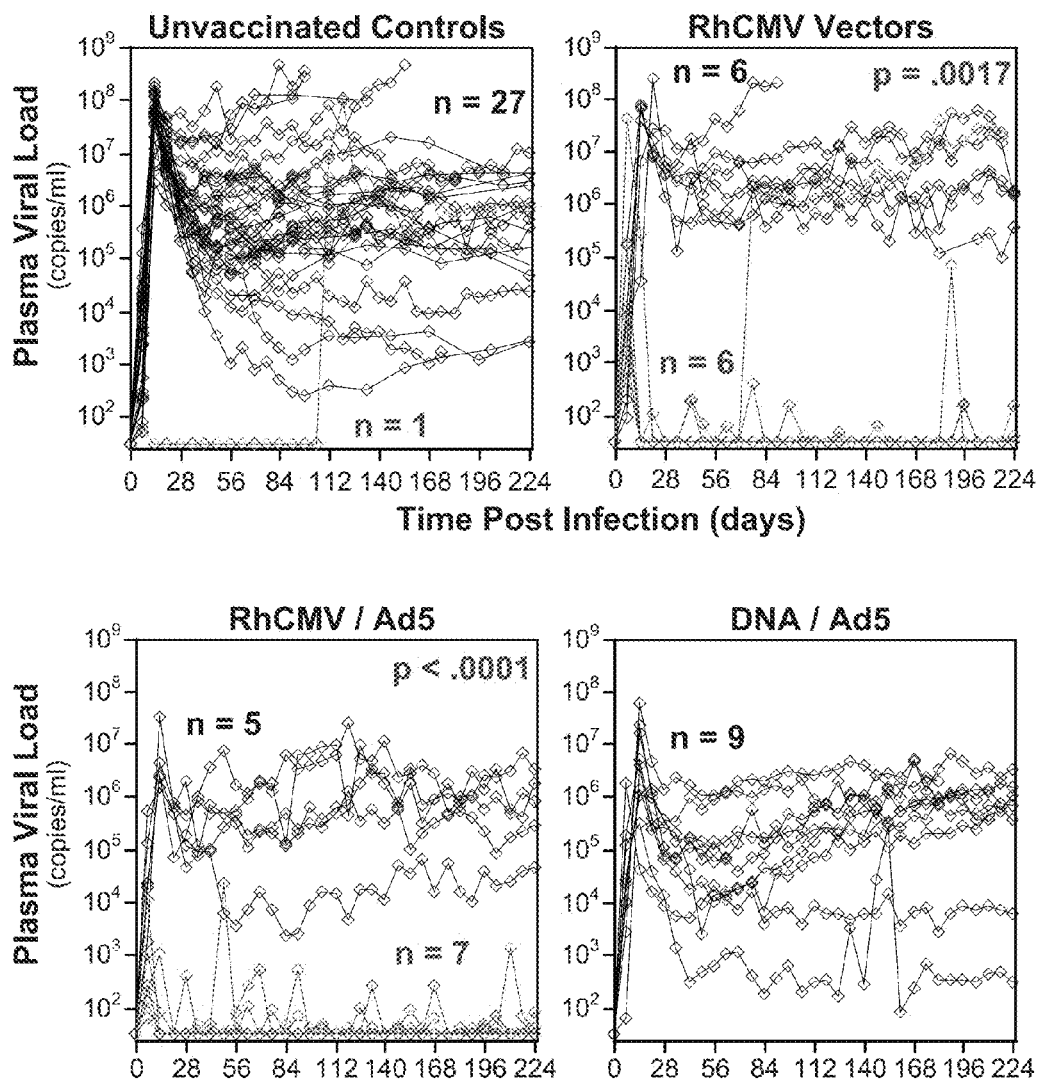
FIG. 10. Outcome of repeated, limiting dose, intra-rectal SIVmac239 challenge of RM vaccinated with A) RhCMV vectors alone (encoding gag, retanef, pol and env; given at wks 0, 14); Group B) the same RhCMV/SIV vectors (wk 0) followed by pan-proteome Ad5 vectors (wk 14); Group C) pan-proteome DNA (wks, 0, 4, 8), followed by pan-proteome Ad5 vectors (wk 14); and Group D) unvaccinated controls (with challenge initiated at wk 59). These RM were challenged weekly until the first above-threshold plasma viral load (>30 copies/ml) with infection considered to have been initiated by the challenge the prior week. The p values refer to difference in the fraction of "protected" (red) vs. progressively infected (black) RM in the CMV alone and CMV/Ad5 groups vs. the unvaccinated controls.). Of the 24 RM that received an RhCMV/SIV (gag/env/rev/nef/tat/pol) vector-containing regimen (Groups A and B), 13 (54%) manifested initial SIVmac239 infection with a variably-sized burst of plasma viremia followed by immediate control to below detection. Although protected RM manifested low level viral blips about once every 10 weeks (which gradually waned to none), overall viral control was sufficiently early and stringent to preclude any CD4+ target cell depletion, as well as to prevent induction (Group A) or boosting (Group B) of the anti-SIVenv antibody response.
Figure 11:
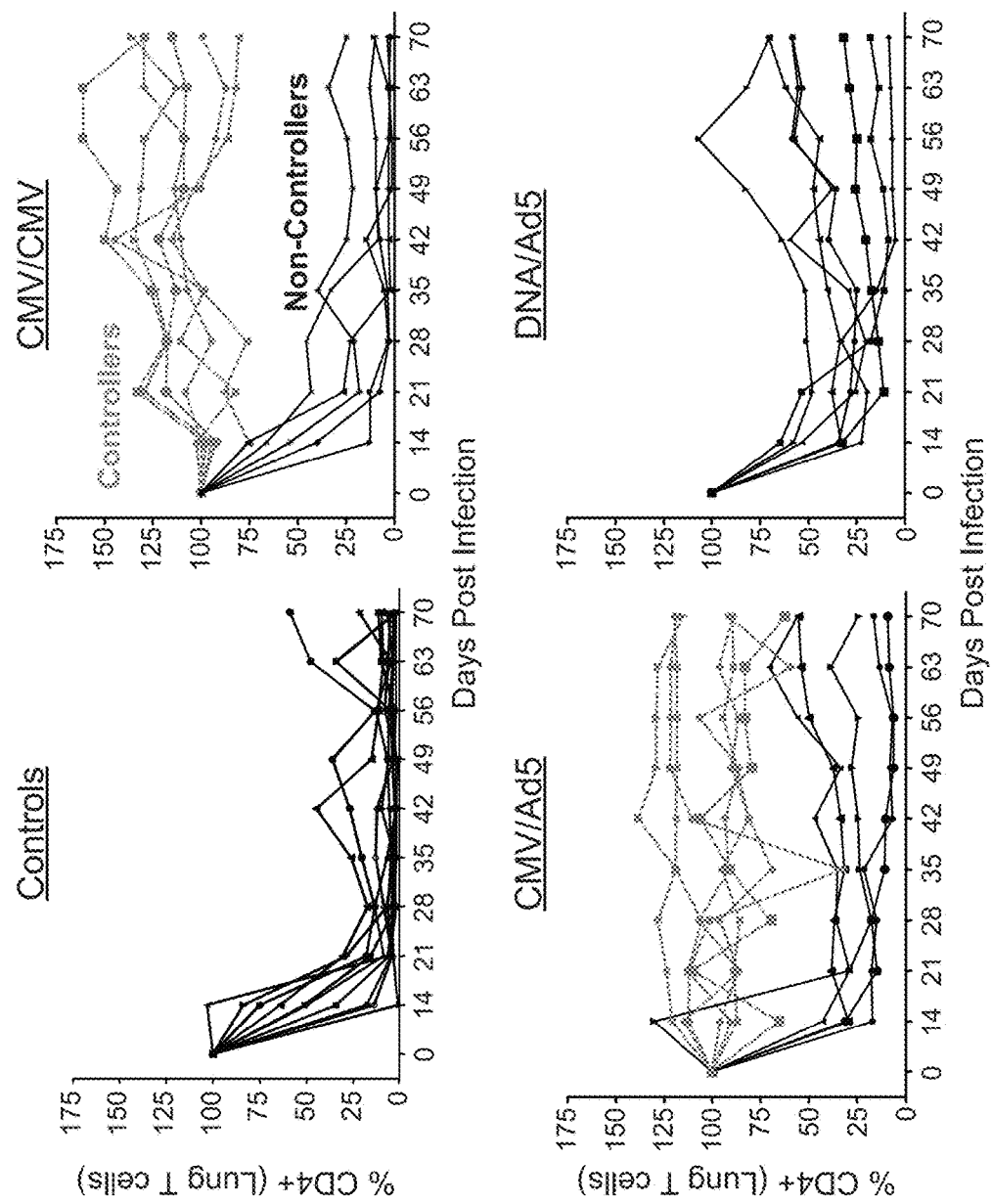
FIG. 11. No effector site CD4+ T cell depletion in protected RhCMV vector-vaccinated RM ("Controllers"). Analysis of the extent and kinetics of CD4+ memory T cell depletion in BAL following infection of controllers (grey) vs. non-controllers (black) within Groups A-D, with the significance of differences in average depletion from days 21-70 pi of Group A and B controllers vs. Group C determined by the Wilcoxon rank sum test.

RhCMV encodes two homologues of HCMV pp65 (UL83), pp65a (Rh111) and pp65b (Rh112). Using BAC-mutagenesis, Applicants deleted Rh111 and Rh112 from the RhCMV genome. ΔRh111-2 does not show a growth defect in fibroblast cultures (data not shown). Applicants infected two sero-negative animals with 5×106 pfu of ΔRh111-2. Infection was monitored immunologically over the following months (FIG. 10). Both animals developed a robust CMV-specific CD4+ T cell response as measured by intracellular cytokine staining. In contrast to animals infected with WT-RhCMV (a representative animal is shown in FIG. 10), neither of the ΔRh111-2-infected animals developed an immune response to pp65. To examine whether the anti-CMV immune response of two ΔRh111-2-infected animals was comparable to natural infection with respect to protection against ΔUS2-11-deleted virus, Applicants inoculated 107 pfu of ΔUS2-11-Gag s.c. and monitored the Gag-specific immune response. However, neither of the animals developed a CD4+ or CD8+ T cell response to Gag in PBMC whereas they remained positive for IE (FIG. 11, shown are the average responses).

Surprisingly, pp65 does not seem to be required for primary infection of CMV-naïve animals by RhCMV. These data further demonstrate that experimental infection with recombinant RhCMV may protect against re-infection with ΔUS2-11. Interestingly, ΔUS2-11-protective T cell immunity does not seem to depend on pp65-specific T cells despite its immunodominance during natural infection in both human and rhesus CMV.

Figure 16:
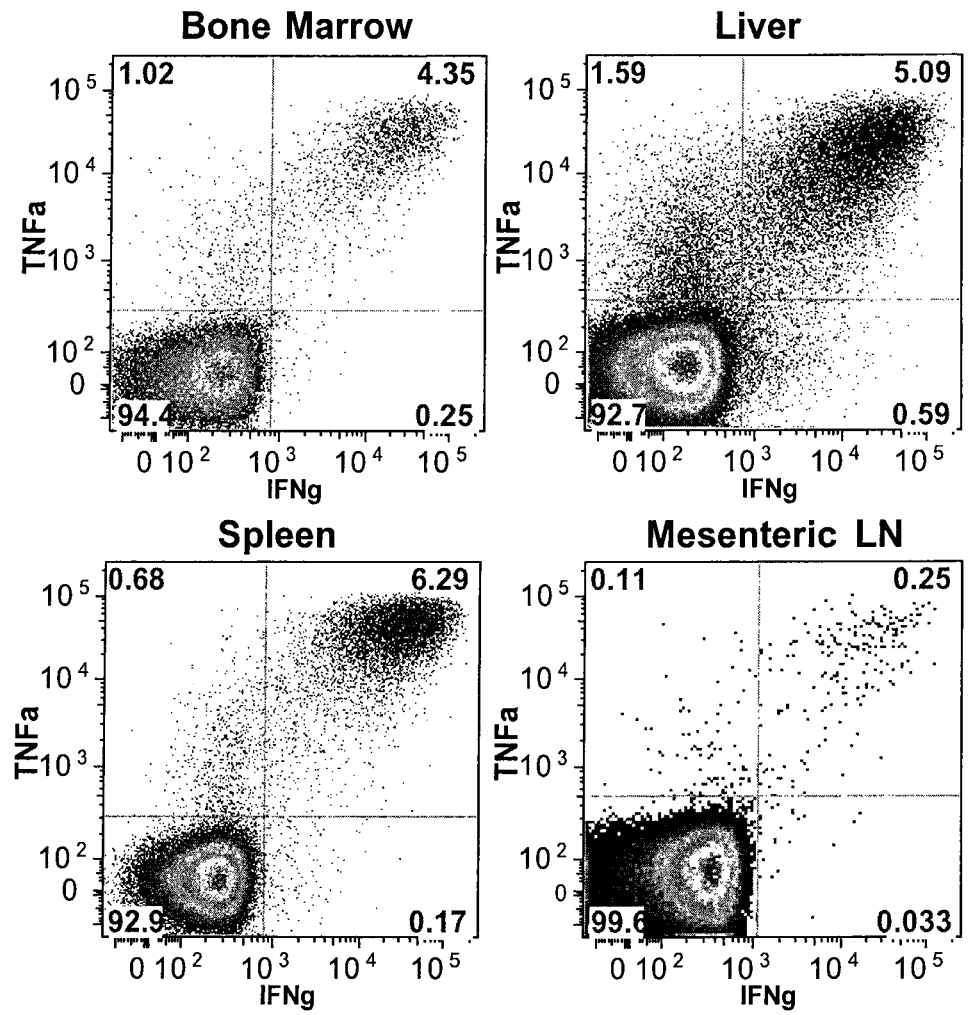
FIG. 16. The "CMV/SIV Vector Shield": CMV vectors elicit and maintain high frequency SIV-specific T cells in effector sites—sites that contain high SIV target cell densities and comprise the likely sites of early SIV amplification after mucosal inoculation. [quadrant %s shown; background was negligible for all assays.] Data are shown from the necropsy of one animal seven years after inoculation with RhCMV(gagL).

RhCMV/SIV vectors may 1) establish persistent infection in RhCMV-seropositive rhesus macaques (RM), 2) elicit potent, long-lasting SIV-specific CD4+ and CD8+ T cell responses with a strong "effector memory" (TEM) bias (see FIG. 16), and 3) protect ~50% of vaccinated RM from progressive SIV infection after limiting dose, intra-rectal challenge with the highly pathogenic SIVmac239 virus (see FIG. 10). The protection manifested in RhCMV/SIV vaccinated RM is distinct from previous T cell SIV vaccines in its abruptness and extent, with protected RM manifesting a viral burst in plasma of varying size upon initial infection, followed by immediate control to undetectable levels. While these RM may subsequently show periodic, low level "blips" of viremia, CD4+ memory depletion is not observed and SIV-specific antibody (Ab) responses do not boost, indicating a very high level of control. Moreover, to date, this stringent control has been stable for >30 weeks in 16/17 protected RM. Protection correlates with peak total SIV-specific CD8+ T cell responses in blood during the vaccine phase, which likely reflects the degree to which these cells are seeded into effector tissues. Taken together, these data indicate a novel pattern of protection consistent with very early control, likely occurring at the site of viral entry or early sites of viral replication and amplification, and mediated by tissue-resident CD8+ TEM. Significantly, the epitope targeting of RhCMV-vectored SIV-specific CD8+ T cell responses is distinct from responses elicited by conventional viral vectors or SIV itself: RhCMV-vectored CD8+ T cells target a broad array of (likely cross-presented) epitopes that exclude the typical immunodominant epitopes (e.g., CM9 or TL8 in Mamu A*01+RM) that are internally processed in and presented by virally infected cells (see FIG. 20). This differential CD8+ T cell targeting of wildtype (wt) RhCMV vectors is mediated by the activity of RhCMV genes that inhibit class I MHC-restricted Ag presentation (US2-11 homologues), as US2-11 deletant RhCMV vectors elicit CD8+ T cell responses that include prominent responses to the conventional SIV epitopes (see FIGS. 17, 19 and 20). In this Example, Applicants define the immunobiology of RhCMV/SIV vector-mediated protection, including the mechanisms, timing and location of protection, and the impact of differential CD8+T epitope targeting on the efficiency of SIV control, in particular asking whether broadening RhCMV/SIV-vectored CD8+ T cell responses to include typical dominant epitopes may improve response quality and enhance efficacy. The goals of this Example are:

The differential epitope targeting patterns and breadth of SIV-specific CD8+ T cells elicited by wt vs. (MHC I-down-regulation-null) US2-11-deletant RhCMV/SIV vectors is hypothesized to correlate with their breadth and efficacy; US2-11 deletant vectors direct vector-elicited CD8+ T cell responses to include typical internally processed epitopes (see FIGS. 19 and 20). Such vectors might therefore have enhanced efficacy against limiting dose intra-rectal SIV-mac239 challenge compared to wt vectors. By homology, US2-11 deleted HCMV-vectors carrying HIV antigens are expected to induce a broader T cell response to HIV epitopes which might correlate with better protection HIV infections of humans and SIV infections of Asian macaques share a pattern of viral replication and a constellation of pathologic features that in the absence of effective anti-retroviral therapy results in unremitting infection, and progressive, ultimately fatal, immunodeficiency in the vast majority of infected individuals (Levy, J. A. 1993. Microbiol Rev 57:183-289. Grovit-Ferbas, K. et al. 1999. Human Immunodeficiency Virus. In Persistent Viral Infections. R. Ahmed, and A. I. Chen, editors. Chicester: John Wiley & Sons. 3-45, Douek, D. C. et al. 2003. Annu Rev Immunol 21:265-304, Grossman, Z. et al. 2006. Nat Med 12:289-295, McChesney, M. et al. 1999. Simian Immunodeficiency Virus. In Persistent Viral Infections. R. Ahmed, and I. S. Chen, editors. Chichester: John Wiley & Sons. 321-345 and Cohen, O. J., and Fauci, A. S. 2001. Pathogenesis and Medical Aspects of HIV-1 Infection. In Fields Virology. D. M. Knipe, and P. M. Howley, editors. Philadelphia: Lippincott Williams & Wilkins. 2043-2094). A striking feature of these infections is their induction of robust cellular and humoral immunity, which fails to clear or, in most subjects, even effectively control viral replication. HIV/SIV adaptations that provide for efficient immune evasion include 1) massive replication, high mutation rates, genetic malleability and functional plasticity leading to rapid evolution, 2) specific genetic mechanisms to thwart innate and adaptive immune mechanisms (e.g., countering tetherin, APOBEC, Trim5α innate anti-viral mechanisms and cytotoxic T cells by class 1 MHC down-regulation), 3) env adaptations to avoid antibody (Ab) neutralization, 4) latency, and 5) dysregulated immune function (Evans, D. T., and Desrosiers, R. C. 2001. Immunol Rev 183:141-158, Johnson, W. E., and Desrosiers, R. C. 2002. Annu Rev Med 53:499-518, Goulder, P. J., and Watkins, D. I. 2008. Nat Rev Immunol 8:619-630, Malim, M. H., and Emerman, M. 2008. Cell Host Microbe 3:388-398 and Frost, S. D. et al. 2008. Curr Opin HIV AIDS 3:45-51). These mechanisms pose an imposing set of challenges for developing an effective HIV/AIDS vaccine, but fortunately, it is increasingly clear that HIV/SIV do have immune vulnerabilities. CD8+ T cell responses, and to a lesser extent, Ab responses may modulate viral replication, and in certain circumstances may manifest sufficient anti-viral activity to control, albeit not eliminate, infection (Goulder, P. J., and Watkins, D. I. 2008. Nat Rev Immunol 8:619-630, Frost, S. D. et al. 2008. Curr Opin HIV AIDS 3:45-51, Baker, B. M. et al. 2009. Expert Opin Biol Ther 9:55-69 and Goonetilleke, N. et al. 2009. J Exp Med 206:1253-1272). In HIV/SIV infections of naïve subjects, most adaptive immune responses develop only after substantial systemic viral replication has already occurred, and therefore, for these responses to manifest virologic control, they must be of superlative potency and/or have optimal epitope targeting to prevent viral evolution and escape. However, there is increasing evidence that the initial viral bridgehead in the first few days after mucosal exposure, made by one or two viral species (Keele, B. F. et al. 2008. Proc Natl Acad Sci USA 105:7552-7557), is much more vulnerable. At this stage, immunity would act on a much smaller, less diverse and localized viral population, and if such responses could suppress the viral reproductive ratio (R0) to <1, the infection may fail to establish altogether (Haase, A. T. 2005. Nat Rev Immunol 5:783-792). Indeed, increasing evidence suggests that immunity has the potential to prevent and/or stringently control HIV/SIV infection, but the window of opportunity for this high level protection is almost certainly both early and short.

Figure 12:
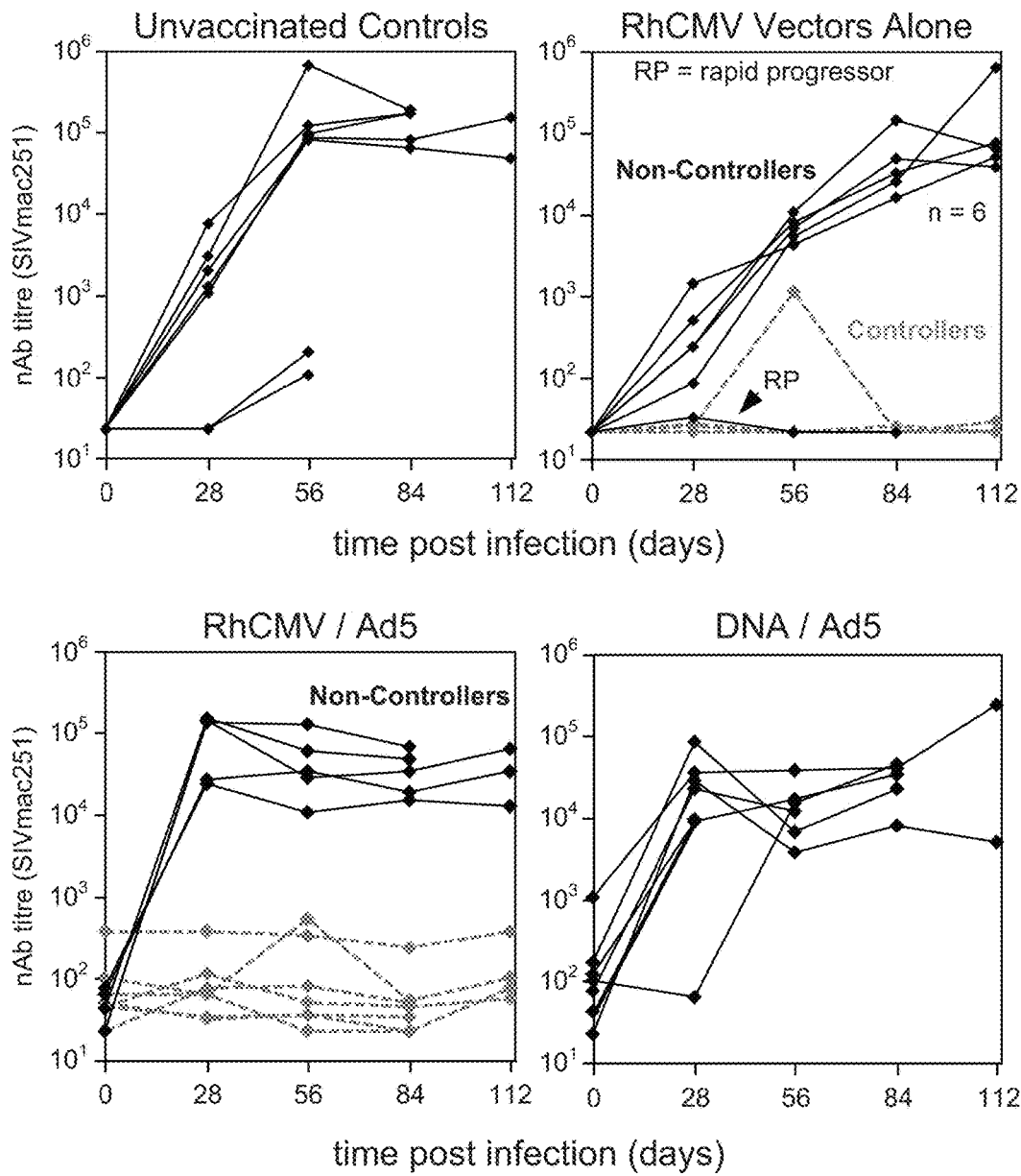
FIG. 12. Neutralizing Ab titres against lab-adapted SIVmac251 are induced or boosted with the onset of systemic infection in unvaccinated control RM, DNA/AD5-vaccinated RM and non-controllers in the RhCMV vector-vaccinated groups; however, controllers (grey) in the latter groups show little to no such induction or boosting, consistent with limited Ag exposure and thus, stringent virologic control. [RP=rapid progressor]

The association of elite HIV/SIV control in humans and non-human primates (NHP) with CD8+ T cell responses targeting particular epitopes restricted by specific class I MHC alleles led to the hypothesis that a vaccine capable of eliciting strong and broadly targeted virus-specific CD8+ T cell memory might, upon infection, bring to bear sufficient immunologic pressure on vulnerable viral sequences to suppress viral replication and/or force genetic changes resulting in reduced viral fitness (Walker, B. D., and Burton, D. R. 2008. Science 320:760-764 and Watkins, D. I. et al. 2008. Nat Med 14:617-621). While not expected to prevent infection, it was hypothesized that such a vaccine-elicited T cell response would reduce median peak and plateau-phase viral loads in the population, and thereby, on average, slow pathogenesis, and reduce the likelihood of transmission. In the past few years, this concept has been extensively evaluated in the Indian-origin RM/SIVmac model using increasingly potent vectors and prime-boost combinations, and a variety of challenge routes and doses. The general conclusions from these studies are that, compared to naïve RM, the best vaccine regimens may indeed reduce peak and plateau-phase viral loads of highly pathogenic SIVmac viruses and extend survival. However, protection is 1) uneven within identically vaccinated RM cohorts (and often correlated with protective MHC alleles), 2) seemingly limited to ~1.5-2 log mean reduction in peak and plateau phase plasma viral loads with SIVmac challenge, and 3) subject to reversion over time (18-29). This pattern of protection is similar for intravenous, high (single) and low (repeated) dose mucosal challenge, and appears to derive from a massive anamnestic CD8+ T cell response after infection that "intercepts" viral replication fairly late during systemic spread, with anti-viral activity first manifested by a blunting of peak SIV replication at day 10 to 14. As illustrated in FIG. 12, the CD8+ memory T cells that result from prime-boost vaccines with non-replicating vectors are dramatically expandable upon infection, but the proliferation, differentiation and effector cell delivery to viral replication sites is quite delayed relative to viral kinetics, a temporal relationship that clearly limits both the extent and durability of protection. Indeed, the first test of this concept in humans, the phase 2b Merck STEP trial (HVTN 502), was a clear failure. Despite detection of HIV-specific CD8+ T cells in 73% of vaccinees, there was no evidence of protection in terms of infection acquisition or post-infection viral replication (Buchbinder, S. P. et al. 2008. Lancet 372:1881-1893, McElrath, M. J. et al. 2008. Lancet 372:1894-1905). The STEP regimen may, in retrospect, have been insufficiently potent (or unable to elicit a sufficiently broad HIV-specific CD8+ T cell response) to achieve significant protection, but the results clearly illustrate the difficulty in attaining meaningful efficacy with a vaccine designed to elicit conventional CD8+ memory T cells.

If conventional vaccine-elicited T cell memory (memory responses that, upon initial pathogen encounter, require effector expansion, differentiation and migration to mediate anti-viral activity) intervenes too late in HIV/SIV infection, the alternative is a vaccine designed to elicit and maintain "effector memory" T cells (TEM). TEM lack robust expansion capacity, but are localized in effector sites and poised for immediate effector function (Bannard, O. et al. 2009. Eur J Immunol 39:2083-2087, Hansen, S. G. et al. 2009. Nat Med 15:293-299, Sallusto, F. et al. 2004. Annu Rev Immunol 22:745-763, Picker, L. J. et al. 2006. J Clin Invest 116:1514-1524, Pitcher, C. J. et al. 2002. J Immunol 168: 29-43 and Genesca, M. et al. 2009. J Intern Med 265:67-77). Indeed, CD4+ TEM are the primary targets of HIV/SIV (Grossman, Z. et al. 2006. Nat Med 12:289-295), and as CD4+ and CD8+ TEM cohabit the same sites, a vaccine-generated CD8+ TEM response would theoretically be ideally positioned to intercept initial/early viral replication in primary infection, providing anti-viral effector activity during the most vulnerable phase of infection. Long-term maintenance of TEM populations is associated with persistent Ag, and conversely, a pronounced TEM bias characterizes T cell responses to chronic/persistent agents, in particular CMV (Hansen, S. G. et al. 2009. Nat Med 15:293-299, 35, 38-40). Applicants therefore initiated a RhCMV vector development program to assess the ability of TEM to intervene early in primary SIV infection. As recently described (Hansen, S. G. et al. 2009. Nat Med 15:293-299, Picker, L. J., Reed-Inderbitzin, E. F., Hagen, S. I., Edgar, J. B., Hansen, S. G., Legasse, A., Planer, S. et al. 2006. J Clin Invest 116:1514-1524, Gauduin, M. C. et al. 2006. J Exp Med 203:2661-2672, Kern, F. et al. 1999. Eur J Immunol 29:2908-2915, Champagne, P. et al. 2001. Nature 410:106-111), RhCMV may be modified to highly express SIV proteins, without disruption of other RhCMV genes, and with preservation of wildtype growth characteristics (in vitro and in vivo). These vectors may re-infect RhCMV-seropositive RM in a clinically silent manner, and in the process of re-infection elicit indefinitely persistent, high frequency CD4+ and CD8+ T cell responses against the SIV gene products. These RhCMV-vector elicited SIV-specific T cell responses manifest a polyfunctional, highly TEM-biased phenotype, and in keeping with this phenotype were highly enriched in effector sites [(Hansen, S. G. et al. 2009. Nat Med 15:293-299); and see FIG. 16]. RhCMV/SIV vectors do not elicit significant SIV-specific Ab responses, nor do they appear even to prime for such responses (Hansen, S. G. et al. 2009. Nat Med 15:293-299). In the first efficacy assessment of these vectors, RM immunized with RhCMV/gag, /rev/nef/tat, and/env were challenged with repeated, limiting dose intra-rectal SIVmac239 at 486-615 days after the last vaccination. This challenge protocol was designed to infect RM via mucosal exposure with viral doses more akin to sexual HIV transmission in humans (24). Applicants found that 4/12 vaccines (vs. 0/16 controls) were demonstrably infected with SIV but completely controlled infection, to the extent that CD8+ cell depletion failed to elicit viral recrudescence (Hansen, S. G. et al. 2009. Nat Med 15:293-299). As described in detail below, these initial results have been confirmed and extended in a second large RM efficacy using the same repeated, limiting dose SIVmac239 challenge. Overall, ~50% of RhCMV/SIV-vaccinated RM have been highly protected from progressive SIV infection after intra-rectal challenge with highly pathogenic, CCR5-tropic SIV.

Figure 13:
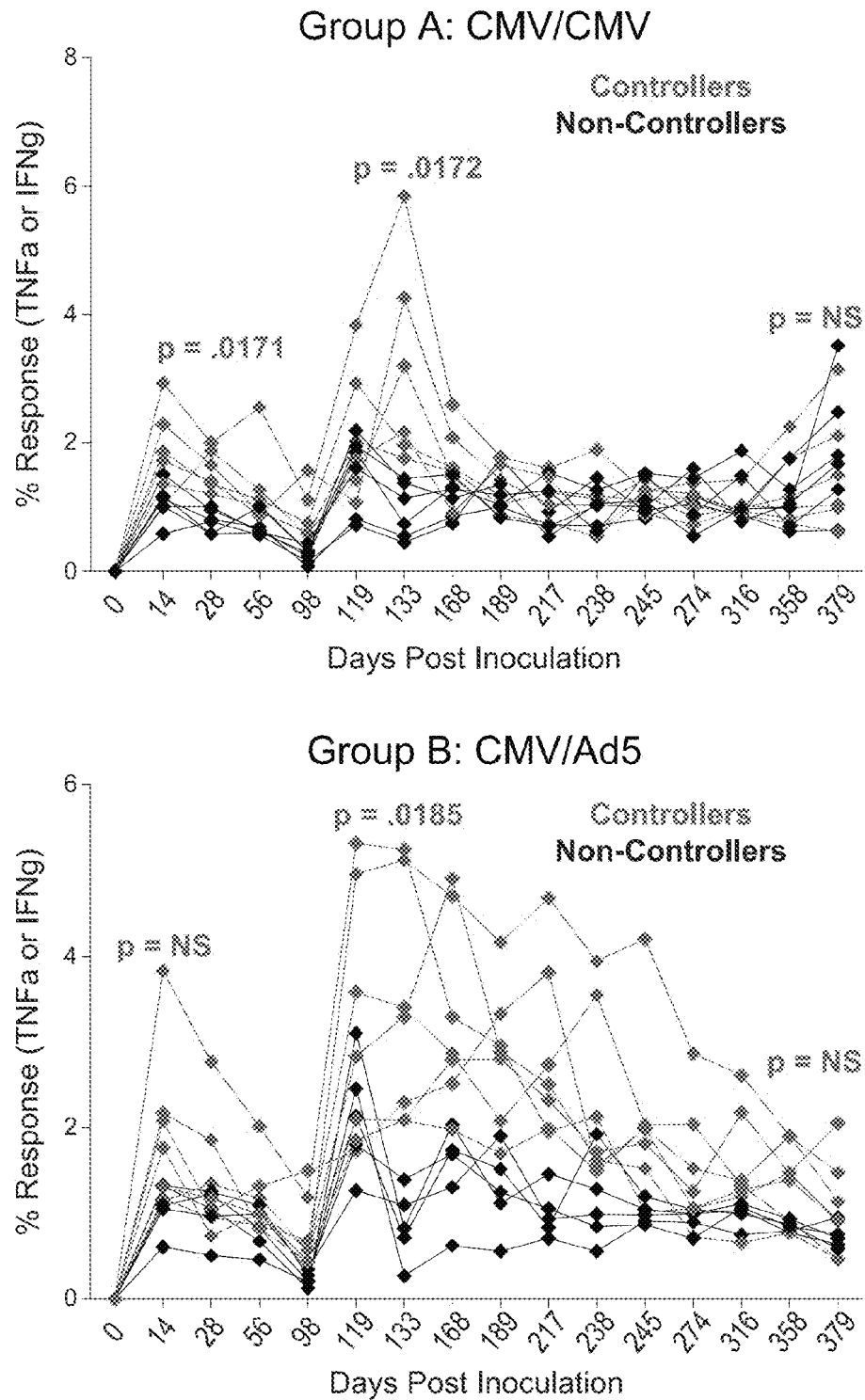
FIG. 13. Total SIV (gag, env, rev/nef/tat, and pol)—specific CD8+ memory T cell responses in blood during the vaccine phase of Groups A and B with subsequent controllers shown in red and noncontrollers in black. Note that in both groups the peak response postboost, but not the response at challenge, correlated with outcome.
Figure 14A:
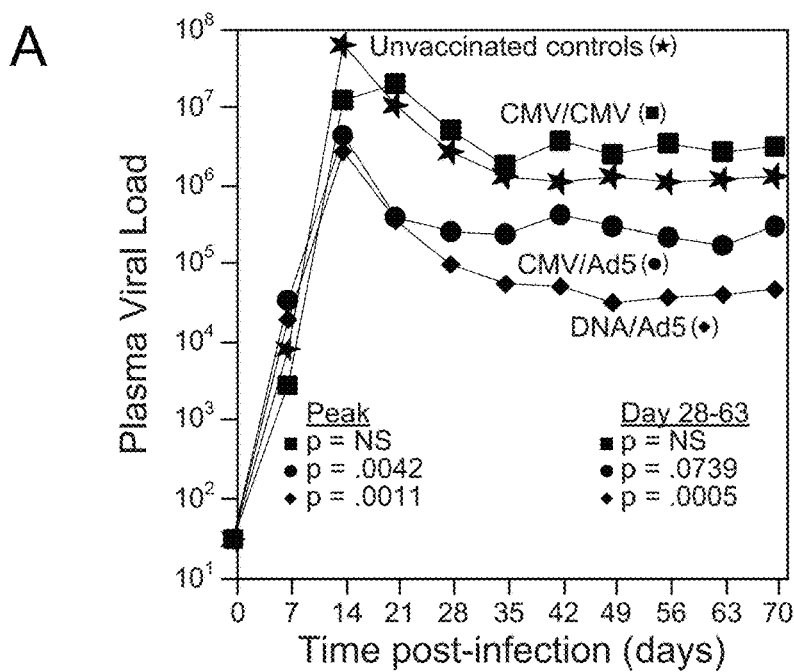
FIGS. 14A-14B. Peak and post-peak control and boosting responses in study RM with progressive infection (protected RM in the CMV/CMV and CMV/Ad5 groups are not included in this figure). Note that peak and post-peak viral suppression correlates with the ability to manifest an anamnestic CD8+ T cell response boost to infection. Quantitative real-time RT-PCR and PCR assays targeting a highly conserved sequence in Gag were used for standard measurements of plasma SIV RNA and cell-associated SIV RNA and DNA within peripheral blood and lymph node mononuclear cells, as previously described (Cline, A. N. et al. J Med Primatol 34, 303-312, (2005); Venneti, S. et al. Am J Pathol 172, 1603-1616, (2008)).
Figure 14B:
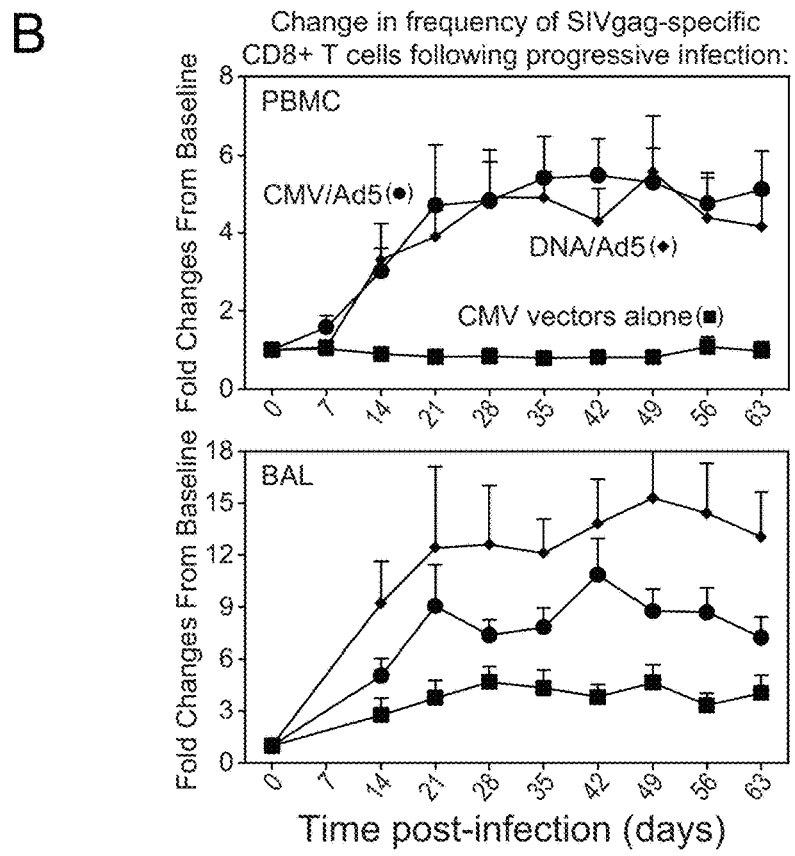

Worldwide in 2007, there were ~2.5 million new HIV infections, over 33 million people living with HIV and 2.1 million AIDS deaths (2008 UNAIDS Report). In southern Africa, adult prevalence rates may exceed 15%. An effective prophylactic vaccine would have a tremendous impact on the epidemic, and is likely the only way it may be conquered. As discussed above, HIV is an extremely difficult vaccine target, and an effective HIV/AIDS vaccine most likely has to include multiple components, each designed to exploit different viral immune vulnerabilities and acting at different stages of primary infection (FIG. 13). CMV vectors (and the "TEM" vaccine concept) offer a powerful new addition to this vaccine "arsenal", and it thus becomes a high priority to both define the mechanism(s) by which these vectors protect and optimize their efficacy. This information is critical for the "translation" of CMV vectors into the clinic, as well as for developing other modalities that would utilize or enhance the same protective mechanism(s). It should also be emphasized that the early protection mediated by CMV vector-elicited responses offers both a new window to explore and a new means to experimentally manipulate early HIV/SIV-immune system interactions. Thus, the understanding of TEM biology and mechanisms by which CMV vector-elicited TEM protect sheds light on the crucial early events that follow mucosal HIV/SIV infection. This Example addresses these priorities by providing detailed analysis of 1) the distribution and functional characteristics of RhCMV vector-elicited, SIV-specific T cells and the relationship between these characteristics and efficacy, 2) where and how these responses "intercept" and suppress mucosally administered SIV in primary infection, and control SIV replication over the long-term, and 3) the differential CD8+ T cell epitope targeting mediated by US2-11 gene function in wt vs. mutant CMV/SIV vectors, and the impact of this differential targeting on efficacy.

Figure 17:
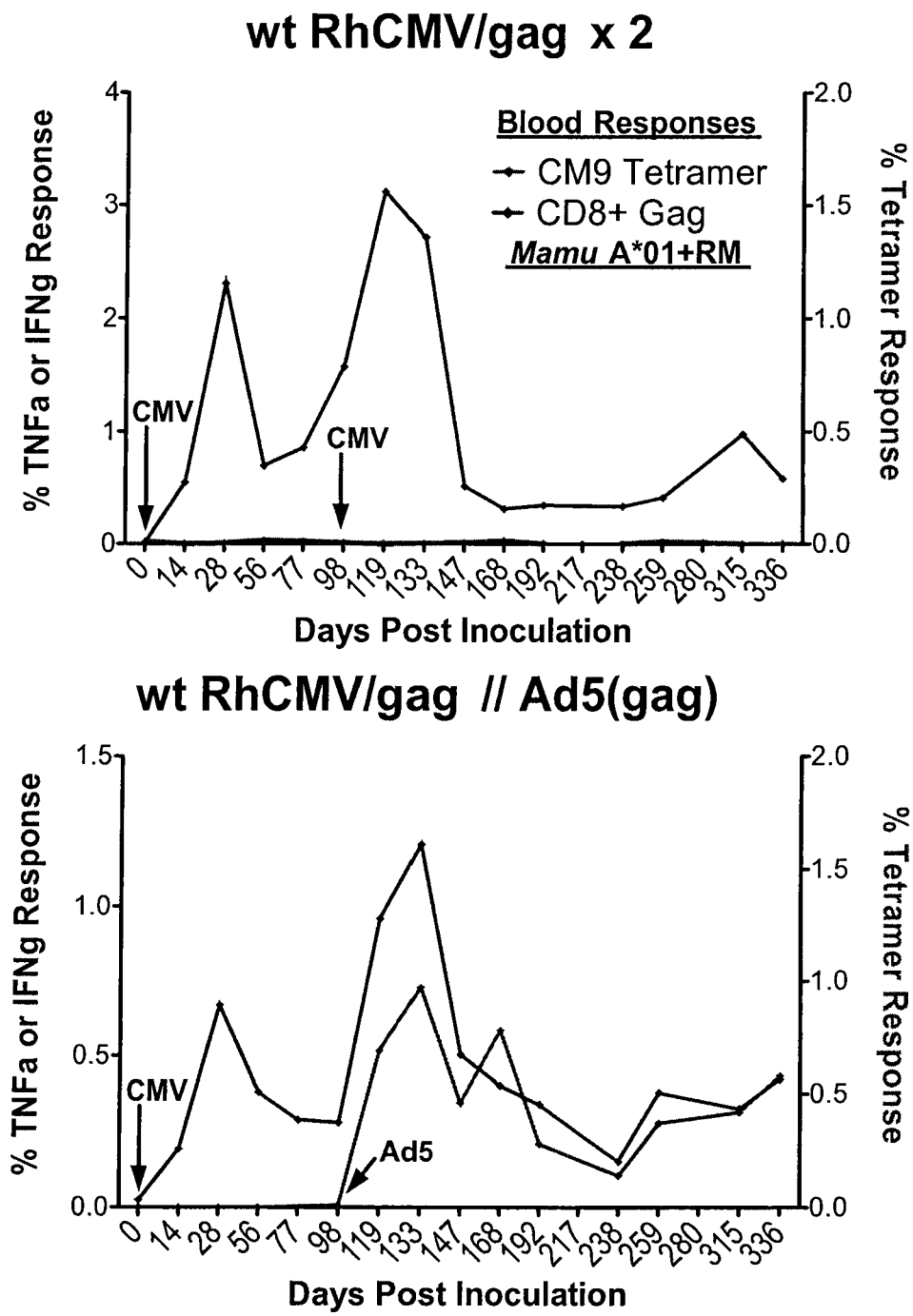
FIG. 17. RhCMV/SIV vector-elicited SIV-specific CD8+ T cell responses do not include the typical immunodominant responses that are targeted in SIV infection itself or after vaccination with DNA and/or conventional viral vectors. The figure shows peripheral blood CD8+ T cell responses to a total SIVgag 15mer peptide mix (blue) or to the Mamu A*01-restricted SIVgag CM9 epitope (red) in 2 representative Mamu A*01+RM, one that received RhCMV/gag twice (week 0, 14) and one that received RhCMV/gag at week 0 and Ad5/gag at week 14. Note that CM9 responses do not arise after RhCMV/gag vaccination, but do develop after subsequent Ad5/gag vaccination.

Applicants have accomplished all of the above goals, including construction, optimization, and selection of RhCMV vectors expressing SIVgag, rev/nef/tat, env and pol, extensive assessment of vector biology and immunogenicity, and most importantly, efficacy assessment and delineation of immune correlates. The hypothesis that RhCMV vectors and the TEM responses they elicit may be efficacious against highly pathogenic SIV has been confirmed, and a new pattern of early protection has been discovered. The details of these accomplishments are described in Hansen, et al. (Hansen, S. G. et al. 2009. Nat Med 15:293-299).

Applicants followed the promising results of Applicants' first efficacy assessment of RhCMV/SIV vectors (Hansen, S. G. et al. 2009. Nat Med 15:293-299) with a larger trial that included 4 arms: A) RhCMV/gag, RhCMV/env, RhCMV/rev/nef/tat, RhCMV/pol-1, and RhCMV pol-2 (wks 0, 14), B) the same RhCMV/SIV vectors (wk 0) followed by pan-proteome Ad5/SIV vectors (wk 14), C) pan-proteome DNA (wks, 0, 4, 8) followed by pan-proteome Ad5 vectors (wk 14), and D) additional unvaccinated controls. These RM were challenged with same repeated, limiting dose, intrarectal SIVmac239 regimen as Applicants' first study, with challenge initiated at wk 58. The results of this trial were unprecedented (FIG. 10). Of the 24 RM that received an RhCMV/SIV vector-containing regimen (Groups A and B), 13 (54%) manifested initial SIVmac239 infection with a variably sized blip/burst of plasma viremia, which was followed by immediate control to undetectable levels. None of 9 DNA/Ad5-vaccinated RM manifested such control, and only 1 of 28 unvaccinated RM manifested an initially occult infection (which spontaneously reverted to progressive infection at wk 16). Protected RhCMV/SIV-vaccinated RM manifested variable numbers of low level viral blips at subsequent time points (FIG. 10), but overall viral control was sufficiently early and stringent to preclude any CD4+ target cell depletion (FIG. 11), as well as prevent induction (Group A) or boosting (Group B) of the anti-SIVenv antibody response (FIG. 12). Importantly, protection in both RhCMV vector-vaccinated groups significantly correlated with the magnitude of the peak total SIV-specific CD8+ T cell response in blood during the vaccine phase (FIG. 13), not the responses present immediately pre-challenge (and not SIV-specific CD4+ T cell responses, not shown). These peak CD8+ responses in blood likely reflect the degree to which CD8+ TEM are seeded into systemic effector sites during vaccination. The RhCMV-vectored, SIV-specific T cell responses were fundamentally different from the responses elicited by DNA/Ad5. The latter did not provide the immediate protection seen in the RhCMV/SIV vector-vaccinated RM, but did demonstrate significant mean reductions in peak and early plateau-phase viral loads, and were associated with strong boosting upon infection (FIG. 14). In contrast, the protection associated with RhCMV/SIV vectors alone was binary, providing either immediate stringent control, or no control, and in keeping with this, these responses did not significantly boost in the unprotected (progressively infected) RM (FIG. 14). The RM given RhCMV/SIV and Ad5/SIV vectors showed both the immediate "TEM" protection, an element of peak and post-peak ("TCM") control, and a post-infection response boost, similar to, but less than, the DNA/Ad5-vaccinated group (FIG. 14). 12/13 of RhCMV vector-protected RM maintained stringent protection for >30 weeks, whereas 7/9 DNA/Ad5-vaccinated RM were indistinguishable from controls by 26 weeks post-infection.

Taken together, these results suggest that RhCMV-vectored SIV-specific T cell responses intercept mucosally administered SIV infection very early in primary infection, prior to extensive systemic replication and may maintain stringent control after this early "intercept". On the other hand, if the virus "wins" the initial battle and extensive, systemic replication ensues, RhCMV/SIV-vectored TEM responses are unable to "chase" and do not provide peak or post-peak protection. In Applicants' first study (Hansen, S. G. et al. 2009. Nat Med 15:293-299), Applicants found no evidence of persistent SIV infection in the 4 protected RM, and Applicants speculated that infection might have been aborted in the colonic mucosa itself. In the follow-up study, however, Applicants have documented higher initial viral bursts in plasma, and have found in most protected RM a very low-level persistent infection (manifest by occasional viral "blips"). Moreover, although cell-associated SIV is either very low or negative in PBMC of most samples from protected RM (data not shown), Applicants have unequivocally documented SIV DNA- and RNA-positive CD4+ T cells in the blood of protected RM (those with the highest initial viral bursts; FIG. 15), establishing that the SIV infection is not wholly contained in the rectal mucosa after rectal challenge, and protection must, at least in part, be systemic. These data strongly suggest that there is an early extra-mucosal phase of viral amplification and "broadcast", which is a likely (additional) point of intercept between RhCMV-vectored, SIV-specific TEM responses and the developing SIV infection. In keeping with this, Applicants have found that RhCMV/SIV vectors indefinitely maintain strikingly high frequencies of SIV-specific T cells in target cell-rich effector sites that are likely candidates for initial viral infection and amplification, including both rectal mucosa and sites of potential hematogenous viral spread—spleen, liver, bone marrow (FIG. 16). Smaller, but substantial frequencies of CMV-vectored, SIV-specific CD8+ T cells are in mesenteric lymph nodes (LN; FIG. 16), another site of potential viral spread. Applicants therefore hypothesize that this array of high frequency SIV-specific (CD8+) TEM responses constitutes a "shield" against early viral amplification, capable of arresting infection prior to progressive systemic infection.

During the course of evaluation of RhCMV/SIV vector immunogenicity, Applicants assessed the degree to which the CD8+ T cell responses elicited by these vectors recognized epitopes that had been previously shown to represent dominant targets in SIV-infected or DNA/Adenovirus/pox vector-vaccinated RM with the appropriate restricting MHC class I allele. These epitopes included Mamu A*01-restricted gag-CM9, -LW9, -VL8, -QI9, -VT10, -LF8, -LA9, env-TL9, and tat-SL8 (12 RM); Mamu A*02-restricted gag-GY9, env-RY8, and nef-YY9 (4 RM); Mamu B*08-restricted nef-RL10 (1 RM), and Mamu B*17-nef-IW9, -MW9, and env-FW9 (7 RM) (41-44). Surprisingly, whether analyzed by tetramer binding or intracellular cytokine staining (ICS), all these specific epitope responses were negative in RhCMV/SIV vaccinated RM, despite these RM manifesting robust CFC-defined, CD8+ T cell responses to total mixes of overlapping, consecutive 15mer peptides for the relevant SIV protein (FIG. 17). The failure to identify these typical immunodominant CD8+ T cell responses was neither technical, nor related to individual monkey peculiarities, as subsequent administration of Ad5/SIV vectors (or progressive SIV infection) in many of these RM was associated with the appearance for these typical responses (FIG. 17, right panel). These data indicate that RhCMV/SIV-vectored responses differ from DNA and conventional viral vectors (e.g., Ad5) not only in their TEM-biased phenotype, function, distribution and longevity, but also in their CD8+ T cell recognition patterns.

Figure 18:
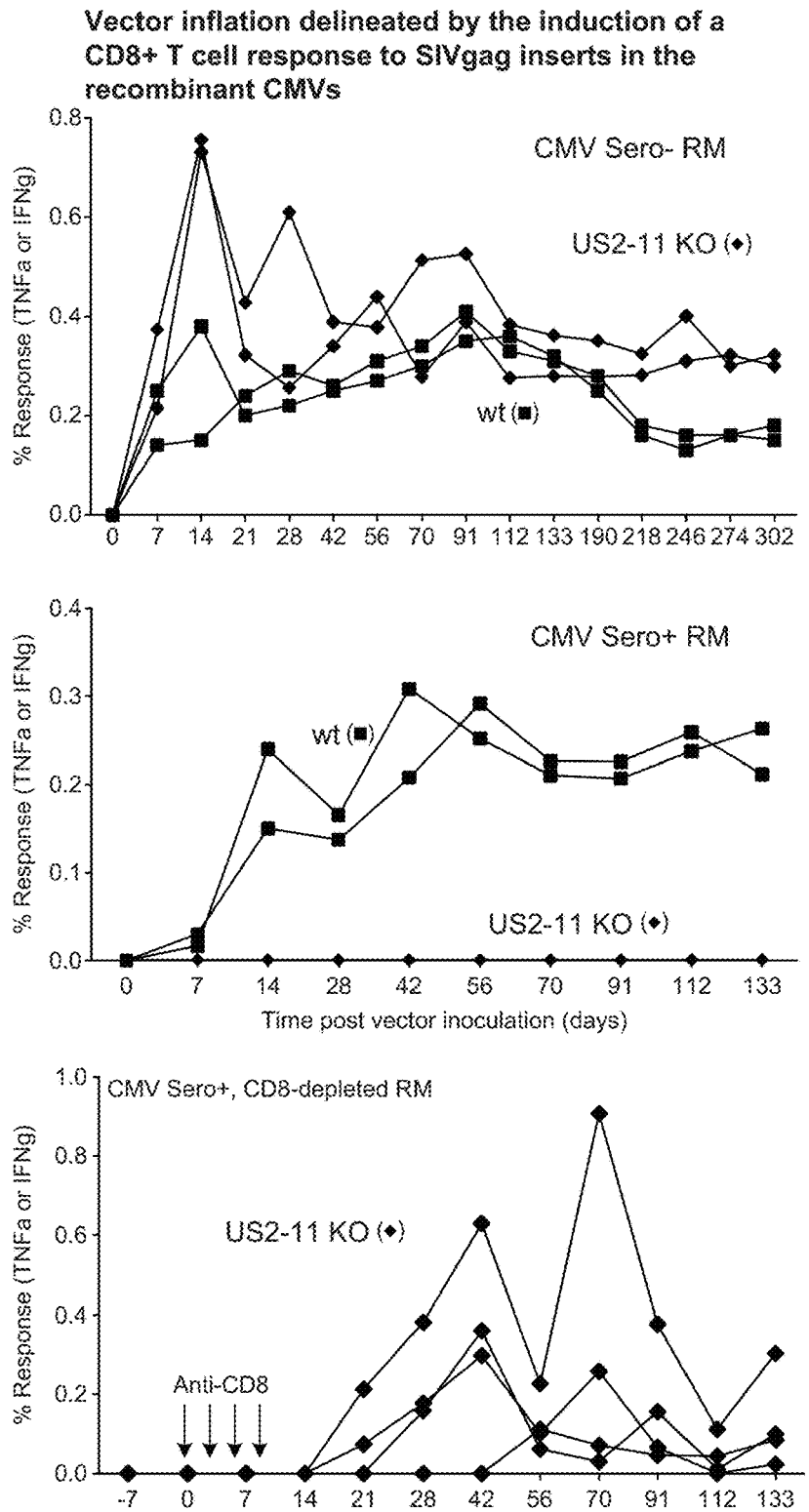
FIG. 18. Comparison of the ability of RhCMV(gag) (wt) vs. ΔUS2-11(gag) (US2-11 KO) vectors to infect RhCMV seronegative (CMV-naïve) RM (left panel), RhCMV seropositive RM (middle panel), and RhCMV seropositive RM that were depleted of CD8+ lymphocytes with mAb cM-T807 at the time of inoculation (right panel; 100% CD8+ T cell depletion in blood for 14 days). US2-11(gag) (US2-11 KO) RhCMV vectors may infect RhCMV-naïve RM, but not RhCMV+ RM, unless CD8+ T cells are depleted during the first 2 weeks. Infection or lack or infection was confirmed by isolation or failure of isolation, respectively, of the designated vector after co-culture of urine in all cases.

HCMV encodes 4 related glycoproteins that act together to prevent presentation of MHC class I-restricted epitopes by infected cells: US2 and US11 mediate the retrograde translocation of MHC-I molecules into the cytosol for proteosomal degradation; US3 retains MHC-1 molecules in the endoplasmic reticulum (ER); and US6 inhibits translocation of viral and host peptides across the ER membrane by the peptide transporter TAT (Powers, C. et al. 2008. Curr Top Microbiol Immunol 325:333-359. Liu, Z. et al. 2009. Int J Biochem Cell Biol 41:503-506, van der Wal, F. J. et al. 2002. Curr Top Microbiol Immunol 269:37-55 and Hewitt, E. W. et al. 2001. EMBO J 20:387-396). RhCMV encodes sequence and functional homologues of these 4 proteins in a genomic region spanning Rh182 (US2) to Rh189 (US11) (Powers, C., and Fruh, K. 2008. Microbiol Immunol 197: 109-115 and Pande, N. T. et al. 2005. J Virol 79:5786-5798). To assess the role of these proteins in RhCMV/SIV vector immunobiology Applicants constructed vectors in which the US2-11 region was specifically deleted (Powers, C. J., and Fruh, K. 2008. PLoS Pathog 4:e1000150). US2-11 knockout (KO) RhCMV vectors readily infected RhCMV-naïve RM (and manifest a virologically and immunologically "normal" primary infection), but were completely unable to re-infect RhCMV seropositive RM, unless CD8+ lymphocytes were depleted for at least 2 weeks during vaccination (FIG. 18). Interestingly, in both initially RhCMV-naïve RM and CD8-depleted, seropositive RM, the KO vector infection was indefinitely persistent, even after the appearance (naïve) or re-appearance (CD8-depleted) of RhCMV-specific CD8+ T cell responses. These data indicate a CD8+ cell-mediated checkpoint in re-infection that is bypassed by wt RhCMV via the function of these class I MHC Ag presentation inhibitory genes. While Applicants expected that loss of US2-11 gene product-mediated "protection" from cytolytic effector T cells would have a virologic consequence, it was surprising that this consequence only manifested in re-infection, suggesting that immune evasion by this mechanism may have evolved to allow superinfection, or possibly, to prevent pre-existent, cross-reactive CD8+ memory T cells (Sylwester, A. W. et al. 2005. J Exp Med 202:673-685) from interfering with primary infection. Even more surprising, however, was the effect of US2-11 deletion on CD8+ T cell response induction. In contrast to wt RhCMV/SIV vectors, the SIV-specific CD8+ T cell responses that developed during 1° infection with the US2-11 region KO vectors prominently targeted conventional Mamu A*01-restricted immunodominant SIV epitopes (FIG. 19). The gag-specific CD8+ T cell responses generated by wt RhCMV/gag were very broadly targeted, spanning all regions of the gag protein, but manifested a lack of reactivity with 15mer peptides containing the conventional immunodominant epitopes, creating distinct "holes" in the response breadth in Mamu A*01+RM (FIG. 20). In the gag-specific CD8+ T cell responses elicited by the US2-11 KO RhCMV/gag vector, these "holes" were filled, and the responses were even more broadly targeted. These observations have several important implications. First, they indicate that the lack of conventional immunodominant epitope recognition in RM vaccinated with wt RhCMV/SIV vectors is related to the prevention of class I MHC-restricted Ag presentation by infected cells, strongly suggesting that the CD8+ T cell responses generated by wt RhCMV/SIV vectors are not derived via Ag-presentation by infected cells, but rather by indirect presentation. Consistent with this, these results are reminiscent of Applicants' findings with gag protein adjuvanted with poly I:C or TLR 7/8 ligands, in which Applicants also observed the development of gag-specific CD8+ T cell responses that lack measureable responses to the Mamu A*01-restricted gag-CM9 epitope (unpublished observations). However, the RhCMV vector-elicited CD8+ T cell responses are much stronger and broader than the adjuvanted protein, suggesting a higher degree of cross-presentation efficiency, perhaps due to dendritic cell uptake/processing of apoptotic infected cells or CMV dense bodies (Pepperl, S. et al. 2000. J Virol 74:6132-6146). Moreover, the RhCMV vector cross-presentation mechanism is notable for its apparent complete exclusion of CD8+ T cell responses to multiple, conventional immunodominant epitopes, suggesting the very efficient inhibition of direct presentation and a distinct epitope processing mechanism for indirect presentation. The second implication of these data, which is more speculative, but potentially more significant, is the suggestion that cytotoxicity (direct killing of SIV-infected cells) may not play the primary role in the protection afforded by wt RhCMV/SIV vector-elicited CD8+ T cell responses. It is not that these cross-presentation-derived responses would lack intrinsic cytotoxic function [the cytotoxic apparatus of CD8+ TEM is present (Hansen, S. G. et al. 2009. Nat Med 15:293-299)], but rather that the epitopes targeted by these responses may not, as a group, be efficiently processed and presented by infected cells, and therefore might be poor targets for the direct recognition of SIV-infected cells that is required for cytotoxic T cells to mediate efficient killing [particularly in light of the ability of nef to also down-regulated MHC 1 molecules (Evans, D. T., and Desrosiers, R. C. 2001. Immunol Rev 183:141-158]. If this is true, it further follows that the robust protection mediated by wt RhCMV/SIV vector-elicited responses would most likely be due to a more indirect effector function (by T cells stimulated by APC in the neighborhood of infected cells), such as, for example, elaboration of CCR5 binding chemokines (Cocchi, F. et al. 1995. Science 270:1811-1815 and Arenzana-Seisdedos, F., and Parmentier, M. 2006. Semin Immunol 18:387-403). SIV-specific T cell responses elicited by the US2-11 KO RhCMV/SIV vectors clearly retain the broad epitope recognition that arises from cross-presentation, and maintain the same phenotypic and functional capabilities of wt vector-elicited responses (not shown), but in addition, include recognition of the epitopes that are efficiently processed by SIV-infected cells, and therefore, would include epitopes, like gag CM9 or tat SL8, that may mediate direct cytotoxicity (Loffredo, J. T. et al. 2007. J Virol 81:2624-2634). Thus, the responses elicited by US2-11 KO RhCMV/SIV vectors may have enhanced anti-viral function, either by more efficient cytotoxicity or direct viral suppression, or simply greater CD8+ T cell response breadth, or both. CD8+ responses elicited by US2-11 deletant vectors might therefore more efficiently protect RM from progressive SIV infection, increasing the fraction of protected RM above the current level, a important goal of Applicants' efforts to optimize TEM vaccine approaches.

Routine T cell response quantification is accomplished by cytokine flow cytometry (CFC; see FIG. 16) using mixes of overlapping 15 mer peptides for SIVgag, env, pol, and rev/nef/tat, and RhCMV IE, compared to control peptides (mTB Ag85b and ESAT6) and co-stimulation alone (Hansen, S. G. et al. 2009. Nat Med 15:293-299). During the vaccine phase of Group 1, 3 and 4 RM, Applicants routinely follow responses to these overlapping peptide mixes in PBMC and BAL using CFC tube #1. At necropsy, CFC tube #1 is used on fresh cell preparations from all individual tissue samples for all SIV proteins to comprehensively establish the systemic distribution of the SIV-specific T cell responses. CFC tube #s 2 and 3 retrospectively provide further functional characterization and phenotypic assessment (expression of CD25, HLA-DR, and PD-1) of the degree to which the Ag-specific T cells being measured were subject to activation in vivo. These additional "tubes" are applied in more limited fashion, focusing on one (cryopreserved) cell preparation from each tissue and on the dominant responses identified with the fresh tube #1 analysis. Cryopreserved splenic cells (which are not limiting) are analyzed with single peptide γ-IFN ELISPOT to "deconvolute" overall SIV protein-specific responses into individual 15 mer peptide responses, and then these single peptide responses are confirmed, lineage typed and functionally characterized with CFC tube #1 from the same cryopreserved splenic cell preps. Responses to the 5 highest frequency (CD8) epitopes are analyzed by CFC tube #1 (and selectively tube #s 2 and 3) in all tissues to define the distribution of these individual epitope responses. Proliferative potential to whole protein peptide mixes and to the 5 selected individual peptide responses per RM are determined in each tissue by 6 day CFSE dilution cultures of PBMC and selected tissue cell preps (Onlamoon, N. et al. 2007. J Med Primatol 36:206-2), and supernatants from these cultures are sampled after 48 hrs and analyzed for cytokine secretion patterns by Luminex analysis (IL-2, -4, -5, -13, -17, IFN-γ, GM-CSF, TNF, MCP-1, MIP-1α/β, RANTES) (Giavedoni, L. D. 2005. J Immunol Methods 301:89-101). Viral suppression assays on SIVmac239-infected autologous CD4+ T cells (Vojnov, L. et al. 2009. J Virol.) are performed on selected cell preparations to compare the anti-viral activity of responses in different tissues and arising from different vaccination routes. As demonstrated above, the CD8+ T cell responses elicited by wt RhCMV/SIV vectors do not include the typical immunodominant epitopes defined for SIV or other viral vectors, precluding the use of existing tetramers to analyze wt RhCMV/SIV vector-elicited responses. However, as part of this Example and other ongoing work, Applicants may identify and determine the restricting MHC allele on common, dominant CMV/SIV vector-elicited epitopes and have tetramers constructed for the most common of these epitopes. As they become available, these tetramers (as well as existing tetramers for "typical" epitopes in RM likely to have such responses—DNA/Ad5-vaccinated and/or SIV-infected), are applied to this Example in appropriate RM (e.g., correct MHC types), both to directly quantify and phenotypically characterize tetramer defined responses in PBMC and tissues by flow cytometry, but more importantly, for sorting of defined epitope-specific populations by microarray analysis (see below). Ab responses to gag and env are quantified in plasma and rectal washings by ELISA (Lu, X. et al. 1998. AIDS 12:1-10), with samples exhibiting env titres >1:100 analyzed for neutralization of SIVmac239 and tissue culture-adapted SIVmac251 (Montefiori, D. C. 2005. Curr Protoc Immunol Chapter 12:Unit 12 11).

Wildtype (wt) RhCMV/SIV vectors elicit high frequency and broadly targeted CD8+ TEM responses to SIV epitopes, yet do not include responses to the typical immunodominant epitopes targeted in SIV infection itself or after vaccination with DNA or conventional viral vectors. Applicants have further shown that this "hole" in the wt RhCMV/SIV vector-elicited CD8+ T cell targeting is a direct result of the action of CMV genes in the US2-11 region that prevent MHC class I-restricted presentation by infected cells, a mechanism that might serve CMV biology by directing CD8+ T cell responses away from epitopes most likely to allow for efficient direct CD8+ T cell recognition of CMV-infected cells, and therefore, efficient CD8+ T cell-mediated cytolysis. From an HIV/SIV vaccine perspective, this remarkable biology has several highly significant implications, including the possibility that the robust, but incomplete, protection elicited by wt RhCMV/SIV vectors might be enhanced by extending CD8+ T cell targeting to epitopes that are more efficiently processed and presented by SIV-infected cells. The addition of CD8+ T cell responses that recognize such epitopes might improve vaccine efficacy by increasing the efficiency of direct CD8+ T cell recognition of SIV-infected cells, allowing for more effective cytolysis or more accurately directed (proximate) non-cytolytic effector mechanisms (compared to indirectly presented epitopes by nearby uninfected cells). To Applicants' knowledge, the ability to turn "off" and "on" a specific CD8+ T cell recognition pattern by simple modification of a viral vaccine vector is unprecedented, certainly in the SIV vaccine model, and offers a unique opportunity to define the impact of the pattern of CD8+ recognition on the ability of vaccine-elicited CD8+ T cell responses to suppress and perhaps even clear primary SIV infection. Such information would clearly extend Applicants' understanding of immunologic requirements for CD8+ T cell-mediated protection in the SIV model, but would also have a major impact on the translation pathway of CMV vectors into a human HIV/AIDS vaccine candidate. The finding of enhanced efficacy of US2-11 deletant vectors would provide a strong impetus to take advantage of this superior protection, either by steering CMV vector development towards constructs with this deletion and therefore targeted towards CMV-naïve populations (pediatric populations, almost certainly with additional vector modifications to increase safety) or by the development of constructs which may present "internally processed" epitopes, yet retain the ability to re-infect CMV-seropositive individuals (perhaps by more limited—sub-region or specific gene—deletions in the US2-11 region).

Example 3: A Systematic Evaluation of Cytomegalovirus Vaccine Efficacy

Although human cytomegalovirus (HCMV) causes a mostly benign, unnoticed persistent infection in immunocompetent individuals, it may cause disease in immunocompromised individuals such as transplant or AIDS patients. HCMV is also the most frequent infectious cause of birth defects, with an estimated 0.7% of babies in the APPLICANTS being born with congenital infection, and approximately 10% of these infections resulting in long-term sequelae (primarily sensorineural defects) (Dollard, S. C. et al. 2007. Rev Med Virol 17:355-63). The annual health costs to care for these children is estimated to be about $1-2 billion (Cannon, M. J., and K. F. Davis. 2005. BMC Public Health 5:70). For these reasons, the development of a CMV vaccine has been given high priority by the Institute of Medicine and the National Vaccine Advisory Committee (Arvin, A. M. et al. 2004. Clin Infect Dis 39:233-9). However, the development of a vaccine has been frustratingly slow despite efforts for more than 30 years (Dekker, C. L., and A. M. Arvin. 2009. N Engl J Med 360:1250-2.). A major, if not the major, road-block for CMV vaccine development is the fact that immunity from natural infection or vaccination offers only very limited, if any, protection against re-infection by CMV (Adler, S. P. et al. 1995. J Infect Dis 171:26-32 and Boppana, S. B. et al. 2001. N Engl J Med 344:1366-71). This unique characteristic of CMV that prevents 'protection from infection' being used as a read-out for vaccine efficacy has rendered it very difficult to evaluate candidate CMV vaccines, with current measures relying primarily on more subjective criteria such as reduction in disease symptoms (Gonczol, E., and S. Plotkin. 2001. Expert Opin Biol Ther 1:401-12). The mechanism by which CMV achieves this unique ability to re-infect in the presence of pre-existing immunity has not been understood until recently. Using the rhesus macaque (RM) model, Applicants' team demonstrated that rhesus CMV (RhCMV) may repeatedly re-infect sero-positive animals even when the same strain of CMV is used and an high level of antibody and T cell immunity is present (Hansen, S. G. et al. 2009. Nat Med 15:293-9 and Price, D. A. et al. 2008. J Immunol 180:269-). In preliminary experiments Applicants further show that such re-infection occurs with as little as 100 plaque-forming units (PFU) given subcutaneously (s.c.). Remarkably, re-infection of sero-positive animals is prevented when Applicants use a RhCMV recombinant (designated ΔRh182-9) that has lost its ability to prevent antigen presentation by major histocompatibility complex class I (MHC-I) due to deletion of the RhCMV homologues of the US6 family of HCMV immunevasins, US2-US11. Depletion of CD8+ T cells restores the ability of ΔRh182-9 to re-infect sero-positive RMs, showing that inhibition of antigen presentation is one of the underlying reasons for re-infection.

Importantly, the capacity of immunity induced by natural CMV infection to protect against the US2-11 deleted virus ΔRh182-9 is thus an excellent measure for the quality of the CD8+ T cell response against CMV induced naturally by prior infection or artificially by vaccination. This measure far surpasses all other means currently available to monitor CMV vaccine efficacy, since it is effectively 'all-or-none': once the sites of persistence have been reached by ΔRh182-9 (even by a few viruses) long-term infection and easily detectable levels of viral shedding occur. In contrast, other measures such as viremia and clinical signs of infection are notoriously variable, subjective, and are especially problematic where vaccine effects are rather subtle. Applicants therefore propose to use protection against ΔRh182-9 to systematically re-evaluate some of the basic assumptions regarding vaccine approaches that have been made over the years regarding CMV vaccines. This allows Applicants to develop empirically based recommendations for the best strategy to develop a vaccine against HCMV. To accelerate future development of HCMV-based vaccines Applicants also generate and characterize in vitro recombinant HCMVs containing the same attenuating genetic disruptions present in the attenuated RhCMV vaccines.

Applicants' recent findings using a RhCMV virus deleted for the US2-11 genes (ΔRh182-9) show that this family of immune evasion genes is responsible for the ability of CMV to re-infect the healthy sero-positive host. Applicants' subsequent observation that CD8+ depletion prior to challenge overcomes the block to ΔRh182-9 infection in CMV sero-positive animals shows that the US6 family proteins function by their effect on the CMV-specific CD8+ T cell response. Thus, ΔRh182-9 infection may serve as an all-or-none read-out for whether a CMV-specific CD8+ T cell immune response is functionally comparable to that induced by natural WT CMV infection.

CMV possesses the remarkable ability to re-infect and establish a persistent infection regardless of host CMV immunity (Boppana, S. B. et al. 1999. Pediatrics 104:55-60, Farroway, L. N. et al. 2005. Epidemiol Infect 133:701-10 and Hansen, S. G. et al. 2009. Nat Med 15:293-9) (FIG. 31). After initial infection, CMV is shed for years from epithelial surfaces into body fluids (saliva, tears, urine, genital secretions and breast milk), and transmission generally involves mucosal exposure to such fluids, most commonly in early childhood or adolescence (Boppana, S. B. et al. 1999. Pediatrics 104:55-60 and Pass, R. F. 2001. Cytomegalovirus, p. 2675-2705. In P. M. H. David M. Knipe, Diane E. Griffin, Robert A. Lamb Malcolm A. Martin, Bernard Roizman and Stephen E. Straus (ed.), Fields Virology, 4th ed. Lippincott Williams & Wilkins, Philadelphia). In humans, the inability of natural HCMV immunity to protect against re-infection was initially demonstrated in an early human vaccine trial, wherein re-infection using low doses of a replicating HCMV strain, Toledo-1, was observed in healthy HCMV sero-positives (Plotkin, S. A. et al. 1989. J Infect Dis 159:860-5 and Quinnan, G. V. et al. 1984. Ann Intern Med 101:478-83). Evidence for re-infection and virus persistence was observed by virus isolation from one individual (10 pfu group), and induction of an amnestic anti-HCMV antibody response in a second individual (100 pfu group)—although no individuals receiving doses of either 10 (n=2), or 100 pfu (n=5) showed any HCMV-associated symptoms. All individuals in a third sero-positive group that received 1,000 pfu of Toledo-1 (n=5) showed evidence of infection, comprised of an amnestic HCMV-specific antibody and T cell response. Virus was also detected in throat swabs and urine from one symptomatically infected individual, and in the blood from a second asymptomatic individual. Toledo-1 was administered via a parenteral (subcutaneous) route, and it is possible that protection against natural infection via mucosal routes may by impacted by HCMV immunity (Adler, S. P. et al. 1995. J Infect Dis 171:26-32). However, a study performed in a cohort of 46 HCMV sero-positive pregnant women using CMV strain-specific antibodies as an indicator of re-infection suggests that natural HCMV re-infection of the sero-positive healthy adult is a common occurrence (Boppana, S. B. et al. 2001. N Engl J Med 344:1366-71).

In contrast to the limited effect of HCMV-induced immunity on preventing re-infection, maternal HCMV immunity reduces both transmission of HCMV to the fetus (Fowler, K. B. et al. 2003. JAMA 289:1008-11), as well as the occurrence of disease following infection in congenitally-infected infants (Fowler, K. B. et al. 1992. N Engl J Med 326:663-7 and Ross, S. A. et al. 2006. J Pediatr 148:332-6). In an initial study by Fowler et al (Fowler, K. B. et al. 2003. JAMA 289:1008-11), maternal HCMV sero-positivity corresponded to a 70% reduction in the risk of congenital HCMV infection. A more recent exhaustive meta-analysis, analyzing results from epidemiologic studies published between 1966 and 2006 showed the rate of congenital HCMV transmission to be 1.4% compared to 32% in HCMV sero-positive and sero-negative mothers, respectively (Keenan, R. J. et al. 1991. Transplantation 51:433-8). The impact of maternal HCMV sero-status on disease outcome of congenital infection has not been as thoroughly explored. However, the existing evidence suggests that maternal HCMV sero-positivity reduces the severity of congenital disease (Fowler, K. B. et al. 1992. N Engl J Med 326:663-7 and Ross, S. A. et al. 2006. J Pediatr 148:332-6). In one study, the incidence of symptomatic disease was 25% compared to 8% in congenitally infected infants from primary and recurrently infected mothers, respectively (Fowler, K. B. et al. 1992. N Engl J Med 326:663-7). In a second study, although the frequency of hearing loss was comparable in congenitally-infected infants following primary or recurrent infection, the severity of the hearing deficit was greater in congenitally infected infants following maternal primary infection (Ross, S. A. et al. 2006. J Pediatr 148:332-6). Both humoral and cellular CMV-specific responses appear to play a role in reducing transmission (for review, see (Adler, S. P. 2008. J Clin Virol 41:231-6)). This importance of CMV-specific T cell responses is most clearly shown by the increased incidence of CMV transmission to the fetus in mothers with T cell deficiency from AIDS (Adler, S. P. 2008. J Clin Virol 41:231-6 and Doyle, M. et al. 1996. Pediatr Infect Dis J 15:1102-6). Together, these studies suggest that a realistic goal of an HCMV vaccine is to reduce the incidence and severity of congenital CMV disease.

The poor efficacy of any vaccine approach tested to date is consistent with the inability of natural CMV immunity to protect from re-infection. The greatest level of protection for any HCMV human vaccine trial was recently observed using a recombinantly-expressed HCMV envelope gB with MF59 adjuvant-based approach in a placebo-controlled clinical trial (Pass, R. F. et al. 2009. N Engl J Med 360:1191-9). However, the difference in protection between vaccinees and saline controls was less than two-fold (7.7% compared to 13.5% in saline control group), was not robust as incorrect assignment of a small number of subjects could have eliminated statistical significance, and although a trend towards an effect on congenital infection was suggested (1 case of congenital infection, compared to 3 cases in saline control group; note after study stopped 2 additional congenital infections in saline group), this difference was not statistically significant. Based on the level of protection afforded in this study, it was estimated that a study adopting symptomatic congenital infection as an endpoint would require enrollment of >50,000 women (Dekker, C. L., and A. M. Arvin. 2009. N Engl J Med 360:1250-2). The lack of any statistically significant immune correlate with protection of the fetus, and the necessarily rigorous safety restrictions of vaccine trials performed in women of reproductive age are further concerns that are essentially prohibitive to any thorough analysis of HCMV vaccine candidates designed to interrupt maternal to fetal transmission of CMV.

In summary, although immunity induced by natural WT CMV infection is unable to protect against re-infection, it does afford a significant level of protection against congenital infection and severity of disease. This observation would suggest that a vaccine that may safely induce a level of immunity comparable to that induced by WT CMV infection may have a significant impact on congenital infection. The necessarily strict safety restrictions for analysis of candidate CMV vaccines in this target population (ie., CMV sero-negative women of child bearing age, and sero-negative pregnant women), pose significant problems for vaccine development, and probably preclude the use of any approach but a fully replication-defective based strategy. This limitation of human vaccine trials leaves unanswered the critical question of what level of vaccine attenuation may be achieved whilst still inducing a level of immunity comparable to that acquired through natural CMV infection (ie., an immunity that may decrease congenital infection). Currently, a non-human primate model to study CMV maternal to fetal transmission does not exist, and the genetically divergent rodent models do not completely translate to human HCMV infection. In this Example, Applicants propose that use of a dual-challenge strategy combining a) the all-or-none read-out of ΔRh182-9 challenge, with b) the continuous variable of viremia following WT-RhCMV s.c. challenge, are able to determine the minimal requirements for induction of a CMV-specific immunity that functionally recapitulates immunity induced by WT CMV infection. The biochemical comparison for these attenuated RhCMVs in parallel with their HCMV counterparts containing the identical genetic lesion ensure that any attenuated RhCMV showing protection may be translated into the HCMV 'strain of choice' with the confidence that the genetic deletion results in an HCMV vaccine with a comparable biochemical phenotype.

There is ample evidence that re-infection occurs in HCMV (Boppana, S. B. et al. 2001. N Engl J Med 344: 1366-71 and Ross, S. A. et al. 2006. J Pediatr 148:332-6). In the RM model Applicants previously showed that CMV-positive RMs could be repeatedly re-infected with 107 plaque forming units (PFU) of recombinant RhCMV (Hansen, S. G. et al. 2009. Nat Med 15:293-9). Each re-infection was detected as a boost in the anti-CMV T cell response and by the development of a de novo response to a new SIV antigen marker present only in the re-infecting virus. To determine whether re-infection also occurs at lower doses of RhCMV, Applicants infected sero-positive RMs with decreasing titers of RhCMV expressing SIV Gag (RhCMV-Gag). Re-infection was followed immunologically by measuring SIV Gag-specific T cell responses (Hansen, S. G. et al. 2009. Nat Med 15:293-9). When sero-positive animals were inoculated s.c. with 104 or 102 PFU of RhCMV-Gag a significant Gag-specific T cell response was observed at 14 days post-infection (p.i.) (FIG. 31). This Gag-specific response remained detectable for the duration of the experiment. Based on Applicants' experience in comparable studies, Gag responses are detectable for the life of the animal (>7 years p.i.) indicating a long-term persistent infection.

To determine whether Gag-expressing virus was shed by infected animals, Applicants sampled saliva and urine on a weekly basis. Upon co-culturing virus pellets with RM fibroblasts (RFs), Applicants monitored Gag expression in immunoblots. In animals that received 107 PFU of RhCMV-Gag, Applicants detected Gag-positive virus in the urine of some animals within 7-14 days p.i., and in all animals by 42 days p.i. Similarly, buccal swabs of all animals were positive by 70 days p.i. Animals inoculated with lower doses had a trend toward longer time p.i. before detection of RhCMV-Gag in saliva and urine, but all animals were eventually positive. Consistent with previous published studies for HCMV (Plotkin, S. A. et al. 1989. J Infect Dis 159:860-5 and Quinnan, G. V. et al. 1984. Ann Intern Med 101:478-83), these data show that prior infection by RhCMV does not protect against re-infection, even at CMV doses as low as 100 PFU. These results also indicate that the de novo immune response against a foreign antigen is a more sensitive and reproducible indicator of CMV re-infection than the detection of virus in the secretions.

The ease with which RhCMV overcomes a substantial, pre-existing anti-CMV immune response during re-infection suggests that CMV has evolved mechanisms to evade host immune surveillance. The adaptive cellular immune response is known to be particularly important for controlling CMV. In humans, CMV-specific T cells comprise on average approximately 10% of both the CD4+ and CD8+ memory compartments (Sylwester, A. W. et al. 2005. J Exp Med 202:673-85) suggesting that enormous resources are constantly devoted to controlling this virus. Applicants hypothesized that a key aspect of re-infection might be the ability of CMV to escape T cell detection. All CMVs are known to encode multiple proteins that prevent antigen presentation by MHC-I, thus limiting the ability of CD8+ T cells to recognize and eliminate CMV-infected cells (Loenen, W. A. et al. 2001. Semin Immunol 13:41-9). Applicants previously demonstrated that the RhCMV genomic region Rh182-Rh189 encodes functional homologues of the US2, US3, US6 and US11 immunevasins of HCMV (Pande, N. T. et al. 2005. J Virol 79:5786-98). To determine whether these viral inhibitors of antigen presentation were required for re-infection, Applicants replaced the Rh182-189 region with an expression cassette for the SIV Gag antigen, which allowed Applicants to monitor Gag-specific immune responses in infected animals (virus designated ΔRh182-9Gag). Deletion of the Rh182-9 region was confirmed by PCR and Southern Blot. Applicants further monitored in vitro growth in primary RFs and observed no difference to WT, BAC-derived RhCMV (data not shown). Initially, Applicants determined whether ΔRh182-9Gag would be able to establish persistent infection in CMV-negative animals. Applicants infected two sero-negative animals with $5\times10^6$ PFU of ΔRh182-9Gag and two control animals with the RhCMV-Gag (Hansen, S. G. et al. 2009. Nat Med 15:293-9.). Infection was monitored immunologically by the development of a CMV-specific and SIV Gag-specific immune responses and virologically by viral shedding of Gag-marked viruses into the urine and saliva. As shown in FIG. 32, a Gag-specific T cell response to ΔRh182-9Gag was detectable with similar kinetics and magnitude as responses against RhCMV-Gag. Moreover, ΔRh182-9Gag (confirmed by immunoblot) was detected in the secretions of the infected animals even >1 year p.i. (data not shown). Therefore, Applicants conclude that ΔRh182-9Gag is competent to establish persistent infection in CMV-naïve animals.

To determine whether ΔRh182-9Gag would be able to re-infect sero-positive animals Applicants inoculated CMV+ RMs s.c. with $10^7$ PFU. Consistent with Applicants' previous observations, the WT control RhCMV-Gag re-infected all four animals as evidenced by detection of SIV Gag-specific T cell responses in bronchoalveolar lavage (BAL) and peripheral blood mononuclear cells (PBMC) (FIG. 33A). In contrast, none of the four animals infected with ΔRh182-9Gag displayed any detectable signs of re-infection either by T cell assay (FIG. 33B) or by monitoring secretions for virus (data not shown). This lack of re-infection was not due to these animals being refractory to re-infection as the same animals could be re-infected with ΔRh178Gag, a virus that lacks a RhCMV-specific MHC-I evasion gene that has no HCMV counterpart (Powers, C. J., and K. Fruh. 2008. PLoS Pathog 4:e1000150) (FIG. 33C). Together, these experiments suggest that inhibition of antigen presentation by the US6 family (US2-11 genes) of immunomodulators is essential for RhCMV re-infection of the sero-positive host.

Since ΔRh182-9Gag was able to infect CMV-naïve animals, but not CMV-positive animals, Applicants hypothesized that the CMV-specific immune response, and particularly the CD8+ T cell response, prevented re-infection by the "immunologically defenseless" ΔRh182-9Gag virus. To test this hypothesis Applicants immuno-depleted CD8+ T cells from sero-positive RMs prior to re-infection with ΔRh182-9Gag. Serial injections of antibody cM-T807 (Schmitz, J. E. et al. 1999. Science 283:857-60) temporarily reduced CD8+ T cells for the duration of approximately 2-3 weeks (FIG. 34A). All four CMV-positive, immuno-depleted animals were re-infected by ΔRh182-9Gag as shown by SIV Gag-specific CD4+ T cell responses which were observed at 7 days p.i. (FIG. 34B). Interestingly, the animals even generated Gag-specific CD8+ T cell responses when CD8+ levels rebounded. Moreover, both CD4+ and CD8+ T cells were detectable for the remainder of the experiment suggesting that a persistent infection had been established. Applicants are currently examining secretions by co-culture for presence of ΔRh182-9Gag. Applicants conclude that CMV-encoded immunevasins enable re-infection of the sero-positive host due to their ability to evade the host CMV-specific CD8+ T response. However, immunity induced by natural CMV infection is able to protect against CMV re-infection in the absence of these virally encoded immunevasins.

For the first time, Applicants' data establish a clear causal relationship between viral immune modulation (by immunevasins) and the unique ability of CMV to re-infect the sero-positive host. Given the close evolutionary relationship between the humans and RMs, as well as the functional conservation of US2, 3, 6 and 11 between HCMV and RhCMV, Applicants consider it highly likely that the ability of HCMV to re-infect humans is also mediated by inhibitors of antigen presentation. These observations also have another implication that is highly relevant to the goal of vaccine development. Specifically, this is the first time that CMV-specific immunity in a primate species has been shown to completely prevent re-infection by CMV, even at a very high doses of challenge virus. Applicants therefore conclude that protection against ΔRh182-9 is an all-or-none measure for the quality of the pre-existing CMV specific immune response.

Thus, challenge with ΔRh182-9Gag may be used to determine whether any type of vaccination effort has successfully generated a CD8+ T cell response that is as protective as that induced by natural infection. Applicants anticipate that this assay is far superior to any other measure of CMV-vaccine efficacy, since this all-or-nothing read-out allows candidate vaccine efficacy to be determined using relatively small groups of animals. Using ΔRh182-9Gag challenge, Applicants re-examine whether non-replicating, partially replicating or non-replicating heterologous 'prime-boost' vaccines are able to induce a protective response.

Given the clear demonstration that HCMV re-infection of the fully immune host may efficiently occur even at low doses of virus, it seems that complete prevention of infection in vaccinees is likely not realistically an achievable goal. However, substantial epidemiological data shows that CMV immunity afforded by natural CMV infection significantly decreases maternal to fetal transmission of CMV. Thus, a reasonable and achievable goal for a CMV vaccine is to develop a vaccine that mimics immunity induced by primary infection, and thereby reduces transmission of CMV from the mother to the fetus (Adler, S. P. et al. 1995. J Infect Dis 171:26-32). Such a vaccine has to be extremely safe since the target population includes pregnant women. Finding an optimal balance between safety and efficacy has been a major obstacle in CMV vaccine development. This is, in large part, because the unique ability of CMV to re-infect CMV-immune individuals renders it difficult, if not impossible, to use protection from infection as a final read-out (at least in closely related primate models). For this reason, a major unsolved question is at what level of attenuation a vaccine still induces a level of immunity comparable to natural CMV infection, and thereby achieve the maximal level of "protective" efficacy realistically achievable. Applicants' goal is to address this critical question, and determine the level of attenuation of CMV at which an immune response equivalent to natural immunity is still generated. Applicants address this question in the RhCMV/RM infection model—a model that closely mimics HCMV infection in humans, but that permits empirical 'fine-tuning' of the level of CMV attenuation. In the first approach, Applicants address the question of whether replication-deficient CMV-based vaccines, either single- or low-cycle, are sufficient to induce a CMV-specific immune response and, following the induction of an immune response, what are the characteristics of immunity, regarding duration, magnitude and T cell phenotype. In a separate approach, Applicants introduce an on/off switch into the RhCMV genome which allow Applicants to inhibit or re-start viral replication at any time after infection thus addressing the roles of initial virus dissemination to sites of latent/persistent infection in the host, as well as of acute versus persistent replication in inducing a CMV-specific immune response. To overcome the problem in measuring efficacy of the immune response induced by the various attenuation strategies, Applicants propose to use the ability of a vaccine to protect against the US2-11 deleted recombinant virus ΔRh1829Gag. In addition to the attenuated vaccines, Applicants also evaluate the ability of 'Prime-Boost' vaccines (IE-1, pp65b, gB) to prevent ΔRh182-9Gag re-infection using a DNA prime/adenovirus boost strategy. Vaccinated animals that were protected against ΔRh182-9Gag are further challenged with WT-RhCMV followed by monitoring of viremia. Applicants anticipate that this dual-challenge strategy show that protection against re-infection with ΔRh182-9Gag correlates with the ability of a vaccine to reduce WT-RhCMV viremia, a much more difficult to monitor and variable read-out currently used to evaluate vaccine efficacy. Protection against ΔRh182-9Gag thus indicate that a given vaccine was able to generate a CMV-specific immune response, particularly a CD8+ T cell response, similar to that induced during natural infection. One of the great advantages of the RhCMV model is the close evolutionary relationship between the human and rhesus CMVs, and their respective hosts. Therefore, Applicants in parallel generate and characterize HCMV-derived constructs containing identical genetic deletions thereby ensuring that any of the attenuated vaccines that shows promise in the RhCMV system is functionally comparable to its HCMV counterpart. Applicants anticipate that results obtained in this project are directly transferable to development of an HCMV-based vaccine candidate.

Figure 23A:
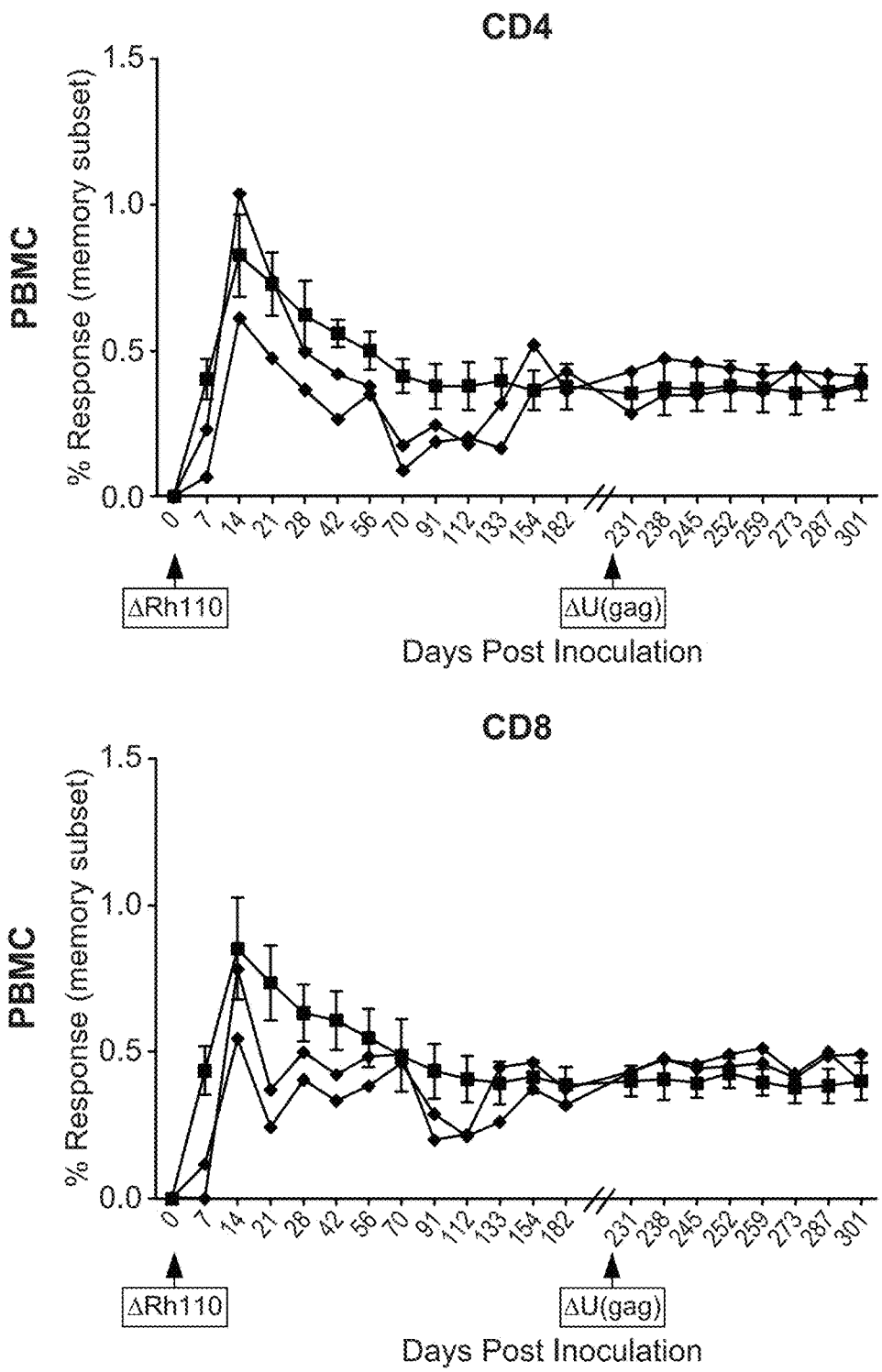
Figure 23C:
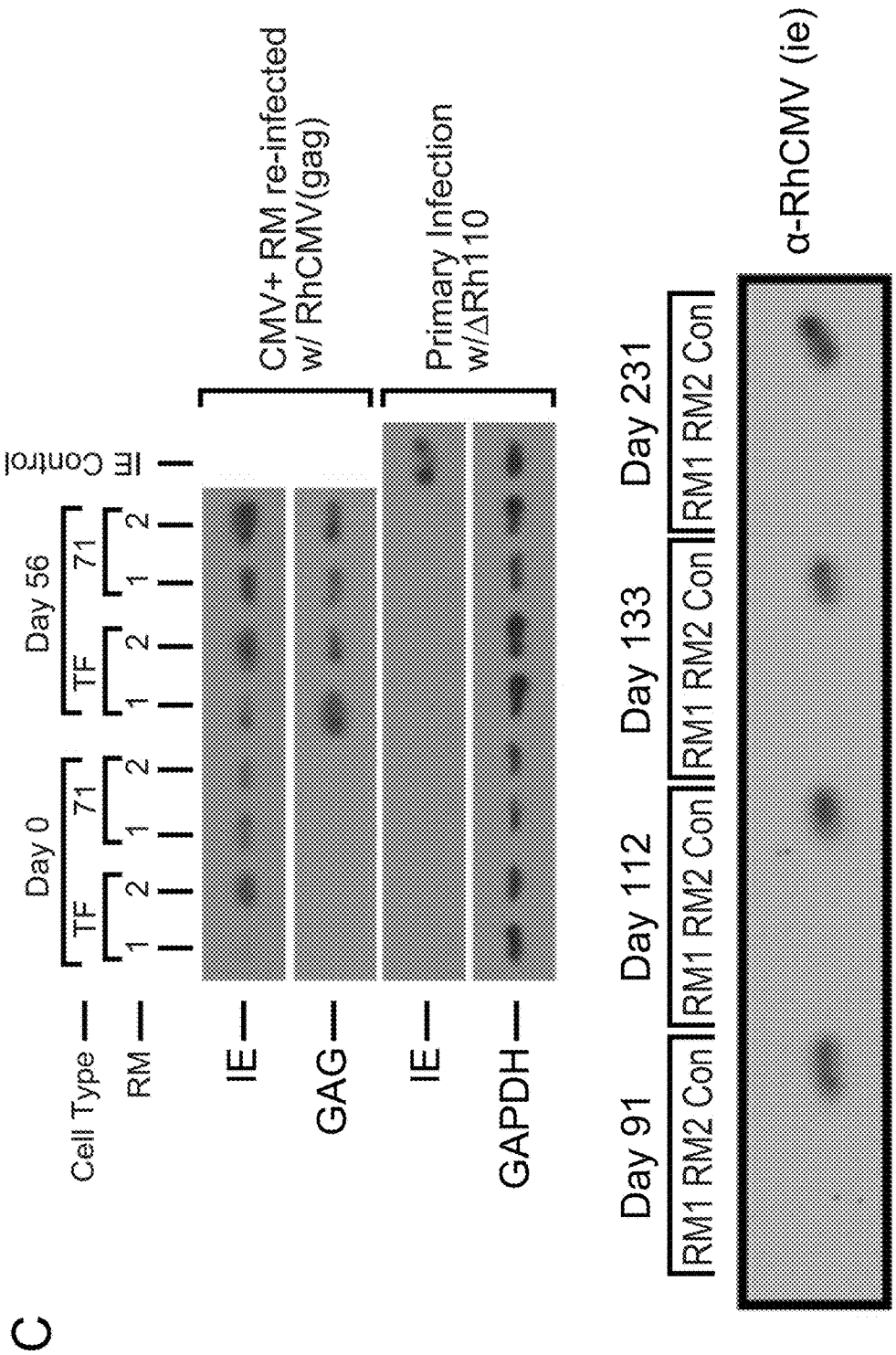

Example 4: A US2-11-Deleted Virus May be Used as a Testing Device for CMV-Vaccine Efficacy Applicants have infected rhesus macaques with RhCMV lacking the gene Rh110 that encodes for the viral transactivator pp71. RhCMVΔRh110 is growth-deficient in vitro but is not secreted from infected monkeys. Applicants have tested whether monkeys infected with RhCMVΔRh110 are protected against challenge with RhCMVΔUS2-11 expressing the SIV antigen Gag. Protection was demonstrated by the absence of a boost in RhCMV-specific T cell responses. In contrast, monkeys infected with wildtype-virus show a boost of the CMV-specific T cell response (see FIG. 23). This result indicates that spread-deficient CMV is capable of inducing a T cell response that protects against challenge with US2-11 deleted virus. This result also indicates that a US2-11 deleted virus may be used to monitor the efficacy of the T cell response.

In a similar experiment Applicants created a RhCMV lacking the tegument proteins pp65a and pp65b encoded by the genes Rh111 and Rh112, respectively (see FIG. 24). These proteins are not required for viral growth in vitro. However, pp65 is an immunodominant protein that is included in current formulations of subunit vaccines for CMV developed by various investigators. To examine whether pp65-specific T cells are required for protection against challenge with ΔUS2-11, Applicants infected rhesus macaques with RhCMVΔRh111-112. As expected Applicants observed an immune response against the IE-proteins of CMV, but not against pp65. In contrast, a pp65-specific T cell response was readily detected in animals infected with RhCMV (blue line). Applicants also observed that RhCMVΔRh111-112 is secreted from infected animals.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of determining efficacy of a cytomegalovirus (CMV) immunogenic composition comprising or expressing at least one CMV immunogen, wherein the method comprises the steps of:
   (a) detecting the presence of a pre-challenge CD8+ T cell response of a test subject to the at least one CMV immunogen;
   (b) challenging the test subject with a recombinant CMV challenge virus expressing the at least one CMV immunogen, wherein the glycoproteins US2, US3, US6 and US11 or orthologs thereof are deleted from the challenge virus, and wherein the challenge virus is capable of eliciting a CD8+ T cell response to the at least one CMV immunogen within a CMV seronegative host; and
   (c) detecting the presence or absence of a post-challenge CD8+ T cell response of the test subject to the at least one CMV immunogen;
   wherein the CMV immunogenic composition is efficacious in eliciting a protective immune response against CMV if a post-challenge boost to the CD8+ T cell response of the test subject to the at least one CMV immunogen is absent.

2. The method of claim 1, wherein:
   (i) the CMV seronegative test subject is a human CMV (HCMV) seronegative test subject,
   (ii) the at least one CMV immunogen is a HCMV immunogen, and
   (iii) the recombinant CMV challenge virus is a recombinant HCMV challenge virus.

3. The method of claim 1, wherein:
   (i) the CMV seronegative test subject is a rhesus CMV (RhCMV) seronegative test subject,
   (ii) the at least one CMV immunogen is a RhCMV immunogen, and
   (iii) the recombinant CMV challenge virus is a recombinant RhCMV challenge virus.

4. The method of claim 1, wherein the CMV immunogenic composition comprises an attenuated CMV strain.

5. The method of claim 4, wherein the CMV immunogenic composition lacks the transactivator pp71.

6. The method of claim 1, wherein the recombinant CMV challenge virus is a recombinant HCMV challenge virus, and wherein all glycoproteins within the US2 to US11 region are deleted from the recombinant HCMV challenge virus.

7. The method of claim 1, wherein the recombinant CMV challenge virus is a recombinant RhCMV challenge virus, and wherein all glycoproteins within the Rh182-189 region are deleted from the recombinant RhCMV challenge virus.

8. A method of determining efficacy of a CMV immunogenic composition comprising or expressing at least one CMV immunogen, wherein the method comprises the steps of:
   (a) detecting the presence of a pre-challenge CD8+ T cell response of a test subject to the at least one CMV immunogen and the absence of a pre-challenge CD8+ T cell response of the test subject to at least one additional immunogen expressed by a recombinant CMV challenge virus, wherein the CMV immunogenic composition does not comprise or express the at least one additional immunogen;
   (b) challenging the test subject with the recombinant CMV challenge virus expressing the at least one CMV immunogen and the at least one additional immunogen, wherein the glycoproteins US2, US3, US6 and US11 or orthologs thereof are deleted from the challenge virus, and wherein the recombinant CMV challenge virus is capable of eliciting a CD8+ T cell response to the at least one CMV immunogen and the at least one additional immunogen within a CMV seronegative host; and
   (c) detecting the presence or absence of a post-challenge CD8+ T cell response of the test subject to the at least one additional immunogen;

wherein the CMV immunogenic composition is efficacious in eliciting a protective immune response against CMV if a de novo post-challenge CD8+ T cell response of the test subject to the at least one additional immunogen is absent.

9. The method of claim 8, wherein:
   (i) the CMV seronegative test subject is a HCMV seronegative test subject,
   (ii) the at least one CMV immunogen is a HCMV immunogen, and
   (iii) the recombinant CMV challenge virus is a recombinant HCMV challenge virus.

10. The method of claim 8, wherein:
    (i) the CMV seronegative test subject is a RhCMV seronegative test subject,
    (ii) the at least one CMV immunogen is a RhCMV immunogen, and
    (iii) the recombinant CMV challenge virus is a recombinant RhCMV challenge virus.

11. The method of claim 8, wherein the CMV immunogenic composition comprises an attenuated CMV strain.

12. The method of claim 11, wherein the CMV immunogenic composition lacks the transactivator pp71.

13. The method of claim 8, wherein the recombinant CMV challenge virus is a recombinant HCMV challenge virus, and wherein all glycoproteins within the US2 to US11 region are deleted from the recombinant HCMV challenge virus.

14. The method of claim 8, wherein the recombinant CMV challenge virus is a recombinant RhCMV challenge virus, and wherein all glycoproteins within the Rh182-189 region are deleted from the recombinant RhCMV challenge virus.

15. The method of claim 8, wherein the at least one additional immunogen is a bacterial-derived immunogen, a parasite-derived immunogen, viral-derived immunogen, or a cancer-derived immunogen.

16. A method of determining efficacy of a CMV immunogenic composition comprising or expressing at least one CMV immunogen and at least one additional immunogen, wherein the method comprises the steps of:
    (a) detecting the presence of a pre-challenge CD8+ T cell response of a test subject to the at least one additional immunogen;
    (b) challenging the test subject with a recombinant CMV challenge virus expressing the at least one CMV immunogen and the at least one additional immunogen, wherein the glycoproteins US2, US3, US6 and US11 or orthologs thereof are deleted from the challenge virus, and wherein the recombinant CMV challenge virus is capable of eliciting a CD8+ T cell response to the at least one CMV immunogen and the at least one additional immunogen within a CMV seronegative host; and
    (c) detecting the presence or absence of a post-challenge CD8+ T cell response of the test subject to the at least one additional immunogen;
    wherein the CMV immunogenic composition is efficacious in eliciting a protective immune response against CMV if a boost to the CD8+ T cell response of the test subject to the at least one additional immunogen is absent.

17. The method of claim 16, wherein:
    (i) the CMV seronegative test subject is a HCMV seronegative test subject,
    (ii) the at least one CMV immunogen is a HCMV immunogen, and
    (iii) the recombinant CMV challenge virus is a recombinant HCMV challenge virus.

18. The method of claim 16, wherein:
    (i) the CMV seronegative test subject is a RhCMV seronegative test subject,
    (ii) the at least one CMV immunogen is a RhCMV immunogen, and
    (iii) the recombinant CMV challenge virus is a recombinant RhCMV challenge virus.

19. The method of claim 16, wherein the CMV immunogenic composition comprises an attenuated CMV strain.

20. The method of claim 19, wherein the CMV immunogenic composition lacks the transactivator pp71.

21. The method of claim 16, wherein the recombinant CMV challenge virus is a recombinant HCMV challenge virus, and wherein all glycoproteins within the US2 to US11 region are deleted from the recombinant HCMV challenge virus.

22. The method of claim 16, wherein the recombinant CMV challenge virus is a recombinant RhCMV challenge virus, and wherein all glycoproteins within the Rh182-189 region are deleted from the recombinant RhCMV challenge virus.

23. The method of claim 16, wherein the at least one additional immunogen is a bacterial-derived immunogen, a parasite-derived immunogen, viral-derived immunogen, or a cancer-derived immunogen.

24. A method of determining efficacy of a CMV immunogenic composition comprising or expressing at least one CMV immunogen, wherein the method comprises the steps of:
    (a) administering the immunogenic composition to a CMV seronegative test subject; and
    (b) challenging the test subject with a recombinant CMV challenge virus if a pre-challenge CD8+ T cell response to the at least one CMV immunogen is detected within the test subject, wherein the glycoproteins US2, US3, US6 and US11 or orthologs thereof are deleted from the challenge virus, and wherein the challenge virus expresses the at least one CMV immunogen and is capable of eliciting a CD8+ T cell response to the at least one CMV immunogen within a CMV seronegative host;
    wherein the CMV immunogenic composition is efficacious in eliciting a protective immune response against CMV if a post-challenge boost to the CD8+ T cell response of the test subject to the at least one CMV immunogen is absent.

25. The method of claim 24, wherein:
    (i) the CMV seronegative test subject is a HCMV seronegative test subject,
    (ii) the at least one CMV immunogen is a HCMV immunogen, and
    (iii) the recombinant CMV challenge virus is a recombinant HCMV challenge virus.

26. The method of claim 24, wherein:
    (i) the CMV seronegative test subject is a RhCMV seronegative test subject,
    (ii) the at least one CMV immunogen is a RhCMV immunogen, and
    (iii) the recombinant CMV challenge virus is a recombinant RhCMV challenge virus.

27. The method of claim 24, wherein the CMV immunogenic composition comprises an attenuated CMV strain.

28. The method of claim 27, wherein the CMV immunogenic composition lacks the transactivator pp71.

29. The method of claim 24, wherein the recombinant CMV challenge virus is a recombinant HCMV challenge virus, and wherein all glycoproteins within the US2 to US11 region are deleted from the recombinant HCMV challenge virus.

30. The method of claim 24, wherein the recombinant CMV challenge virus is a recombinant RhCMV challenge virus, and wherein all glycoproteins within the Rh182-189 region are deleted from the recombinant RhCMV challenge virus.

31. A method of determining efficacy of a CMV immunogenic composition comprising or expressing at least one CMV immunogen, wherein the method comprises the steps of:
(a) administering the CMV immunogenic composition to a HCMV seronegative test subject, wherein the CMV immunogenic composition does not comprise or express at least one additional immunogen expressed by a recombinant CMV challenge virus; and
(b) challenging the test subject with the recombinant CMV challenge virus if a pre-challenge CD8+ T cell response to the at least one CMV immunogen is detected within the test subject, wherein the glycoproteins US2, US3, US6 and US11 or orthologs thereof are deleted from the challenge virus, and wherein the recombinant CMV challenge virus is capable of eliciting a CD8+ T cell response to the at least one CMV immunogen and the at least one additional immunogen within a CMV seronegative host;
wherein the CMV immunogenic composition is efficacious in eliciting a protective immune response against CMV if a de novo post-challenge CD8+ T cell response of the test subject to the at least one additional immunogen is absent.

32. The method of claim 31, wherein:
(i) the CMV seronegative test subject is a HCMV seronegative test subject,
(ii) the at least one CMV immunogen is a HCMV immunogen, and
(iii) the recombinant CMV challenge virus is a recombinant HCMV challenge virus.

33. The method of claim 31, wherein:
(i) the CMV seronegative test subject is a RhCMV seronegative test subject,
(ii) the at least one CMV immunogen is a RhCMV immunogen, and
(iii) the recombinant CMV challenge virus is a recombinant RhCMV challenge virus.

34. The method of claim 31, wherein the CMV immunogenic composition comprises an attenuated CMV strain.

35. The method of claim 34, wherein the CMV immunogenic composition lacks the transactivator pp71.

36. The method of claim 31, wherein the recombinant CMV challenge virus is a recombinant HCMV challenge virus, and wherein all glycoproteins within the US2 to US11 region are deleted from the recombinant HCMV challenge virus.

37. The method of claim 31, wherein the recombinant CMV challenge virus is a recombinant RhCMV challenge virus, and wherein all glycoproteins within the Rh182-189 region are deleted from the recombinant RhCMV challenge virus.

38. The method of claim 31, wherein the at least one additional immunogen is a bacterial-derived immunogen, a parasite-derived immunogen, viral-derived immunogen, or a cancer-derived immunogen.

39. A method of determining efficacy of a CMV immunogenic composition comprising or expressing at least one CMV immunogen and at least one additional immunogen, wherein the method comprises the steps of:
(a) administering the CMV immunogenic composition to a CMV seropositive test subject; and
(b) challenging the test subject with a recombinant CMV challenge virus if pre-challenge CD8+ T cell responses to the at least one CMV immunogen and the at least one additional immunogen are detected within the test subject, wherein the glycoproteins US2, US3, US6 and US11 or orthologs thereof are deleted from the challenge virus, and wherein the recombinant CMV challenge virus expresses the at least one CMV immunogen and the at least one additional immunogen and is capable of eliciting CD8+ T cell responses to the at least one CMV immunogen and the at least one additional immunogen within a CMV seronegative host;
wherein the CMV immunogenic composition is efficacious eliciting a protective immune response against CMV if a boost to the CD8+ T cell response of the test subject to the at least one additional immunogen is absent.

40. The method of claim 39, wherein:
(i) the CMV seronegative test subject is a HCMV seronegative test subject,
(ii) the at least one CMV immunogen is a HCMV immunogen, and
(iii) the recombinant CMV challenge virus is a recombinant HCMV challenge virus.

41. The method of claim 39, wherein:
(i) the CMV seronegative test subject is a RhCMV seronegative test subject,
(ii) the at least one CMV immunogen is a RhCMV immunogen, and
(iii) the recombinant CMV challenge virus is a recombinant RhCMV challenge virus.

42. The method of claim 39, wherein the CMV immunogenic composition comprises an attenuated CMV strain.

43. The method of claim 42, wherein the CMV immunogenic composition lacks the transactivator pp71.

44. The method of claim 39, wherein the recombinant CMV challenge virus is a recombinant HCMV challenge virus, and wherein all glycoproteins within the US2 to US11 region are deleted from the recombinant HCMV challenge virus.

45. The method of claim 39, wherein the recombinant CMV challenge virus is a recombinant RhCMV challenge virus, and wherein all glycoproteins within the Rh182-189 region are deleted from the recombinant RhCMV challenge virus.

46. The method of claim 39, wherein the at least one additional immunogen is a bacterial-derived immunogen, a parasite-derived immunogen, viral-derived immunogen, or a cancer-derived immunogen.

\* \* \* \* \*